US009470929B2

(12) United States Patent
Suwa et al.

(10) Patent No.: US 9,470,929 B2
(45) Date of Patent: Oct. 18, 2016

(54) LIQUID CRYSTAL DISPLAY UNIT AND METHOD OF MANUFACTURING THE SAME

(71) Applicant: Sony Corporation, Tokyo (JP)

(72) Inventors: Shunichi Suwa, Kanagawa (JP); Yuichi Inoue, Kanagawa (JP); Ryo Ogawa, Tokyo (JP); Tsuyoshi Kamada, Kanagawa (JP); Masashi Miyakawa, Tokyo (JP); Tadaaki Isozaki, Kanagawa (JP); Masahiko Nakamura, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/570,523

(22) Filed: Dec. 15, 2014

(65) Prior Publication Data
US 2016/0011463 A1    Jan. 14, 2016

Related U.S. Application Data

(63) Continuation of application No. 12/888,875, filed on Sep. 23, 2010, now Pat. No. 8,945,692, which is a continuation of application No. PCT/JP2010/050783, filed on Jan. 22, 2010.

(30) Foreign Application Priority Data

Jan. 30, 2009  (JP) ................................ 2009-020654
Sep.  1, 2009  (JP) ................................ 2009-201926
Sep. 30, 2009  (JP) ................................ 2009-228728
Dec. 22, 2009  (JP) ................................ 2009-290979

(51) Int. Cl.
  *G02F 1/1337*    (2006.01)
  *C08G 73/10*     (2006.01)
  (Continued)

(52) U.S. Cl.
  CPC ......... *G02F 1/133711* (2013.01); *C07C 49/84* (2013.01); *C07C 69/736* (2013.01);
  (Continued)

(58) Field of Classification Search
  CPC ........... G02F 1/1337; G02F 1/133707; G02F 1/133711; G02F 1/133753; G02F 1/133788; G02F 2001/133773; G02F 2001/13706; G02F 2001/13726; G02F 2001/133749; Y10T 428/1005; Y10T 428/1059; Y10T 428/1082
  See application file for complete search history.

(56) References Cited

U.S. PATENT DOCUMENTS 8,619,222 B2  12/2013  Nakamura et al.
8,696,950 B2   4/2014  Suwa et al.
(Continued)

FOREIGN PATENT DOCUMENTS

CN   1395593   2/2003
CN   1869779   11/2006
(Continued)

OTHER PUBLICATIONS

Chinese Office Action issued in connection with related Chinese Patent Application No. CN 201080013901.9.X dated Oct. 18, 2013.
(Continued)

*Primary Examiner* — Shean C Wu
(74) *Attorney, Agent, or Firm* — Dentons US LLP

(57) ABSTRACT

A method of manufacturing a liquid crystal display device with which response characteristics are able to be easily improved without using major equipment is provided. The method of manufacturing a liquid crystal display device includes steps of forming a first alignment film including a polymer compound having a crosslinkable functional group as a side chain on one substrate of a pair of substrates; forming a second alignment film on the other substrate of the pair of substrates; arranging the pair of substrates so that the first alignment film and the second alignment film are opposed to each other, and sealing a liquid crystal layer containing a liquid crystal molecule having negative dielectric constant anisotropy between the first alignment film and the second alignment film; and bridging the polymer compound to give pre-tilt to the liquid crystal molecule 41 after sealing the liquid crystal layer.

18 Claims, 16 Drawing Sheets

(51) Int. Cl.
- *C07C 49/84* (2006.01)
- *C07C 69/736* (2006.01)
- *C07C 69/76* (2006.01)
- *C07J 9/00* (2006.01)
- *C09K 19/56* (2006.01)
- *G02F 1/1339* (2006.01)
- *G02F 1/137* (2006.01)

(52) U.S. Cl.
CPC ............... *C07C 69/76* (2013.01); *C07J 9/00* (2013.01); *C07J 9/005* (2013.01); *C08G 73/1075* (2013.01); *C09K 19/56* (2013.01); *G02F 1/1339* (2013.01); *G02F 1/133788* (2013.01); *G02F 1/133707* (2013.01); *G02F 2001/13706* (2013.01); *G02F 2001/13712* (2013.01); *G02F 2001/133715* (2013.01); *G02F 2001/133726* (2013.01); *G02F 2001/133749* (2013.01); *G02F 2001/133773* (2013.01); *Y10T 156/10* (2015.01); *Y10T 428/1005* (2015.01); *Y10T 428/1059* (2015.01); *Y10T 428/1082* (2015.01)

(56) References Cited

U.S. PATENT DOCUMENTS

| | | | |
|---|---|---|---|
| 8,945,692 | B2 * | 2/2015 | Suwa ............... G02F 1/133711 349/124 |
| 2004/0080685 | A1 | 4/2004 | Yamada |
| 2008/0055521 | A1 | 3/2008 | Mizutani et al. |
| 2009/0079923 | A1 | 3/2009 | Miyachi |
| 2010/0085523 | A1 | 4/2010 | Terashita et al. |
| 2011/0273652 | A1 | 11/2011 | Suwa et al. |
| 2012/0212691 | A1 | 8/2012 | Miyakawa et al. |
| 2012/0212697 | A1 | 8/2012 | Miyakawa et al. |
| 2012/0218500 | A1 | 8/2012 | Nakamura et al. |

FOREIGN PATENT DOCUMENTS

| | | |
|---|---|---|
| JP | 04-250822 | 12/1992 |
| JP | HEI 10-073832 | 3/1998 |
| JP | HEI 10-087859 | 4/1998 |
| JP | HEI 10-170921 | 6/1998 |
| JP | HEI 10-232400 | 9/1998 |
| JP | HEI 10-252646 | 9/1998 |
| JP | HEI 11-133430 | 5/1999 |
| JP | HEI 11-326638 | 11/1999 |
| JP | 2000-193976 | 7/2000 |
| JP | 2001-517719 | 10/2001 |
| JP | 2002-082336 | 3/2002 |
| JP | 2003-073471 | 3/2003 |
| JP | 2008-262074 | 10/2008 |
| TW | 200702849 A | 1/2007 |
| WO | WO/9744704 | 11/1997 |
| WO | WO/2006/121220 | 11/2006 |
| WO | WO/2008/117615 | 10/2008 |
| WO | 2009-133803 | 11/2009 |

OTHER PUBLICATIONS

European Search Report issued in connection with related European Patent Application No. 11005868.2 dated Feb. 14, 2013.
European Search Report issued in connection with related European Patent Application No. 10735749.3 dated Feb. 14, 2013.
European Search Report issued in connection with related European Patent Application No. 11005869.0 dated Feb. 14, 2013.
European Search Report issued in connection with related European Patent Application No. 10735750.1 dated Feb. 14, 2013.
International Search Report issued in connection with related PCT/JP210/050783 dated Apr. 20, 2010.
Chinese Office Examination Report issued in connection with related Chinese Application No. CN 201080013019.X dated Oct. 29, 2014.
Chinese Office Examination Report issued in connection with related Chinese Application No. CN 201080013022.1 dated Nov. 4, 2014.
Japanese Office Action corresponding to Japanese Serial No. 2014-057660 dated Apr. 28, 2015.

* cited by examiner

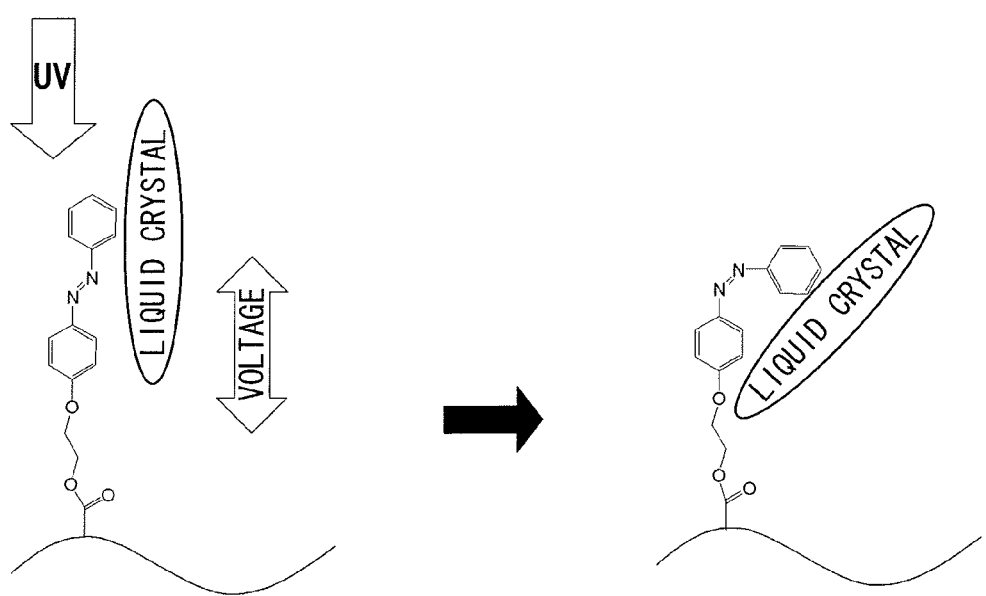
F I G. 16

LIQUID CRYSTAL DISPLAY UNIT AND METHOD OF MANUFACTURING THE SAME

RELATED APPLICATION DATA

The present application is a continuation of application Ser. No. 12/888,875 filed Jan. 10, 2010, which is a continuation of PCT/JP2010/050783, filed on Jan. 22, 2010, which is the international application of Japanese Application No. 2009-020654 filed on Jan. 30, 2009, Japanese Application No. 2009-201926 filed on Sep. 1, 2009, Japanese Application No. 2009-228728 filed on Sep. 30, 2009, and Japanese Application No. 2009-290979 filed on Dec. 22, 2009. The benefit of priority is claimed to all applications, and all applications are fully incorporated herein by reference to the extent permitted by law.

TECHNICAL FIELD

The present invention relates to a liquid crystal display unit that includes a liquid crystal display device in which a liquid crystal layer is sealed between a pair of substrates having an alignment film on opposed faces thereof and a method of manufacturing the liquid crystal display unit.

BACKGROUND ART

In recent years, a liquid crystal display (LCD: Liquid Crystal Display) is often used as a display monitor for a liquid crystal television, a notebook personal computer, a car navigation system and the like. The liquid crystal display is categorized into various display modes (methods) according to molecular arrangement (alignment) of liquid crystal molecules contained in a liquid crystal layer sandwiched by substrates. As a display mode, TN (Twisted Nematic) mode in which twisted liquid crystal molecules are aligned in a state that a voltage is not applied is well-known. In the TN mode, the liquid crystal molecules have positive dielectric constant anisotropy, that is, characteristics that the dielectric constant in the long axis direction of the liquid crystal molecules is larger than that in the short axis direction of the liquid crystal molecules. Thus, the liquid crystal molecules are arrayed in a direction vertical to a substrate face while the alignment direction of the liquid crystal molecules is sequentially rotated in a plane in parallel with the substrate face.

Meanwhile, attention is drawn to VA (Vertical Alignment) mode in which liquid crystal molecules are aligned vertical to a substrate face in a state that a voltage is not applied. In the VA mode, the liquid crystal molecules have negative dielectric constant anisotropy, that is, characteristics that the dielectric constant in the long axis direction of the liquid crystal molecules is smaller than that in the short axis direction of the liquid crystal molecules, and a wider view angle is able to be realized than TN mode.

In such a VA mode liquid crystal display, in the case where a voltage is applied, response is made so that the liquid crystal molecules aligned in the direction vertical to the substrate fall over in the direction in parallel with the substrate due to negative dielectric constant anisotropy, and thereby light is transmitted. However, the direction in which the liquid crystal molecules aligned in the direction vertical to the substrate fall is arbitrary. Thus, in the case where a voltage is applied, the alignment of the liquid crystal molecules is disarrayed, which causes deteriorated response characteristics to the voltage.

To improve the response characteristics, technologies to regulate the direction in which the liquid crystal molecules fall responsive to a voltage have been studied. Specific examples include a technology in which pretilt is given to the liquid crystal molecules by using an alignment film formed by radiating linear polarized light of ultraviolet or ultraviolet light from a direction diagonal to the substrate face (photo alignment film technology) and the like. As the photo alignment film technology, a technology in which an alignment film is formed by radiating linear polarized light of ultraviolet or ultraviolet light from a direction diagonal to the substrate face to a film including a polymer containing chalcone structure, and bridging a double bond section in the chalcone structure is known (refer to Patent literature 1 to Patent literature 3). Further, in addition, there is a technology in which an alignment film is formed by using a mixture of a vinylcinnamate derivative polymer and polyimide (refer to Patent literature 4). Further, a technology in which an alignment film is formed by radiating linear polarized light with a wavelength of 254 nm to a film containing polyimide and decomposing part of the polyimide (refer to Patent literature 5) and the like are known. Further, as a peripheral technology of the photo alignment film technology, there is a technology in which a liquid crystalline alignment film is formed by forming a film including a liquid crystalline polymer compound on a film including a polymer containing a dichroic photoreactive constituent unit such as an azobenzen derivative irradiated with linear polarized light or diagonal light (refer to Patent literature 6).

CITATION LIST

Patent Literature

PTL 1: Japanese Unexamined Patent Application Publication No. 10-087859
PTL 2: Japanese Unexamined Patent Application Publication No. 10-252646
PTL 3: Japanese Unexamined Patent Application Publication No. 2002-082336
PTL 4: Japanese Unexamined Patent Application Publication No. 10-232400
PTL 5: Japanese Unexamined Patent Application Publication No. 10-073821
PTL 6: Japanese Unexamined Patent Application Publication No. 11-326638

SUMMARY OF INVENTION

However, in the foregoing photo alignment film technology, though response characteristics are improved, there is a problem that a major light radiation equipment such as an equipment for radiating linear polarized light and an equipment for radiating light from the direction diagonal to the substrate face is necessitated in forming an alignment film. Further, there is a problem that for manufacturing a liquid crystal display having a multidomain in which a plurality of sub pixels are provided in a pixel to divide alignment of liquid crystal molecules in order to realize a wider view angle, a more major equipment is necessitated, and the manufacturing steps become complicated. Specifically, in the liquid crystal display having a multidomain, an alignment film is formed so that each pretilt varies according to every sub pixel. Thus, in the case where the foregoing photo alignment film technology is used in manufacturing the liquid crystal display having a multidomain, light is irradiated for every sub pixel. Accordingly, a mask pattern for every sub pixel is necessitated, resulting in a much more light radiation equipment.

In view of the foregoing problems, it is a first object of the present invention to provide a liquid crystal display unit including a liquid crystal display device with which response characteristics are able to be improved. Further, it is a second object of the present invention to provide a method of manufacturing a liquid crystal display unit with which response characteristics are able to be easily improved without using a major equipment.

A liquid crystal display unit according to a first aspect of the present invention to attain the foregoing first object includes a liquid crystal display device having a pair of alignment films provided on an opposed face side of a pair of substrates and a liquid crystal layer that is provided between the pair of alignment films and contains a liquid crystal molecule having negative dielectric constant anisotropy, wherein at least one of the pair of alignment films contains a compound (referred to as "compound after alignment process" for convenience) obtained by bridging a polymer compound having a crosslinkable functional group as a side chain, and the liquid crystal molecule is given with pretilt by the cross-linked compound ("compound after alignment"). Further, a liquid crystal display device according to a first aspect of the present invention to attain the foregoing first object includes the liquid crystal display device in the liquid crystal display unit according to the first aspect of the present invention. In this case, "crosslinkable functional group" means a group capable of forming a cross-linked structure (cross-linking structure).

A liquid crystal display unit according to a second aspect of the present invention to attain the foregoing first object includes a liquid crystal display device having a pair of alignment films provided on an opposed face side of a pair of substrates and a liquid crystal layer that is provided between the pair of alignment films and contains a liquid crystal molecule having negative dielectric constant anisotropy, wherein at least one of the pair of alignment films contains a compound (referred to as "compound after alignment process" for convenience) obtained by deforming a polymer compound having a photosensitive functional group as a side chain, and the liquid crystal molecule is given with pretilt by the deformed compound ("compound after alignment process"). Further, a liquid crystal display device according to a second aspect of the present invention to attain the foregoing first object includes the liquid crystal display device in the liquid crystal display unit according to the second aspect of the present invention. In this case, "photosensitive functional group" means a group capable of absorbing energy line.

A method of manufacturing a liquid crystal display unit (or a method of manufacturing a liquid crystal display device) according to a first aspect of the present invention to attain the foregoing second object includes the steps of: forming a first alignment film including a polymer compound (referred to as "compound before alignment process" for convenience) having a crosslinkable functional group as a side chain on one substrate of a pair of substrates; forming a second alignment film on the other substrate of the pair of substrates; arranging the pair of substrates so that the first alignment film and the second alignment film are opposed to each other, and sealing a liquid crystal layer containing a liquid crystal molecule having negative dielectric constant anisotropy between the first alignment film and the second alignment film; and bridging the polymer compound (compound before alignment process) to give pretilt to the liquid crystal molecule after sealing the liquid crystal layer.

In this case, in the method of manufacturing a liquid crystal display unit (or the method of manufacturing a liquid crystal display device) according to the first aspect of the present invention, it is possible that while predetermined electric field is applied to the liquid crystal layer to align the liquid crystal molecules, ultraviolet is irradiated to cross-link the side chain of the polymer compound ("compound before alignment process").

In this case, it is preferable that the ultraviolet is irradiated while applying electric field to the liquid crystal layer so that the liquid crystal molecules are aligned diagonal to the surface of at least one substrate of the pair of substrates. Further, it is preferable that the pair of substrates includes a substrate having a pixel electrode and a substrate having an opposed electrode, and the ultraviolet is irradiated from the substrate side having a pixel electrode. In general, a color filter is formed on the substrate side having an opposed electrode. There is a possibility that the ultraviolet is absorbed by the color filter and reaction of the crosslinkable functional group of the alignment film material is hardly generated. Thus, as described above, it is preferable that the ultraviolet is irradiated from the substrate side having a pixel electrode on which the color filter is not formed. In the case where the color filter is formed on the substrate side having a pixel electrode, it is preferable that the ultraviolet is irradiated from the substrate side having an opposed electrode. Fundamentally, the orientation angle (deviation angle) of the liquid crystal molecules to be provided with pretilt is determined by the direction of the electric field, and the polar angle (zenith angle) is determined by electric field intensity. The same is applied to the after-mentioned methods of manufacturing a liquid crystal display unit according to a second aspect and a third aspect of the present invention.

The method of manufacturing a liquid crystal display unit (or the method of manufacturing a liquid crystal display device) according to the second aspect of the present invention to attain the foregoing second object includes the steps of: forming a first alignment film including a polymer compound (referred to as "compound before alignment process" for convenience) having a photosensitive functional group as a side chain on one substrate of a pair of substrates; forming a second alignment film on the other substrate of the pair of substrates; arranging the pair of substrates so that the first alignment film and the second alignment film are opposed to each other, and sealing a liquid crystal layer containing a liquid crystal molecule having negative dielectric constant anisotropy between the first alignment film and the second alignment film; and deforming the polymer compound (compound before alignment process) to give pretilt to the liquid crystal molecule after sealing the liquid crystal layer.

In this case, in the method of manufacturing a liquid crystal display unit (or the method of manufacturing a liquid crystal display device) according to the second aspect of the present invention, it is possible that while predetermined electric field is applied to the liquid crystal layer to align the liquid crystal molecules, ultraviolet is irradiated to deform the side chain of the polymer compound (compound before alignment process).

The method of manufacturing a liquid crystal display unit (or the method of manufacturing a liquid crystal display device) according to the third aspect of the present invention to attain the foregoing second object includes the steps of: forming a first alignment film including a polymer compound (referred to as "compound before alignment process"

for convenience) having a crosslinkable functional group or a photosensitive functional group as a side chain on one substrate of a pair of substrates; forming a second alignment film on the other substrate of the pair of substrates; arranging the pair of substrates so that the first alignment film and the second alignment film are opposed to each other, and sealing a liquid crystal layer containing a liquid crystal molecule having negative dielectric constant anisotropy between the first alignment film and the second alignment film; and radiating energy line to the polymer compound (compound before alignment process) to give pretilt to the liquid crystal molecule after sealing the liquid crystal layer. In this case, examples of energy line include ultraviolet, X ray, and electron ray.

In this case, in the method of manufacturing a liquid crystal display unit (or the method of manufacturing a liquid crystal display device) according to the third aspect of the present invention, it is possible that while predetermined electric field is applied to the liquid crystal layer to align the liquid crystal molecules, ultraviolet as energy line is irradiated to the polymer compound.

In some cases, the liquid crystal display unit according to the first aspect of the present invention or the method of manufacturing a liquid crystal display unit according to the first aspect of the present invention including the foregoing preferred mode is hereinafter collectively and simply referred to as "first aspect of the present invention." In some cases, the liquid crystal display unit according to the second aspect of the present invention or the method of manufacturing a liquid crystal display unit according to the second aspect of the present invention including the foregoing preferred mode is hereinafter collectively and simply referred to as "second aspect of the present invention." In some cases, the method of manufacturing a liquid crystal display unit according to the third aspect of the present invention including the foregoing preferred mode is hereinafter collectively and simply referred to as "third aspect of the present invention."

In the first aspect, the second aspect, or the third aspect of the present invention, the polymer compound (compound before alignment process) or the compound (compound after alignment process) composing at least one of the pair of alignment films may include a compound having a group expressed by Formula (1) as a side chain. Such a structure is referred to as "1A structure of the present invention, 2A structure of the present invention, and 3A structure of the present invention" for convenience.

$$-R_1-R_2-R_3 \tag{1}$$

In the formula, R1 represents a straight chain or branched chain bivalent organic group with the carbon number of 3 or more, and is bonded to a main chain of the polymer compound or the cross-linked compound (the compound before alignment process or the compound after alignment process); R2 represents a bivalent organic group containing a plurality of ring structures, and one of atoms composing the ring structures is bonded to R1; and R3 represents a hydrogen atom, a halogen atom, an alkyl group, an alkoxy group, and a monovalent group having a carbonate group, or a derivative thereof.

Otherwise, in the first aspect, the second aspect, or the third aspect of the present invention, the polymer compound (compound before alignment process) or the compound (compound after alignment process) composing at least one of the pair of alignment films may include a compound having a group expressed by Formula (2) as a side chain. Such a structure is referred to as "1B structure of the present invention, 2B structure of the present invention, and 3B structure of the present invention" for convenience.

$$-R_{11}-R_{12}-R_{13}-R_{14} \tag{2}$$

In the formula, R11 represents a straight chain or branched chain bivalent organic group with the carbon number from 1 to 20 both inclusive, preferably from 3 to 12 both inclusive that may contain an ether group or an ester group, and is bonded to a main chain of the polymer compound or the cross-linked compound (the compound before alignment process or the compound after alignment process), or R11 represents an ether group or an ester group and is bonded to the main chain of the polymer compound or the cross-linked compound (the compound before alignment process or the compound after alignment process); R12 represents, for example, a bivalent group containing one structure of chalcone, cinnamate, cinnamoyl, coumarin, maleimide, benzophenone, norbornene, orizanol, and chitosan, or an ethynylene group; R13 represents a bivalent organic group containing a plurality of ring structures; and R14 represents a hydrogen atom, a halogen atom, an alkyl group, an alkoxy group, and a monovalent group having a carbonate group or a derivative thereof.

Otherwise, in the first aspect of the present invention, the compound (compound after alignment process) obtained by bridging the polymer compound (compound before alignment process) includes a side chain and a main chain supporting the side chain to the substrate. The side chain is bonded to the main chain, and includes a cross-linked section in which part of the side chain is cross-linked and an end structure section bonded to the cross-linked section. The liquid crystal molecule is located along the end structure section or is sandwiched between the end structure sections, and thereby the liquid crystal molecule is given with pretilt. Otherwise, in the second aspect of the present invention, the compound (compound after alignment process) obtained by deforming the polymer compound (compound before alignment process) includes a side chain and a main chain supporting the side chain to the substrate. The side chain is bonded to the main chain, and includes a deformed section in which part of the side chain is deformed and an end structure section bonded to the deformed section. The liquid crystal molecule is located along the end structure section or is sandwiched between the end structure sections, and thereby the liquid crystal molecule is given with pretilt. Otherwise, in the third aspect of the present invention, the compound obtained by radiating energy line to the polymer compound includes a side chain and a main chain supporting the side chain to the substrate. The side chain is bonded to the main chain, and includes a cross-linked/deformed section in which part of the side chain is cross-linked/deformed and an end structure section bonded to the cross-linked/deformed section. The liquid crystal molecule is located along the end structure section or is sandwiched between the end structure sections, and thereby the liquid crystal molecule is given with pretilt. Such a structure is referred to as "1C structure of the present invention, 2C structure of the present invention, and 3C structure of the present invention" for convenience. In the 1C structure of the present invention, the 2C structure of the present invention, and the 3C structure of the present invention, the end structure section may have a mesogenic group.

Otherwise, in the first aspect of the present invention, the compound (compound after alignment process) obtained by bridging the polymer compound (compound before alignment process) includes a side chain and a main chain supporting the side chain to the substrate. The side chain is bonded to the main chain, and includes a cross-linked section in which part of the side chain is cross-linked and an end structure section that is bonded to the cross-linked section and has a mesogenic group. Such a structure is referred to as "1D structure of the present invention for convenience. Further, in the 1D structure of the present invention, it is possible that the main chain is bonded to the cross-linked section by covalent bond, and the cross-linked section is bonded to the end structure section by covalent bond. Otherwise, in the second aspect of the present invention, the compound (compound after alignment process) obtained by deforming the polymer compound (compound before alignment process) includes a side chain and a main chain supporting the side chain to the substrate. The side chain is bonded to the main chain, and includes a deformed section in which part of the side chain is deformed and an end structure section that is bonded to the deformed section and has a mesogenic group. Such a structure is referred to as "2D structure of the present invention for convenience. Otherwise, in the third aspect of the present invention, the compound (compound after alignment process) obtained by radiating energy line to the polymer compound (compound before alignment process) includes a side chain and a main chain supporting the side chain to the substrate. The side chain is bonded to the main chain, and includes a cross-linked/deformed section in which part of the side chain is cross-linked/deformed and an end structure section that is bonded to the cross-linked/deformed section and has a mesogenic group. Such a structure is referred to as "3D structure of the present invention for convenience.

In the first aspect of the present invention including the 1A structure to the 1D structure of the present invention, the side chain (more specifically, the cross-linked section) may have a photodimerization photosensitive group.

Further, in the first aspect to the third aspect of the present invention including the preferred structures and preferred modes described above, it is possible that a surface roughness Ra of the first alignment film is 1 nm or less, or at least one of the pair of alignment films has the surface roughness Ra of 1 nm or less. Such a structure is referred to as "1E structure of the present invention, 2E structure of the present invention, and 3E structure of the present invention" for convenience. The surface roughness Ra is specified in JIS B 0601:2001.

Further, in the first aspect to the third aspect of the present invention including the preferred structures and preferred modes described above, it is possible that the second alignment film includes the polymer compound (compound before alignment process) composing the first alignment film, or the pair of alignment films has the same composition. However, as long as the polymer compound (compound before alignment process) specified in the first aspect to the third aspect of the present invention is contained, the pair of alignment films may have each composition different from each other, or the second alignment film may include a polymer compound (compound before alignment process) different from a polymer compound (compound before alignment process) composing the first alignment film.

Further, in the first aspect to the third aspect of the present invention including the preferred structures and preferred modes described above, it is possible that an alignment regulation section including a slit formed in an electrode or a projection provided in the substrate is provided.

In the first aspect to the third aspect of the present invention including the preferred structures and preferred modes described above, the main chain may contain imide bond in a repeat unit. Further, the polymer compound (compound after alignment process) may include a structure to align the liquid crystal molecules in a predetermined direction in relation to the pair of substrates. Further, the pair of substrates may include a substrate having a pixel electrode and a substrate having an opposed electrode.

In the liquid crystal display unit according to the first aspect of the present invention, at least one of the pair of alignment films contains the compound obtained by bridging the polymer compound having a crosslinkable functional group as a side chain. Thus, the cross-linked compound gives pretilt to the liquid crystal molecules. Thus, in the case where electric field is applied between the pixel electrode and the opposed electrode, the liquid crystal molecules respond so that the long axis direction thereof becomes a predetermined direction in relation to the substrate face, and favorable display characteristics are secured. In addition, the cross-linked compound gives pretilt to the liquid crystal molecules. Thus, compared to a case that pretilt is not given to the liquid crystal molecules, response rate according to electric field between the electrodes becomes increased. Compared to a case that pretilt is given without using the cross-linked compound, favorable display characteristics are easily retained.

In the method of manufacturing a liquid crystal display unit according to the first aspect of the present invention, after the first alignment film containing the polymer compound having a crosslinkable functional group as a side chain is formed, the liquid crystal layer is sealed between the first alignment film and the second alignment film. In this case, the entire liquid crystal molecules in the liquid crystal layer are aligned in a predetermined direction (for example, horizontal direction, vertical direction, or diagonal direction) in relation to the surface of the first alignment film and the second alignment film by the first alignment film and the second alignment film. Next, the polymer compound is cross-linked by reacting the crosslinkable functional group while applying electric field. Thereby, pretilt is able to be given to the liquid crystal molecules in the vicinity of the cross-linked compound. That is, pretilt is able to be given to the liquid crystal molecules by bridging the polymer compound in a state that the liquid crystal molecules are aligned without radiating straight polarized light or diagonal light to the alignment film before sealing the liquid crystal layer or without using a major equipment. Thus, response rate is more improved compared to a case that pretilt is not given to the liquid crystal molecules.

In the liquid crystal display unit according to the second aspect of the present invention, at least one of the pair of alignment films contains the compound obtained by deforming the polymer compound having a photosensitive functional group as a side chain. Thus, the deformed compound gives pretilt to the liquid crystal molecules. Thus, in the case where an electric field is applied between the pixel electrode and the opposed electrode, the liquid crystal molecules respond so that the long axis direction thereof becomes a predetermined direction in relation to the substrate face, and favorable display characteristics are secured. In addition, the cross-linked compound gives pretilt to the liquid crystal molecules. Thus, compared to a case that pretilt is not given to the liquid crystal molecules, response rate according to electric field between the electrodes becomes increased. Compared to a case that pretilt is given without using the deformed compound, favorable display characteristics are easily retained.

In the method of manufacturing a liquid crystal display unit according to the second aspect of the present invention, after the first alignment film containing the polymer compound having a photosensitive functional group as a side chain is formed, the liquid crystal layer is sealed between the first alignment film and the second alignment film. In this case, the entire liquid crystal molecules in the liquid crystal layer are aligned in a predetermined direction (for example, horizontal direction, vertical direction, or diagonal direction) in relation to the surface of the first alignment film and the second alignment film by the first alignment film and the second alignment film. Next, the polymer compound is deformed while applying electric field. Thereby, pretilt is able to be given to the liquid crystal molecules in the vicinity of the deformed compound. That is, pretilt is able to be given to the liquid crystal molecules by deforming the polymer compound in a state that the liquid crystal molecules are aligned without radiating straight polarized light or diagonal light to the alignment film before sealing the liquid crystal layer or without using a major equipment. Thus, response rate is more improved compared to a case that pretilt is not given to the liquid crystal molecules.

In the method of manufacturing a liquid crystal display unit according to the third aspect of the present invention, pretilt is given to the liquid crystal molecules by radiating energy line to the polymer compound (compound before alignment process). That is, pretilt is able to be given to the liquid crystal molecules by bridging or deforming the side chain of the polymer compound in a state that the liquid crystal molecules are aligned without radiating straight polarized light or diagonal light to the alignment film before sealing the liquid crystal layer or without using a major equipment. Thus, response rate is more improved compared to a case that pretilt is not given to the liquid crystal molecules.

BRIEF DESCRIPTION OF DRAWINGS

FIG. 16 is a conceptual diagram for explaining a relation between a deformed polymer compound and a liquid crystal molecule.

DESCRIPTION OF EMBODIMENTS

A description will be given of the present invention based on embodiments of the present invention and examples with reference to the drawings. However, the present invention is not limited to the embodiments of the present invention and the examples, but various numerical values and materials in the embodiments of the present invention and the examples are shown as exemplifications. The description will be given as the following order.

1. [Description of common compositions and common structures in liquid crystal display units of the present invention]
2. [Description of liquid crystal display units and methods of manufacturing the same of the present invention based on embodiments of the present invention]
3. [Description of liquid crystal display units and methods of manufacturing the same of the present invention based on examples and the like]

[Description of Common Compositions and Common Structures in Liquid Crystal Display Units (Liquid Crystal Display Devices) of the Present Invention]

Figure 1:
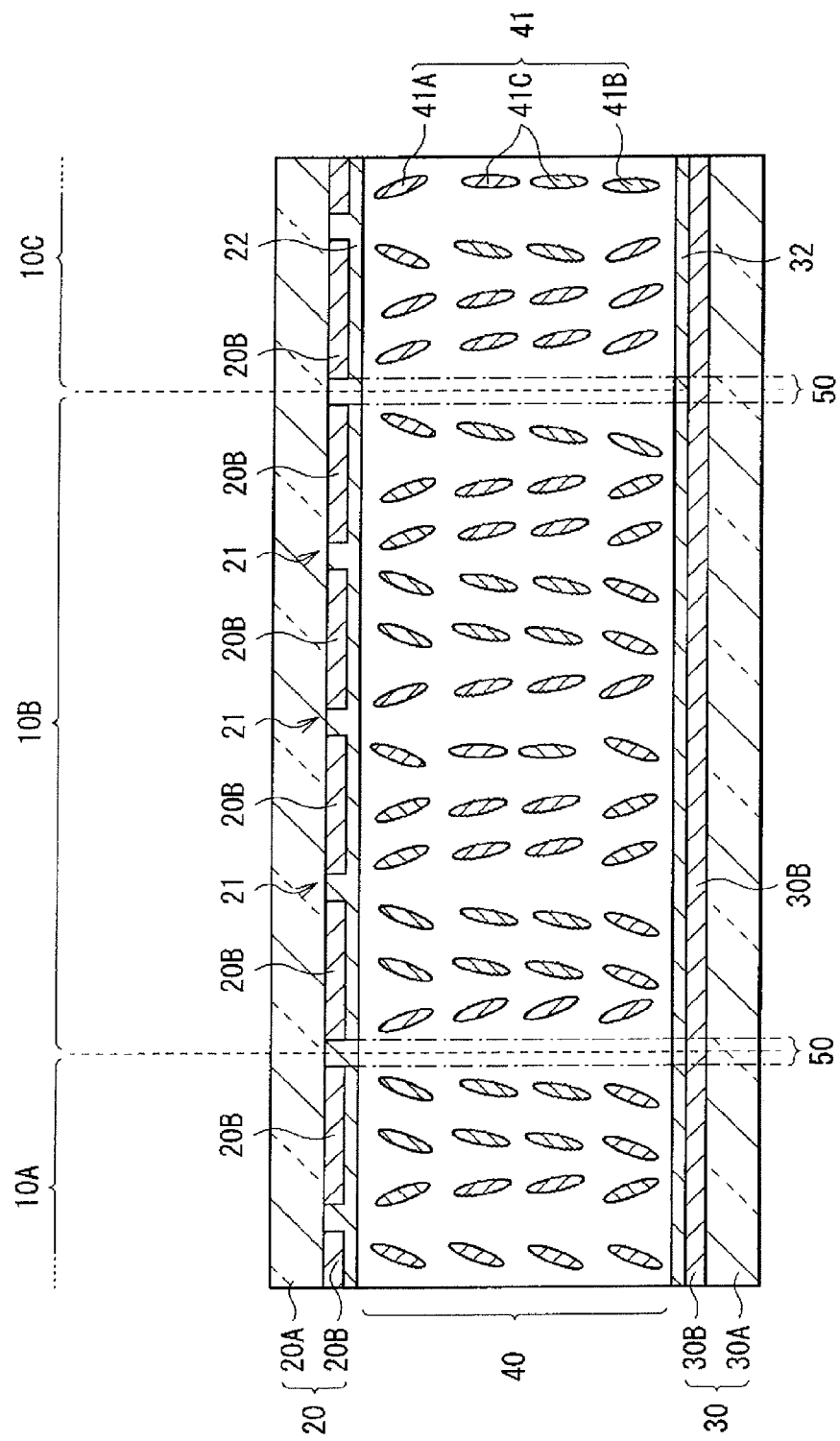
FIG. 1 is a schematic partial cross sectional view of a liquid crystal display unit of the present invention.

FIG. 1 illustrates a schematic partial cross sectional view of liquid crystal display units (or liquid crystal display devices) according to a first aspect to a third aspect of the present invention. The liquid crystal display unit has a plurality of pixels 10 (10A, 10B, 10C and the like). In the liquid crystal display unit (liquid crystal display device), a liquid crystal layer 40 containing a liquid crystal molecule 41 is provided between a TFT (Thin Film Transistor) substrate 20 and a CF (Color Filter) substrate 30 with alignment films 22 and 32 in between. The liquid crystal display unit (liquid crystal display device) is a so-called transmissive liquid crystal display unit, and the display mode thereof is vertical alignment (VA) mode. FIG. 1 illustrates non-driving state in which a drive voltage is not applied.

In the TFT substrate 20, a plurality of pixel electrodes 20B are arranged, for example, in a state of matrix on the surface on the side opposed to the CF substrate 30 of a glass substrate 20A. Further, a TFT switching device including a gate, a source, a drain and the like that respectively drive the plurality of pixel electrodes 20B and a gate line, a source line and the like (not illustrated) connected to the TFT switching device are provided thereon. The pixel electrode 20B is provided for every pixel that is electrically separated by a pixel separating section 50 on the glass substrate 20A. For example, the pixel electrode 20B is made of a material having transparency such as ITO (indium tin oxide). The pixel electrode 20B is provided with a slit section 21 (section where the electrode is not formed) having a stripe-like or V-shaped pattern in each pixel. Thereby, in the case where a drive voltage is applied, electric field diagonal to the long axis direction of the liquid crystal molecule 41 is given, a region where alignment direction is different is formed in each pixel (alignment division), and thus view angle characteristics are improved. That is, the slit section 21 is an alignment regulation section for regulating alignment of the entire liquid crystal molecules 41 in the liquid crystal layer 40 in order to secure favorable display characteristics. In this case, alignment direction of the liquid crystal molecule 41 in the case where a drive voltage is applied is regulated by the slit section 21. As described above, fundamentally, direction angle of the liquid crystal molecules in the case where pretilt is given is determined by electric field direction, and the electric field direction is determined by the alignment regulation section.

In the CF substrate 30, a color filter (not illustrated) including, for example, red (R), green (G), and blue (B) stripe-like filters and an opposed electrode 30B are arranged over the almost whole area of an effective display region on the face opposed to the TFT substrate 20 of the glass substrate 30A. As the pixel electrode 20B is, the opposed electrode 30B is made of a material having transparency such as ITO.

The alignment film 22 is provided on the surface on the liquid crystal layer 40 side of the TFT substrate 20 to cover the pixel electrode 20B and the slit section 21. The alignment film 32 is provided on the surface on the liquid crystal layer 40 side of the CF substrate 30 to cover the opposed electrode 30B. The alignment films 22 and 32 regulate alignment of the liquid crystal molecules 41. In this case, the alignment films 22 and 32 have a function to align the liquid crystal molecules 41 in the direction vertical to the substrate face and to give pretilt to the liquid crystal molecules 41 (41A and 41B) in the vicinity of the substrate. In the liquid crystal display unit (liquid crystal display device) illustrated in FIG. 1, a slit section is not provided on the side of the CF substrate 30.

Figure 8:
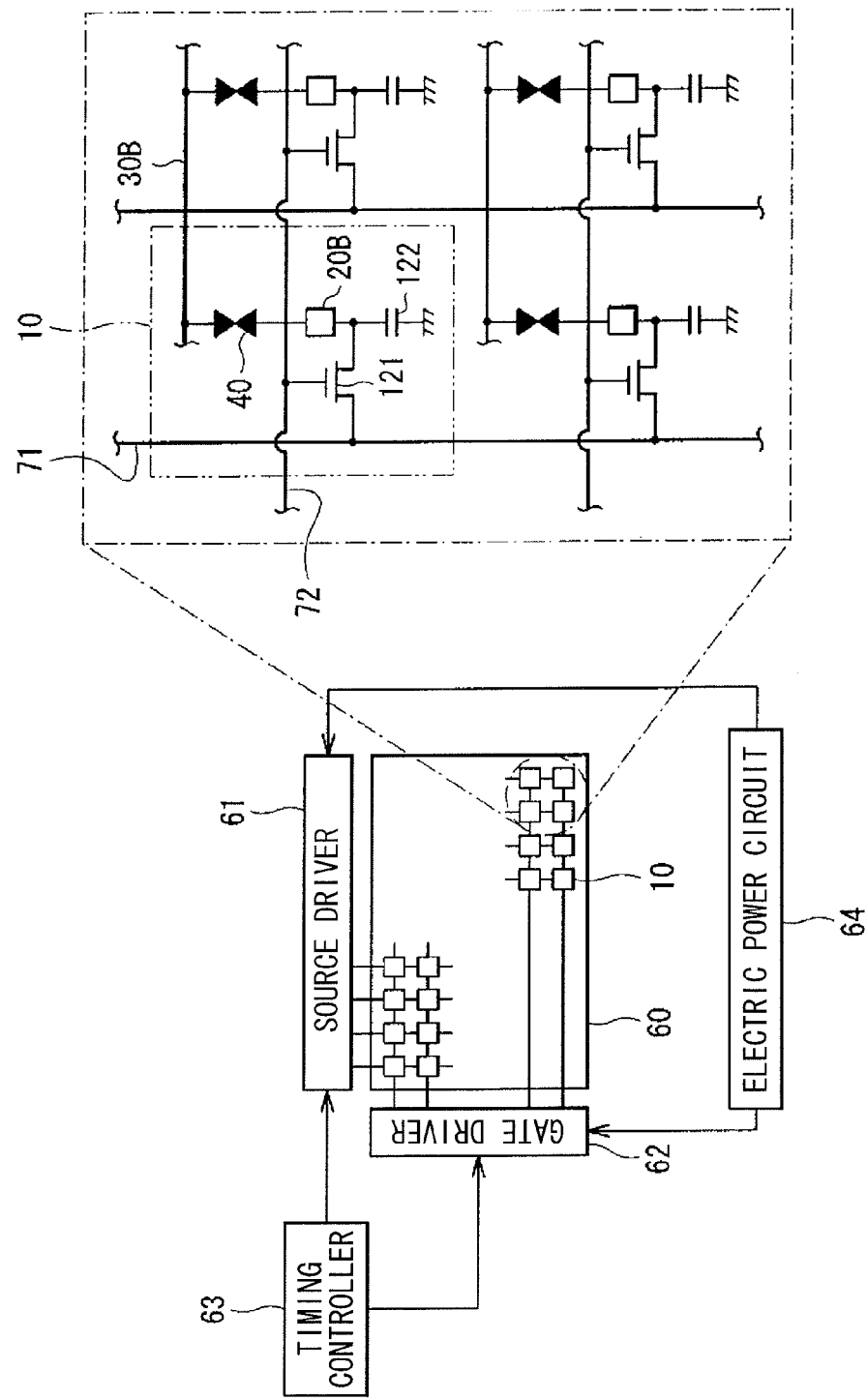
FIG. 8 is a circuit structural diagram of the liquid crystal display unit illustrated in FIG. 1.

FIG. 8 illustrates a circuit structure of the liquid crystal display unit illustrated in FIG. 1.

As illustrated in FIG. 8, the liquid crystal display unit includes a liquid crystal display device having the plurality of pixels 10 provided in a display region 60. In the liquid crystal display unit, around the display region 60, a source driver 61, a gate driver 62, a timing controller 63 for controlling the source driver 61 and the gate driver 62, and an electric power circuit 64 for supplying electric power to the source driver 61 and the gate driver 62 are provided.

The display region 60 is a region where a picture is displayed, and is a region where a picture is able to be displayed by arranging the plurality of pixels 10 in a state of matrix. FIG. 8 illustrates the display region 60 including the plurality of pixels 10, and separately illustrates an enlarged region corresponding to four pixels 10.

In the display region 60, a plurality of source lines 71 are arranged in rows, and a plurality of gate lines 72 are arranged in columns, and the pixel 10 is arranged in an intersection of the source line 71 and the gate line 72. The respective pixels 10 include a transistor 121 and a capacitor 122 together with the pixel electrode 20B and the liquid crystal layer 40. In the respective transistors 121, the source electrode is connected to the source line 71, the gate electrode is connected to the gate line 72, and the drain electrode is connected to the capacitor 122 and the pixel electrode 20B. The respective source lines 71 are connected to the source driver 61, and an image signal is supplied from the source drive 61. The respective gate lines 72 are connected to the gate driver 62, and a scanning signal is sequentially supplied from the gate driver 62.

The source driver 61 and the gate driver 62 select a specific pixel 10 out of the plurality of pixels 10.

The timing controller 63 outputs, for example, an image signal (for example, respective RGB picture signals corresponding to red, green, and blue) and a source driver control signal for controlling operation of the source driver 61 to the source driver 61. Further, the timing controller 63 outputs, for example, a gate driver control signal for controlling operation of the gate driver 62 to the gate driver 62. Examples of the source driver control signal include a horizontal synchronization signal, a start pulse signal, a clock signal for the source driver and the like. Examples of the gate driver control signal include a vertical synchronization signal and a clock signal for the gate driver and the like.

In the liquid crystal display unit, a drive voltage is applied between the pixel electrode 20B and the opposed electrode 30B by the following procedure and thereby a picture is displayed. Specifically, in the case where a source driver control signal is inputted from the timing controller 63, the source driver 61 individually supplies an image signal to a predetermined source line 71 based on an image signal inputted similarly from the timing controller 63. At the same time, in the case where a gate driver control signal is inputted from the timing controller 63, the gate driver 62 sequentially supplies a scanning signal to the gate line 72 at a predetermined timing. Thereby, the pixel 10 located in the intersection of the source line 71 supplied with the image signal and the gate line 72 supplied with the scanning signal is selected, and a drive voltage is applied to the pixel 10.

A description will be hereinafter given of the present invention based on the embodiments (referred to as "embodiment" for short) and the examples.

First Embodiment

A first embodiment relates to the VA mode liquid crystal display unit (or liquid crystal display device) according to the first aspect of the present invention, and methods of manufacturing a liquid crystal display units (or liquid crystal display devices) according to the first aspect of the present invention and the third aspect of the present invention. In the first embodiment, the alignment films 22 and 32 contain one or more polymer compounds having a cross-linking structure in a side chain (compound after alignment process). Liquid crystal molecules are given with pretilt by the cross-linked compound. In this case, the compound after alignment process is generated by forming the alignment films 22 and 32 containing one or more polymer compounds (compound before alignment process) having a main chain and a side chain, providing the liquid crystal layer 40, and then bridging the polymer compound; or radiating energy line to the polymer compound; or more specifically, by reacting a crosslinkable functional group contained in the side chain while applying electric field or magnetic field. The compound after alignment process contains a structure in which the liquid crystal molecules are arranged in a predetermined direction (specifically diagonal direction) to the pair of substrates (specifically, the TFT substrate 20 and the CF substrate 30). As described above, by bridging the polymer compound, or by radiating energy line to the polymer compound, the compound after alignment process is contained in the alignment films 22 and 32. Thereby, the liquid crystal molecules 41 in the vicinity of the alignment films 22 and 32 are able to be given with pretilt. Accordingly, the response rate becomes increased, and the display characteristics are improved.

The compound before alignment process preferably contains a structure with high heat resistivity as a main chain. Thereby, in the liquid crystal display unit (liquid crystal display device), even if the liquid crystal display unit (liquid crystal display device) is exposed under high temperature environment, the compound after alignment process in the alignment films 22 and 32 retains alignment regulation ability for the liquid crystal molecules 41. In the result, response characteristics and display characteristics such as contrast are favorably retained, and reliability is secured. In this case, the main chain preferably contains imide bond in a repeat unit. Examples of compounds before alignment process containing imide bond in the main chain include a polymer compound containing a polyimide structure expressed by Formula (3). The polymer compound containing the polyimide structure shown in Formula (3) may include one of the polyimide structures shown in Formula (3), may contain various types of the polyimide structures that are randomly linked, or may contain other structure in addition to the structure shown in Formula (3).

structure by photoreaction is preferable, since thereby the liquid crystal display unit (liquid crystal display device) in which alignment of the liquid crystal molecule 41 is easily regulated in a predetermined direction, response characteristics are improved, and favorable display characteristics are shown is able to be easily manufactured.

Examples of the photoreactive crosslinkable functional group (photosensitive group having photosensitivity such as a photodimerization photosensitive group) include a group containing one structure of chalcone, cinnamate, cinnamoyl, coumarin, maleimide, benzophenone, norbornene, orizanol, and chitosan. Out of the foregoing, examples of group containing the structure of chalcone, cinnamate, or cinnamoyl include a group expressed by Formula (41). In the case where a compound before alignment process having a side chain containing the group shown in Formula (41) is cross-linked, for example, a structure shown in Formula (42) is formed. That is, the compound after alignment process generated from the polymer compound containing the group shown in Formula (41) contains the structure shown in Formula (42) having cyclobutane skeleton. For example, in some cases, the photoreactive crosslinkable functional group such as maleimide shows polymerization reaction in addition to photodimerization reaction. Thus, "crosslinkable functional group" includes not only a crosslinkable functional group showing photodimerization reaction but also a crosslinkable functional group showing polymerization reaction. In other words, in the present invention, concept of "cross-link" includes not only photodimerization reaction but also polymerization reaction.

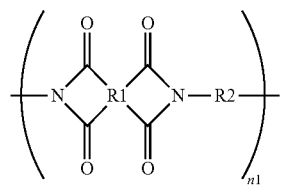
(3)

In the formula, R1 represents a tetravalent organic group, R2 represents a bivalent organic group, and n1 represents an integer number of 1 or more.

R1 and R2 in Formula (3) are arbitrary as long as R1 and R2 are a tetravalent or bivalent group containing carbon. One of R1 and R2 preferably contains a crosslinkable functional group as a side chain. Thereby, in the compound after alignment process, sufficient alignment regulation ability is easily obtained.

Further, in the compound before alignment process, a plurality of side chains are bonded to a main chain. It is enough that at least one of the plurality of side chains contains a crosslinkable functional group. That is, the compound before alignment process may contain a side chain not showing crosslinkable characteristics in addition to the side chain having crosslinkable characteristics. The number of types of the side chains containing a crosslinkable functional group may be one or plural number. The crosslinkable functional group is arbitrary as long as the crosslinkable functional group is a functional group that is crosslinkable after the liquid crystal layer 40 is formed. The crosslinkable functional group may be a group that forms a cross-linking structure by photoreaction, or may be a group that forms a cross-linking structure by heat reaction. Specially, a photoreactive crosslinkable functional group (photosensitive group having photosensitivity) that forms a cross-linking

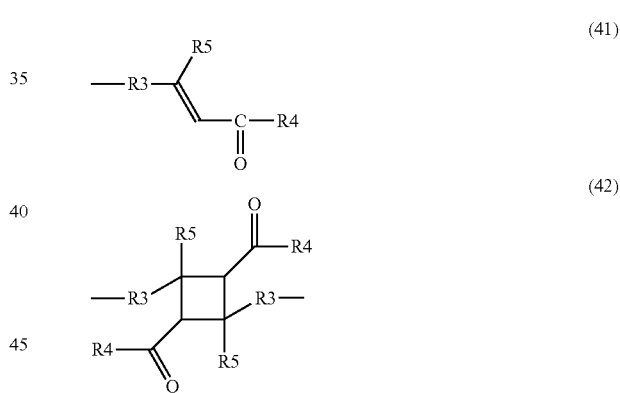

In the formula, R3 represents a bivalent group containing an aromatic ring, R4 represents a monovalent group containing 1 or more ring structures, and R5 represents a hydrogen atom, an alkyl group, or a derivative thereof.

R3 in Formula (41) is arbitrary as long as R3 is a bivalent group containing an aromatic ring such as benzene ring, which may contain a carbonyl group, ether bond, ester bond, or a hydrocarbon group in addition to the aromatic ring. Further, R4 in Formula (41) is arbitrary as long as R4 is a monovalent group containing 1 or more ring structures, which may contain a carbonyl group, ether bond, ester bond, a hydrocarbon group, a halogen atom or the like in addition to the ring structure. The ring structure contained in R4 is arbitrary as long as the ring contains carbon as an element composing a skeleton. Examples of the ring structure include an aromatic ring, a heterocyclic ring, an aliphatic ring, and a ring structure obtained by linking or condensing them. R5 in Formula (41) is arbitrary as long as R5 is a hydrogen atom, an alkyl group, or a derivative thereof. In this case, "derivative" means a group obtained by substituting a substitution group such as a halogen atom for part or all of hydrogen atoms contained in the alkyl group. Further, the carbon number of the alkyl group introduced as R5 is arbitrary. As R5, a hydrogen atom or a methyl group is preferable, since thereby favorable cross-linking reactivity is obtained.

Each R3 in Formula (42) may be identical with each other, or different from each other. The same is applied to each R4 and each R5 in Formula (41). Examples of R3, R4, and R5 in Formula (42) include substances similar to the foregoing R3, R4, and R5 in Formula (41).

Examples of the group shown in Formula (41) include groups expressed by Formula (41-1) to Formula (41-27). However, the group shown in Formula (41) is not limited to the groups shown in Formula (41-1) to Formula (41-27), as long as a group has the structure shown in Formula (41).

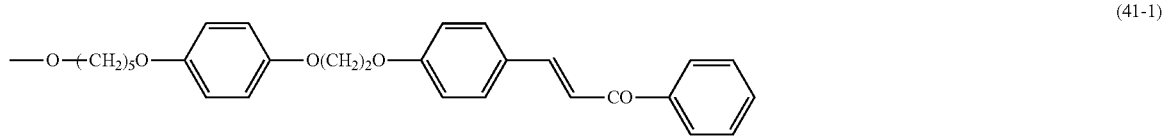
(41-1)

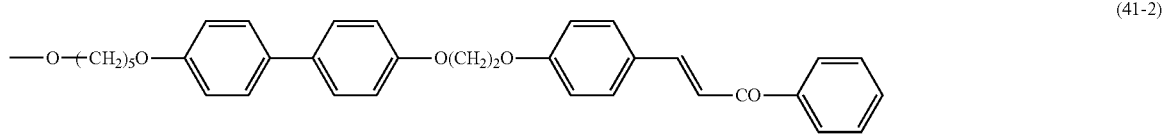
(41-2)

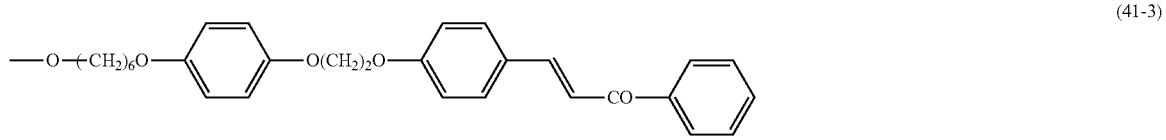
(41-3)

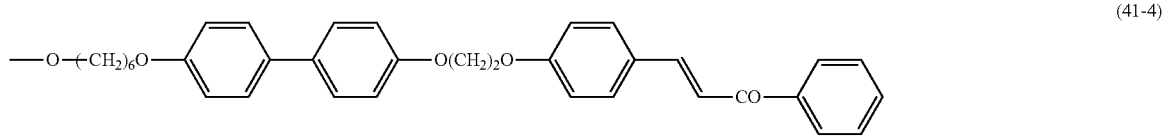
(41-4)

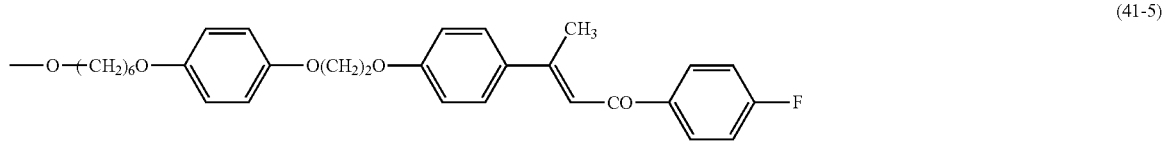
(41-5)

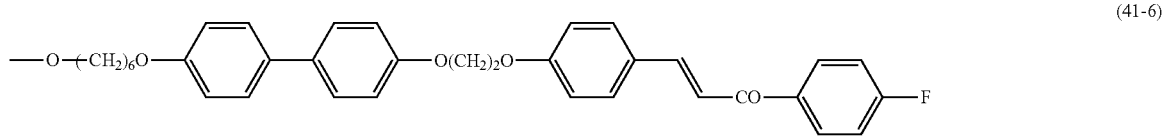
(41-6)

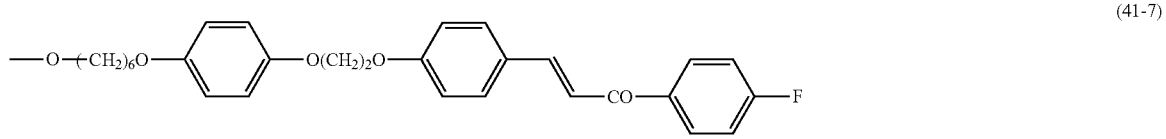
(41-7)

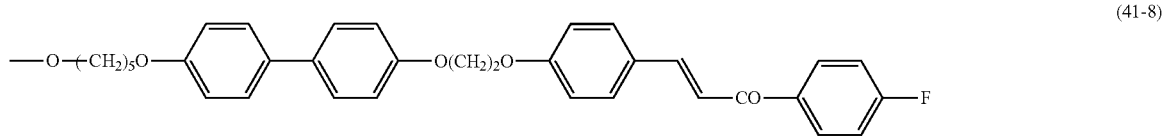
(41-8)

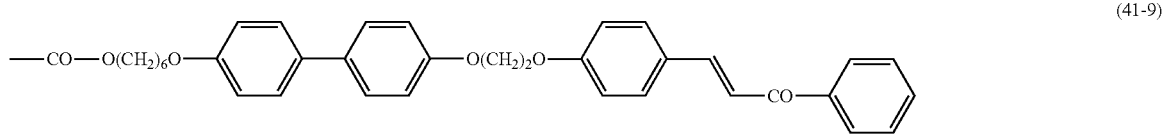
(41-9)

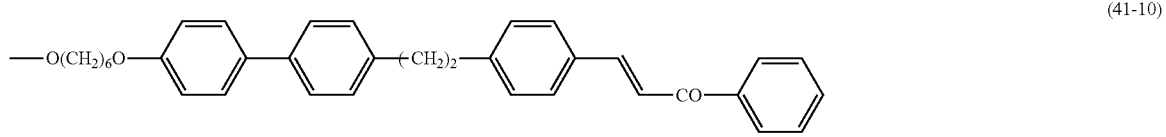
(41-10)

-continued
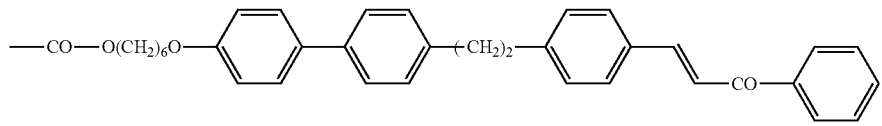
(41-11)
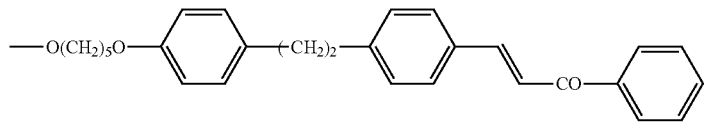
(41-12)
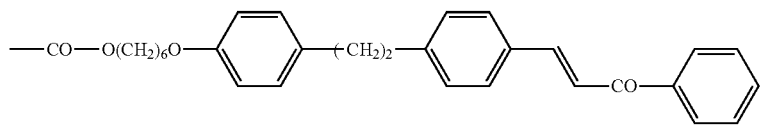
(41-13)
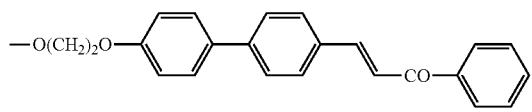
(41-14)
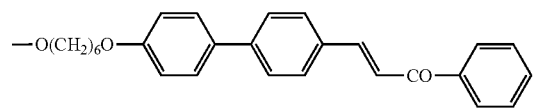
(41-15)
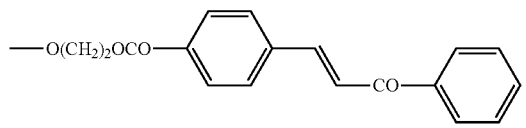
(41-16)
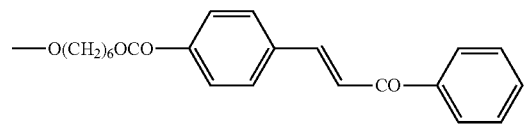
(41-17)
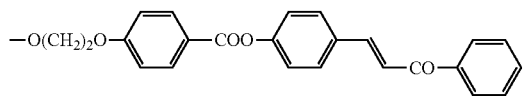
(41-18)
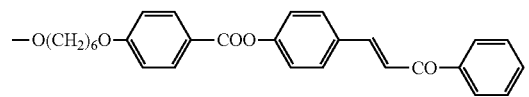
(41-19)
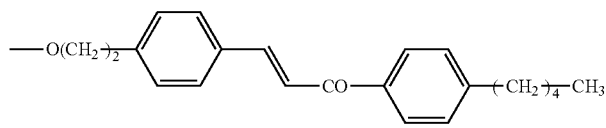
(41-20)
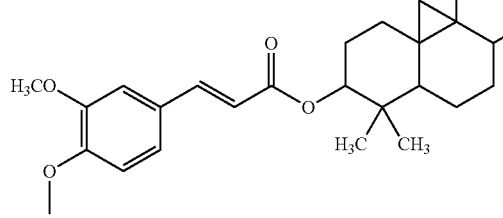
(41-21)

-continued
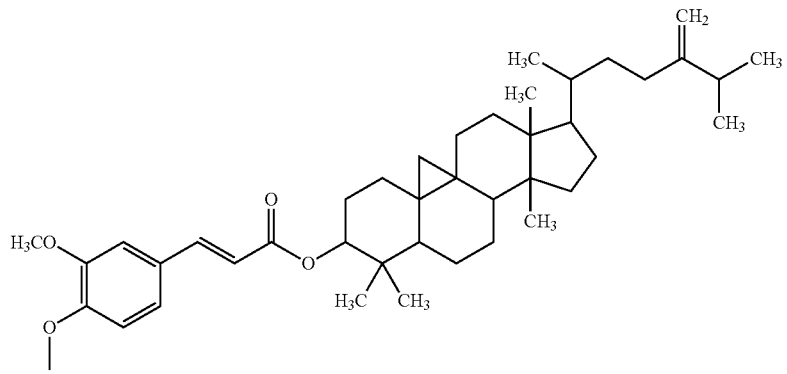
(41-22)
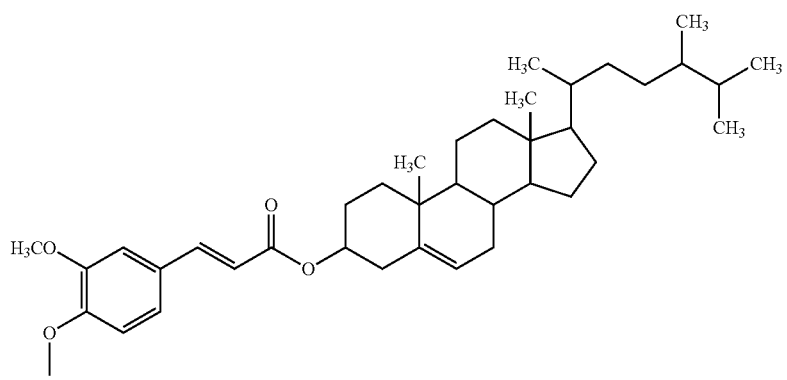
(41-23)
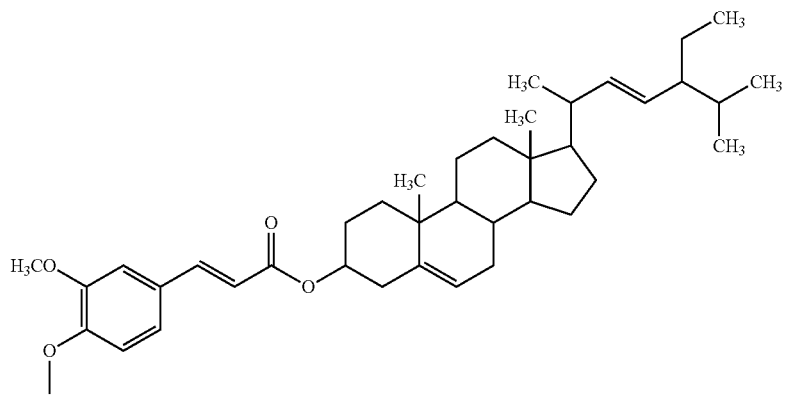
(41-24)
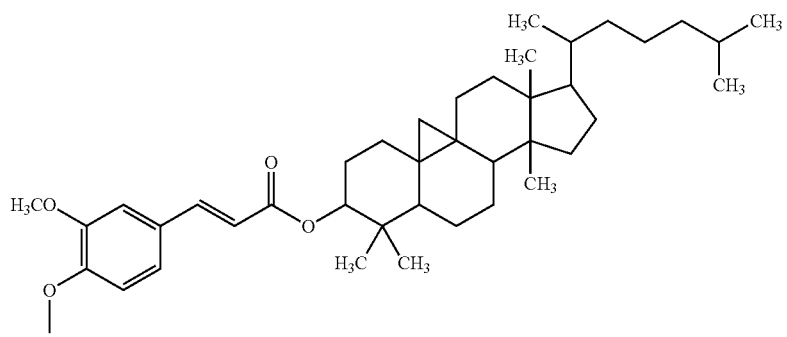
(41-25)

-continued (41-26)
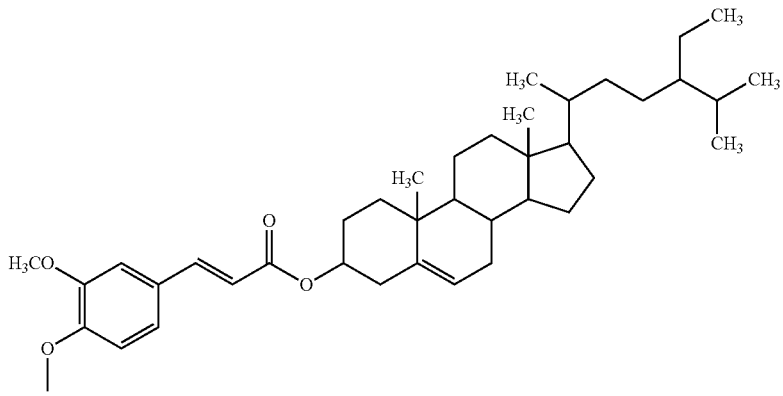

(41-27)
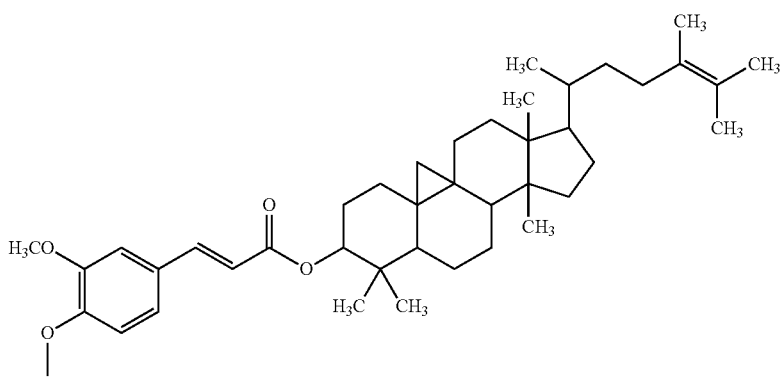

The compound before alignment process preferably contains a structure for aligning the liquid crystal molecules 41 in a direction vertical to the substrate face (hereinafter referred to as "vertical alignment induction structure section"). Thereby, even if the alignment films 22 and 32 do not contain a compound having a vertical alignment induction structure section (so-called a general vertical aligner) in addition to the compound after alignment process, alignment regulation of the entire liquid crystal molecules 41 is enabled. In addition, the alignment films 22 and 32 capable of more uniformly demonstrating the alignment regulation function for the liquid crystal layer 40 are more easily formed than in a case that the compound having a vertical alignment induction structure section is separately contained. The vertical alignment induction structure section may be contained in a main chain, a side chain, or both thereof in the compound before alignment process. Further, in the case where the compound before alignment process contains the polyimide structure shown in the foregoing Formula (3), two types of structures that are a structure containing a vertical alignment induction structure section (repeat unit) as R2 and a structure containing a crosslinkable functional group (repeat unit) as R2 are preferably contained, since it is easily available. In the case where the vertical alignment induction structure section is contained in the compound before alignment process, the vertical alignment induction structure section is also contained in the compound after alignment process.

Examples of the vertical alignment induction structure section include an alkyl group with the carbon number of 10 or more, a halogenated alkyl group with the carbon number of 10 or more, an alkoxy group with the carbon number of 10 or more, a halogenated alkoxy group with the carbon number of 10 or more, and an organic group containing a ring structure. Specific examples include structures expressed by Formula (5-1) to Formula (5-6) as a structure containing a vertical alignment induction structure section.

(5-1)
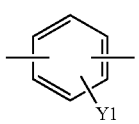

(5-2)
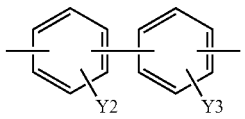

(5-3)
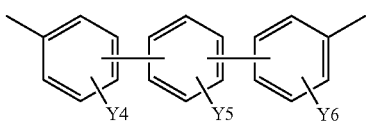

(5-4)
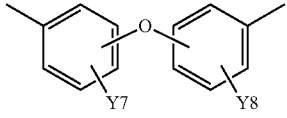

(5-5)
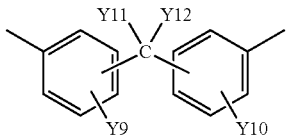

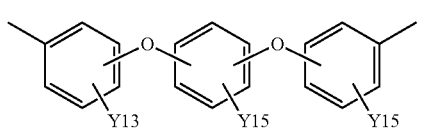
(5-6)

In the formulas, Y1 represents an alkyl group with the carbon number of 10 or more, an alkoxy group with the carbon number of 10 or more, or a monovalent organic group containing a ring structure. Further, Y2 to Y15 represent a hydrogen atom, an alkyl group with the carbon number of 10 or more, an alkoxy group with the carbon number of 10 or more, or a monovalent organic group containing a ring structure. At least one of Y2 and Y3, at least one of Y4 to Y6, at least one of Y7 and Y8, at least one of Y9 to Y12, and at least one of Y13 to Y15 are an alkyl group with the carbon number of 10 or more, an alkoxy group with the carbon number of 10 or more, or a monovalent organic group containing a ring structure. However, Y11 and Y12 may be bonded to each other to form a ring structure.

Examples of the monovalent organic group containing a ring structure as a vertical alignment induction structure section include groups expressed by Formula (6-1) to Formula (6-23). Further, examples of the bivalent organic group containing a ring structure as a vertical alignment induction structure section include groups expressed by Formula (7-1) to Formula (7-7).

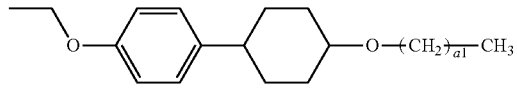
(6-1)

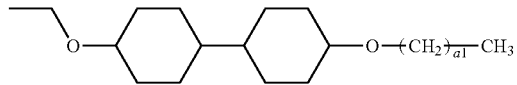
(6-2)

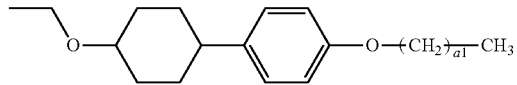
(6-3)

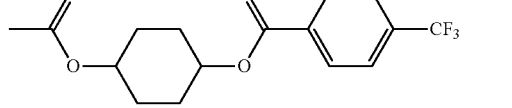
(6-4)

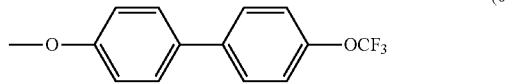
(6-5)

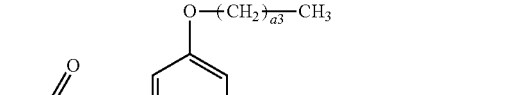
(6-6)

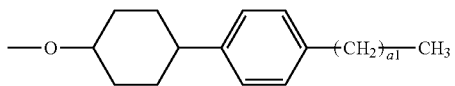
(6-7)

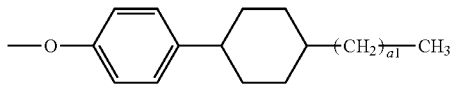
(6-8)

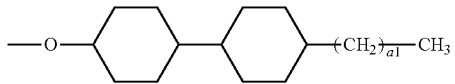
(6-9)

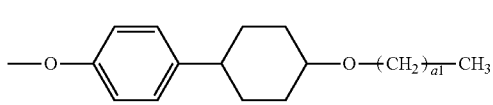
(6-10)

(6-11)

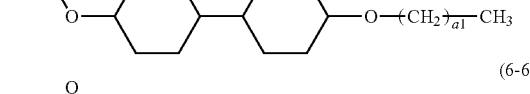
(6-12)

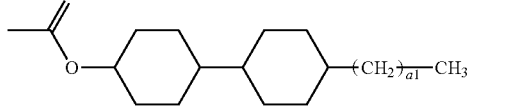
(6-13)

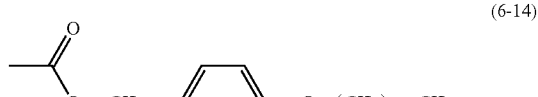
(6-14)

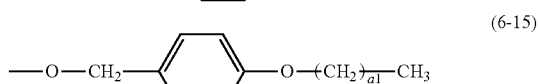
(6-15)

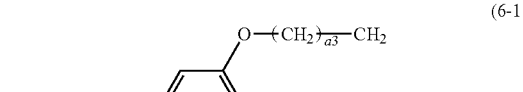
(6-16)

In the formulas, a1 to a3 represent an integer number from 0 to 21 both inclusive.

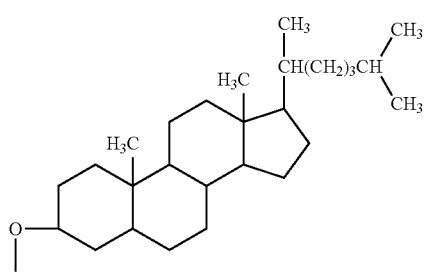
(6-17)

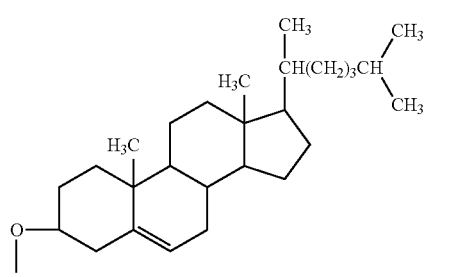
(6-18)
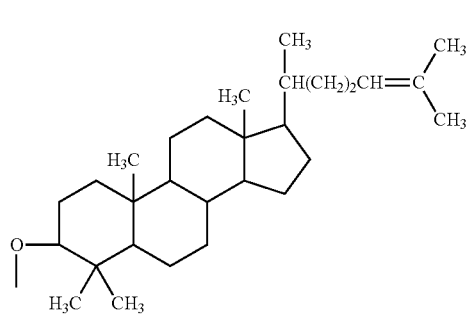
(6-19)
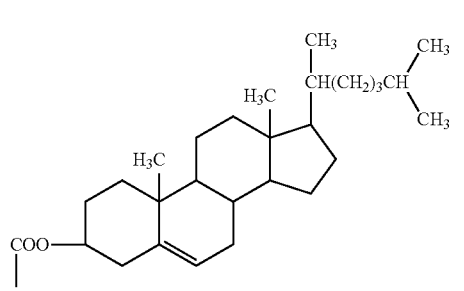
(6-20)
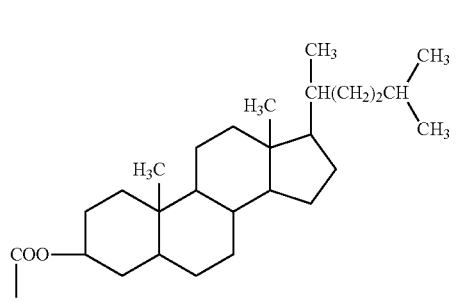
(6-21)
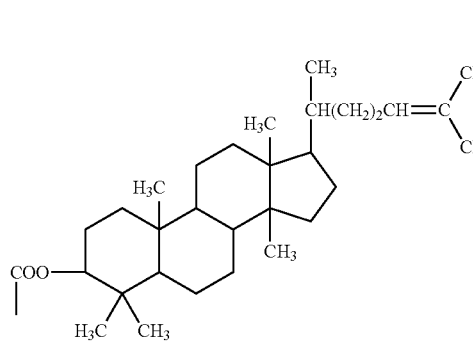
(6-22)
(6-23)
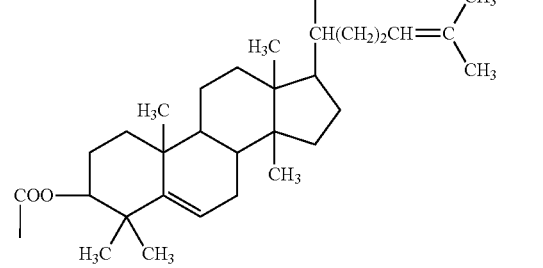
(7-1)
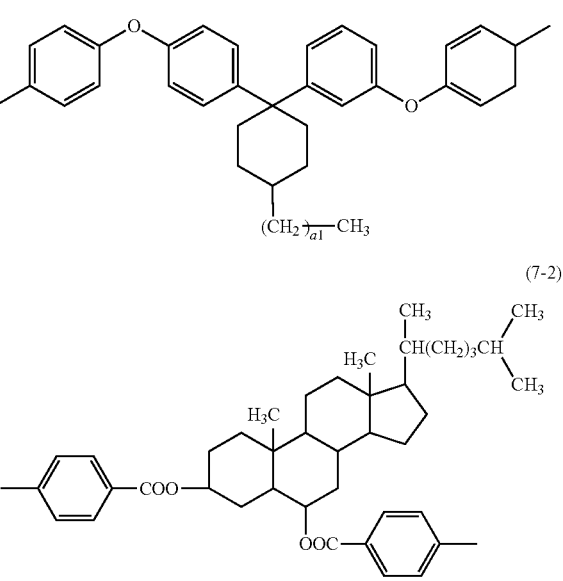
(7-2)
(7-3)
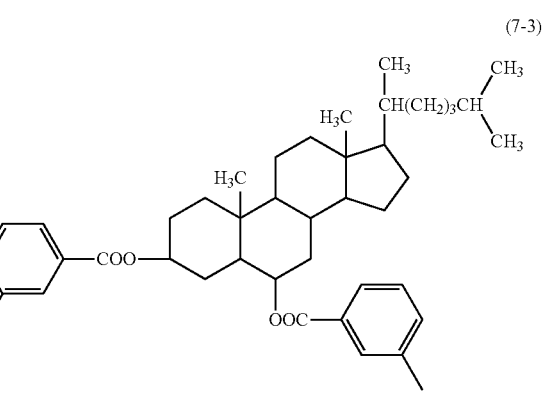
(7-4)
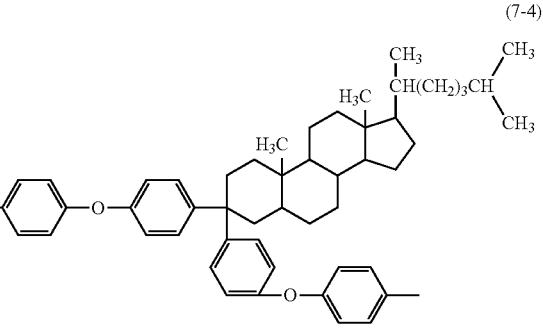

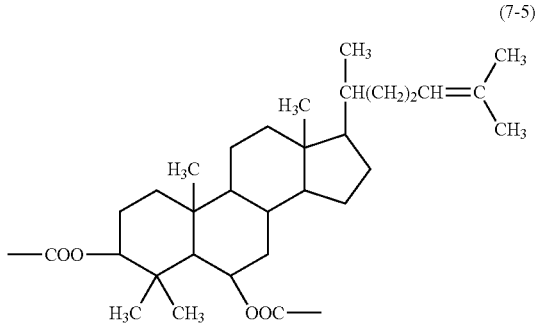

(7-5)

In the formulas, a1 represents an integer number from 0 to 21 both inclusive.

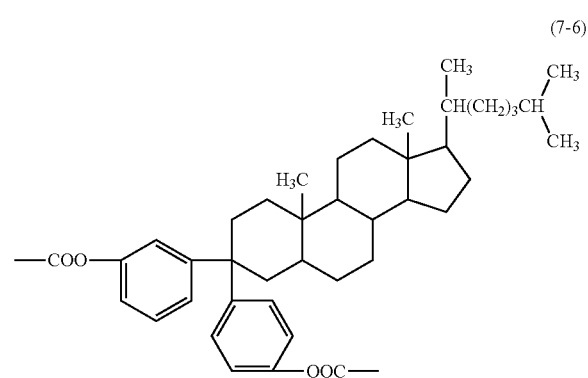

(7-6)

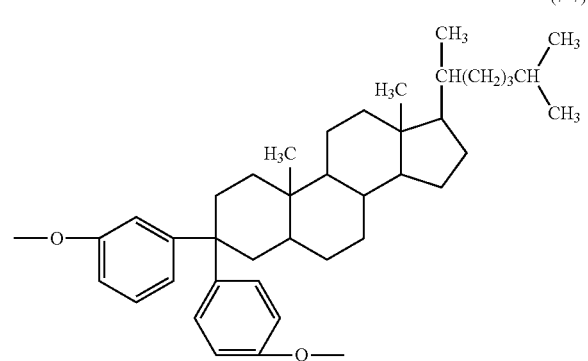

(7-7)

The vertical alignment induction structure section is not limited to the foregoing groups as long as a structure functioning to align the liquid crystal molecules 41 in the direction vertical to the substrate face is contained.

Further, according to a 1A structure and a 2A structure (refer to a sixth embodiment described later) or a 3A structure of the present invention, the polymer compound before cross-link (compound before alignment process) includes a compound having a group expressed by Formula (1) as a side chain in addition to a crosslinkable functional group. The group shown in Formula (1) is able to move along the liquid crystal molecules 41, and thus in bridging the compound before alignment process, the group shown in Formula (1) is fixed together with the crosslinkable functional group in a state that the group shown in Formula (1) is located along the alignment direction of the liquid crystal molecules 41. Due to the fixed group shown in Formula (1), the alignment direction of the liquid crystal molecules 41 is able to be more easily regulated in a predetermined direction. Therefore, manufacturing the liquid crystal display device having favorable display characteristics is able to be more facilitated.

$$-R1-R2-R3 \qquad (1)$$

In the formula, R1 represents a straight chain or branched chain bivalent organic group with the carbon number of 3 or more, and is bonded to a main chain of the polymer compound before cross-link (compound before alignment process). R2 represents a bivalent organic group containing a plurality of ring structures, and one of atoms composing the ring structures is bonded to R1. R3 represents a hydrogen atom, a halogen atom, an alkyl group, an alkoxy group, and a monovalent group having a carbonate group, or a derivative thereof.

R1 in Formula (1) is a region functioning as a spacer section to fix R2 and R3 on the main chain and to make R2 and R3 easily and freely move along the liquid crystal molecules 41. Examples of R1 include an alkylene group and the like. The alkylene group may have ether bond between each intermediate carbon atom. The number of places having the ether bond may be one or more. Further, R1 may have a carbonyl group or a carbonate group. The carbon number of R1 is more preferably 6 or more. Thereby, the group shown in Formula (1) interacts with the liquid crystal molecules 41, and thus R2 and R3 become easily located along the liquid crystal molecules 41. The carbon number is preferably determined so that the length of R1 becomes approximately equal to the length of the end chain of the liquid crystal molecules 41.

R2 in Formula (1) is a section along a ring structure (core region) contained in a general nematic liquid crystal molecule. Examples of R2 include a group or a skeleton similar to a ring structure contained in a liquid crystal molecule such as an 1,4-phenylene group, an 1,4-cyclohexylene group, a pyrimidine-2,5-diyl group, an 1,6-naphthalene group, and a bivalent group having a steroid skeleton or a derivative thereof. In this case, "derivative" means a group obtained by introducing one or more substitution groups into the foregoing series of groups.

R3 in Formula (1) is a section along the end chain of a liquid crystal molecule. Examples of R3 include an alkylene group and an alkylene halide group. In the alkylene halide group, it is enough that at least one hydrogen atom out of the alkylene group is substituted by a halogen atom, and the halogen atom type is arbitrary. The alkylene group or the alkylene halide group may have ether bond between each intermediate carbon atom. The number of places having the ether bond may be one or more. Further, R3 may have a carbonyl group or a carbonate group. The carbon number of R3 is more preferably 6 or more for a reason similar to that of R1.

Specific examples include a monovalent group expressed by Formula (1-1) to Formula (1-8) as the group shown in Formula (1).

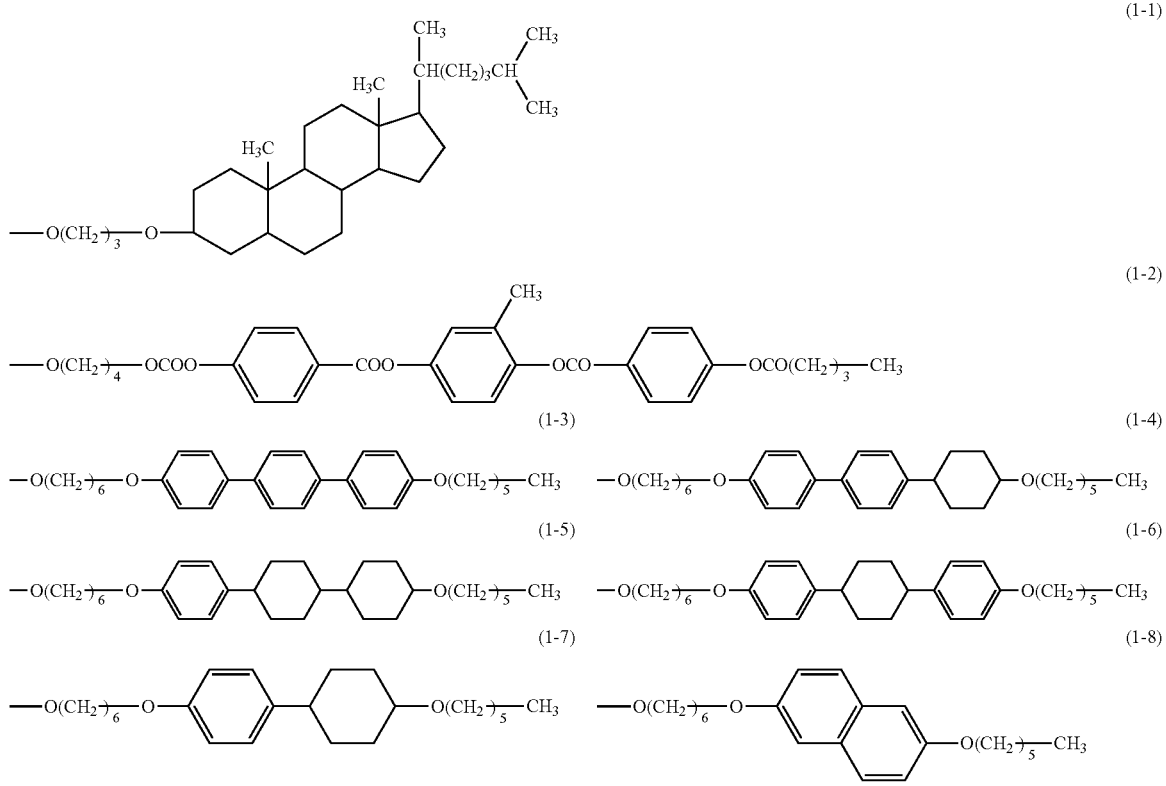

However, the group shown in Formula (1) is not limited to the foregoing groups, as long as a group is able to move along the liquid crystal molecules 41.

Otherwise, according to a 1B structure and a 2B structure (refer to the sixth embodiment described later) or a 3B structure of the present invention, the polymer compound before cross-link (compound before alignment process) includes a compound having a group expressed by Formula (2) as a side chain. A region along the liquid crystal molecules 41 and a freely movable region are contained in addition to a crosslinkable region, fixation is enabled in a state that the region of the side chain is located more along the liquid crystal molecules 41. Thereby, the alignment of the liquid crystal molecules 41 is able to be more easily regulated in a predetermined direction. Therefore, manufacturing the liquid crystal display device having favorable display characteristics is able to be more facilitated.

$$-R11-R12-R13-R14 \quad (2)$$

In the formula, R11 represents a straight chain or branched chain bivalent organic group with the carbon number of 1 to 20 both inclusive or preferably 3 to 12 both inclusive that may contain an ether group or an ester group, and is bonded to a main chain of a polymer compound or a cross-linked compound (compound before alignment process or compound after alignment process). Otherwise, R11 represents an ether group or an ester group, and is bonded to a main chain of a polymer compound or a cross-linked compound (compound before alignment process or compound after alignment process). R12 represents a bivalent group containing one structure of chalcone, cinnamate, cinnamoyl, coumarin, maleimide, benzophenone, norbornene, orizanol, and chitosan, or an ethynylene group. R13 represents a bivalent organic group containing a plurality of ring structures. R14 represents a hydrogen atom, a halogen atom, an alkyl group, an alkoxy group, and a monovalent group having a carbonate group, or a derivative thereof.

R11 in Formula (2) is a region capable of freely moving in the compound before alignment process, and preferably has flexibility in the compound before alignment process. Examples of R11 include the group described for R1 in Formula (1). In the group shown in Formula (2), R12 to R14 are easily moved centering on R11 as an axis, and thus R13 and R14 are easily located along the liquid crystal molecules 41. The carbon number of R11 is more preferably from 6 to 10 both inclusive.

R12 in Formula (2) is a region having a crosslinkable functional group. As described above, the crosslinkable functional group may be a group that forms a cross-linking structure by photoreaction, or may be a group that forms a cross-linking structure by heat reaction. Specific examples of R12 include a bivalent group containing one structure of chalcone, cinnamate, cinnamoyl, coumarin, maleimide, benzophenone, norbornene, orizanol, and chitosan, or an ethynylene group.

R13 in Formula (2) is a region capable of being located along the core region of the liquid crystal molecule 41. Examples of R13 include the groups described for R2 in Formula (1).

R14 in Formula (2) is a region being located along the end chain of the liquid crystal molecule 41. Examples of R14 include the groups described for R3 in Formula (1).

Specific examples of the group shown in Formula (2) include monovalent groups expressed by Formula (2-1) to Formula (2-7).

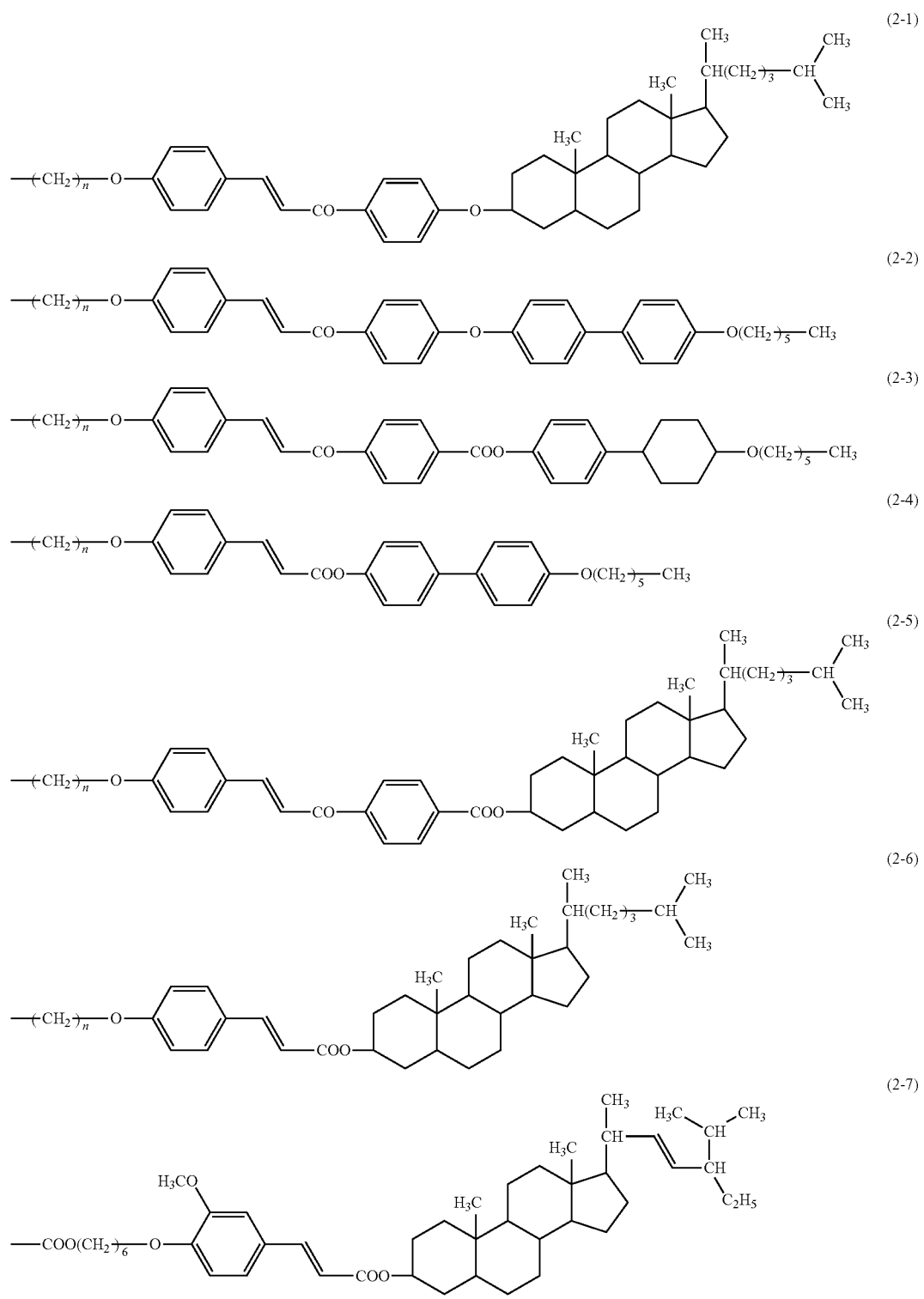

In the formula, n represents an integer number from 3 to 20 both inclusive.

However, the group shown in Formula (2) is not limited to the foregoing groups, as long as the foregoing four regions (R11 to R14) are contained.

Otherwise, according to a 1C structure of the present invention, the compound (compound after alignment process) obtained by bridging the polymer compound (compound before alignment process) includes a side chain and a main chain supporting the side chain to the substrate. The side chain is bonded to the main chain, and includes a cross-linked section in which part of the side chain is cross-linked and an end structure section bonded to the cross-linked section. In the case where the liquid crystal molecule is located along the end structure section or is sandwiched by the end structure sections, the liquid crystal molecule is given with pretilt. Further, according to a 2C structure of the present invention (refer to the sixth embodiment described later), the compound (compound after alignment process) obtained by deforming the polymer compound (compound before alignment process) includes a side chain and a main chain supporting the side chain to the substrate. The side chain is bonded to the main chain, and includes a deformed section in which part of the side chain is deformed and an end structure section bonded to the deformed section. In the case where the liquid crystal molecule is located along the end structure section or is sandwiched by the end structure sections, the liquid crystal molecule is given with pretilt. Further, according to a 3C structure of the present invention, the compound obtained by radiating energy line to the polymer compound includes a side chain and a main chain supporting the side chain to the substrate. The side chain is bonded to the main chain, and includes a cross-linked/deformed section in which part of the side chain is cross-linked or deformed and an end structure section bonded to the cross-linked/deformed section. In the case where the liquid crystal molecule is located along the end structure section or is sandwiched by the end structure sections, the liquid crystal molecule is given with pretilt.

Figure 15:
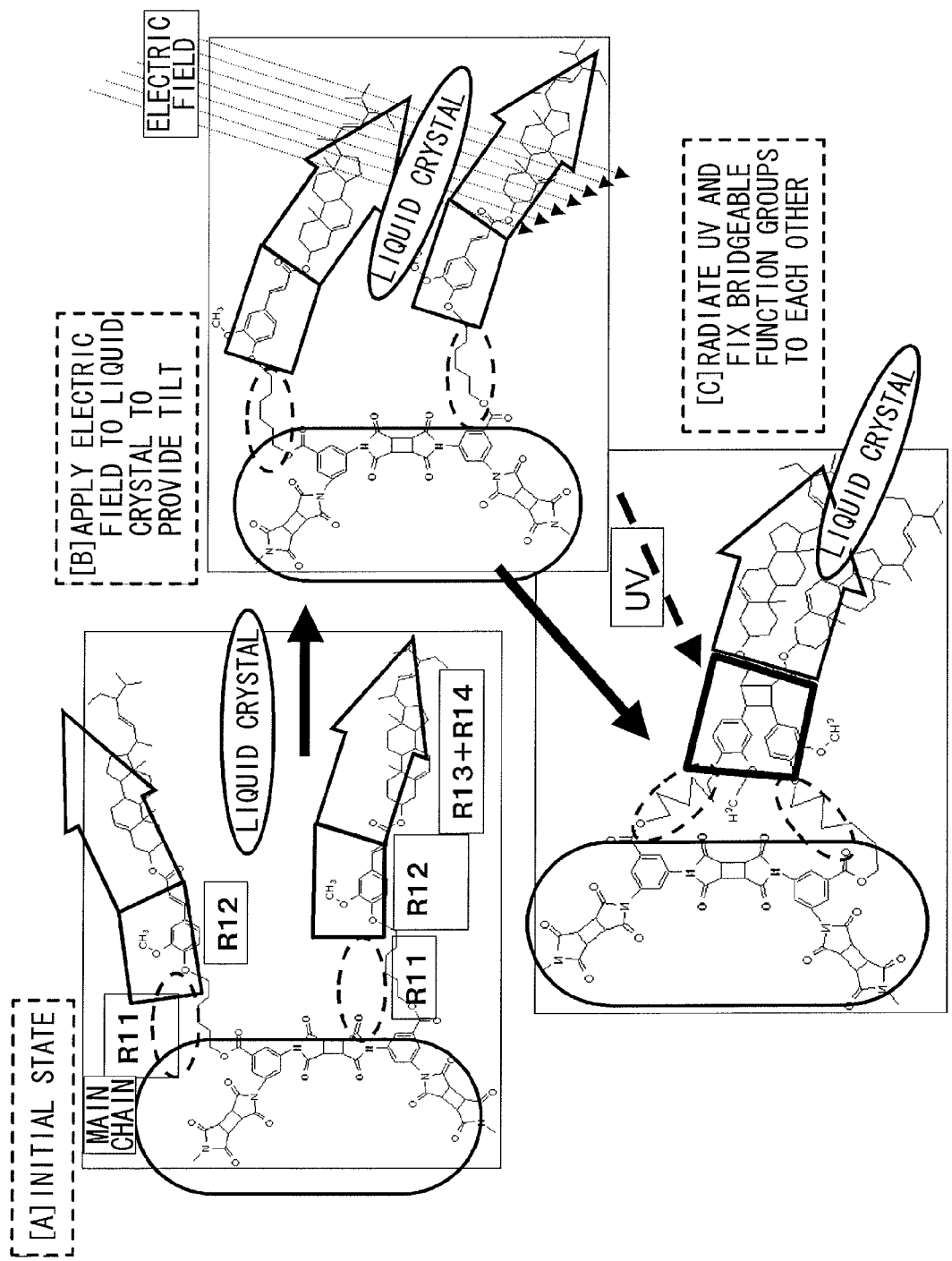
FIG. 15 is a conceptual diagram for explaining a relation between a cross-linked polymer compound and a liquid crystal molecule.

In the 1C structure of the present invention, the cross-linked section in which part of the side chain is cross-linked corresponds to R12 (after cross-link) in Formula (2). Further, the end structure section corresponds to R13 and R14 in Formula (2). In this case, in the compound after alignment process, for example, the crosslinkable sections in two side chains extending from the main chain are cross-linked, part of the liquid crystal molecule is sandwiched between the end structure section extending from one cross-linked section and the end structure section extending from the other cross-linked section, and the end structure section is fixed in a state that a predetermined angle exists between the end structure section and the substrate. In the result, the liquid crystal molecule is given with pretilt. Such a state is illustrated in the conceptual diagram of FIG. 15.

Otherwise, according to a 1D structure of the present invention, the compound (compound after alignment process) obtained by bridging the polymer compound (compound before alignment process) includes a side chain and a main chain supporting the side chain to the substrate. The side chain is bonded to the main chain, and includes a cross-linked section in which part of the side chain is cross-linked and an end structure section that is bonded to the cross-linked section and has a mesogenic group. In this case, the side chain may have a photodimerization photosensitive group. The main chain may be bonded to the bride section by covalent bond, and the cross-linked section may be bonded to the end structure section by covalent bond. Further, according to a 2D structure of the present invention (refer to the sixth embodiment described later), the compound (compound after alignment process) obtained by deforming the polymer compound (compound before alignment process) includes side chain and a main chain supporting the side chain to the substrate. The side chain is bonded to the main chain, and includes a deformed section in which part of the side chain is deformed and an end structure section that is bonded to the deformed section and has a mesogenic group. Further, according to a 3D structure of the present invention, the compound (compound after alignment process) obtained by radiating energy line to the polymer compound (compound before alignment process) includes a side chain and a main chain supporting the side chain to the substrate. The side chain is bonded to the main chain, and includes a cross-linked/deformed section in which part of the side chain is cross-linked or deformed, and an end structure section that is bonded to the cross-linked/deformed section and has a mesogenic group.

In the 1D structure of the present invention, examples of the photodimerization photosensitive group as a crosslinkable functional group (photosensitive functional group) include, as described above, a group containing one structure of chalcone, cinnamate, cinnamoyl, coumarin, maleimide, benzophenone, norbornene, orizanol, and chitosan. Further, it is possible that an adamant mesogenic group composing an end structure section expresses liquid crystal characteristics as a side chain or does not express liquid crystal characteristics. Specific examples of the structure include a steroid derivative, a cholesterol derivative, biphenyl, triphenyl, and naphthalene and the like. Further, examples of the end structure section include R13 and R14 in Formula (2).

Further, according to a 1E structure and a 2E structure (refer to the sixth embodiment described later) or a 3E structure of the present invention, the surface roughness Ra of a first alignment film (or an alignment film including the compound after alignment process) is 1 nm or less.

The compound after alignment process may contain an unreacted crosslinkable functional group. However, if reaction is initiated during drive, alignment of the liquid crystal molecules 41 may be disturbed. Thus, the portion of the unreacted crosslinkable functional group is preferably small. Whether or not the compound after alignment process contains the unreacted crosslinkable functional group is able to be checked by disassembling the liquid crystal display unit and analyzing the alignment films 22 and 32 by a transmissive type or reflection type FT-IR (Fourier transform infrared spectrophotometer). Specifically, first, the liquid crystal display unit is disassembled, and the surface of the alignment films 22 and 32 is washed with an organic solvent or the like. After that, the alignment films 22 and 32 are analyzed by FT-IR. For example, in the case where a double bond forming the cross-linking structure shown in Formula (41) remains in the alignment films 22 and 32, absorbing spectrum originated from the double bond is obtained, and thereby it is able to be confirm that the compound after alignment process contains the unreacted crosslinkable functional group.

Further, the alignment films 22 and 32 may contain other vertical aligner in addition to the foregoing polymer compound after alignment process. Examples of other vertical aligner include polyimide having a vertical alignment induction structure section and polysiloxane having a vertical alignment induction structure section and the like.

The liquid crystal layer 40 contains the liquid crystal molecules 41 having negative dielectric constant anisotropy. The liquid crystal molecules 41 have a rotationally-symmetrical shape centering on the long axis and the short axis that are perpendicular to each other, and have negative dielectric constant anisotropy.

Figure 2:
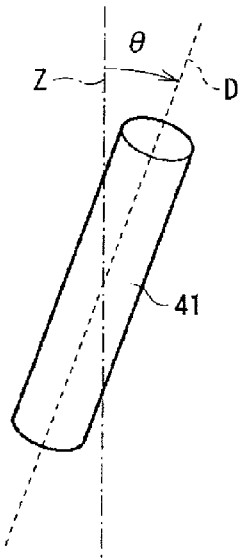
FIG. 2 is a schematic view for explaining pretilt of a liquid crystal molecule.

The liquid crystal molecule 41 is able to be categorized into a liquid crystal molecule 41A retained by the alignment film 22 in the vicinity of the interface with the alignment film 22, a liquid crystal molecule 41B retained by the alignment film 32 in the vicinity of the interface with the alignment film 32, and a liquid crystal molecule 41C other than the liquid crystal molecule 41A and the liquid crystal molecule 41B. The liquid crystal molecule 41C is located in the intermediate region in the thickness direction of the liquid crystal layer 40, and is aligned so that the long axis direction (director) of the liquid crystal molecule 41C becomes almost vertical to glass substrates 20A and 30A in a state that a drive voltage is off. In the case where the drive voltage is on, the liquid crystal molecule 41C is aligned at a tilt so that the director of the liquid crystal molecule 41C becomes in parallel with the glass substrates 20A and 30A. Such behavior results from a fact that in the liquid crystal molecule 41C, the dielectric constant in the long axis direction is smaller than that in the short axis direction. The liquid crystal molecule 41A and the liquid crystal molecule 41B have similar characteristics, and thus the liquid crystal molecule 41A and the liquid crystal molecule 41B fundamentally show behavior similar to that of the liquid crystal molecule 41C according to on/off state change of the drive voltage. However, in a state where a drive voltage is off, the liquid crystal molecule 41A is given with pretilt θ1 by the alignment film 22, and the director thereof is tilted from the normal line direction of the glass substrates 20A and 30A. Similarly, the liquid crystal molecule 41B is given with pretilt θ2 by the alignment film 32, and the director thereof is tilted from the normal line direction of the glass substrates 20A and 30A. In this case, "to be retained" means that the orientation films 22 and 32 are not firmly fixed with the liquid crystal molecules 41A and 41C, and alignment of the liquid crystal molecules 41 is regulated. "pretilt θ(θ1 and θ2)" means a tilt angle of a director D of the liquid crystal molecule 41 (41A and 41B) in the Z direction in a state that a drive voltage is off, where the direction vertical to the surface of the glass substrates 20A and 30A (normal line direction) is Z as illustrated in FIG. 2.

In the liquid crystal layer 40, both the pretilt θ1 and the pretilt θ2 have a value larger than 0 deg. In the liquid crystal layer 40, the pretilt θ1 and the pretilt θ2 may be the same angle (θ1=θ2), or the pretilt θ1 and the pretilt θ2 may be an angle different from each other (θ1≠θ2). Specially, the pretilt θ1 and the pretilt θ2 are preferably different from each other. Thereby, response rate to application of a drive voltage is more improved than in a case that both the pretilt θ1 and the pretilt θ2 are 0 deg. In addition, contrast almost equal to that of the case that both the pretilt θ1 and the pretilt θ2 are 0 deg is able to be obtained. Thus, while response characteristics are improved, the light transmission amount in black display is able to be decreased and contrast is able to be improved. In the case where the pretilt θ1 and the pretilt θ2 are an angle different from each other, the larger pretilt θ out of the pretilt θ1 and the pretilt θ2 is more desirably from 1 deg to 4 deg both inclusive. By setting the larger pretilt θ to a value in the foregoing range, particularly high effect is obtained.

Figure 5:
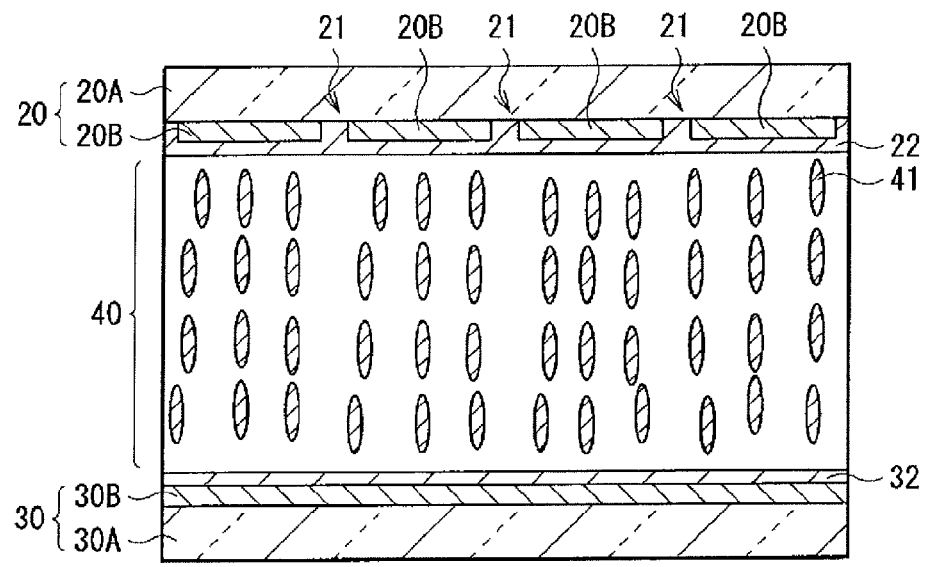
FIG. 5 is a schematic partial cross sectional view of a substrate or the like for explaining the method of manufacturing the liquid crystal display unit illustrated in FIG. 1.
Figure 6:
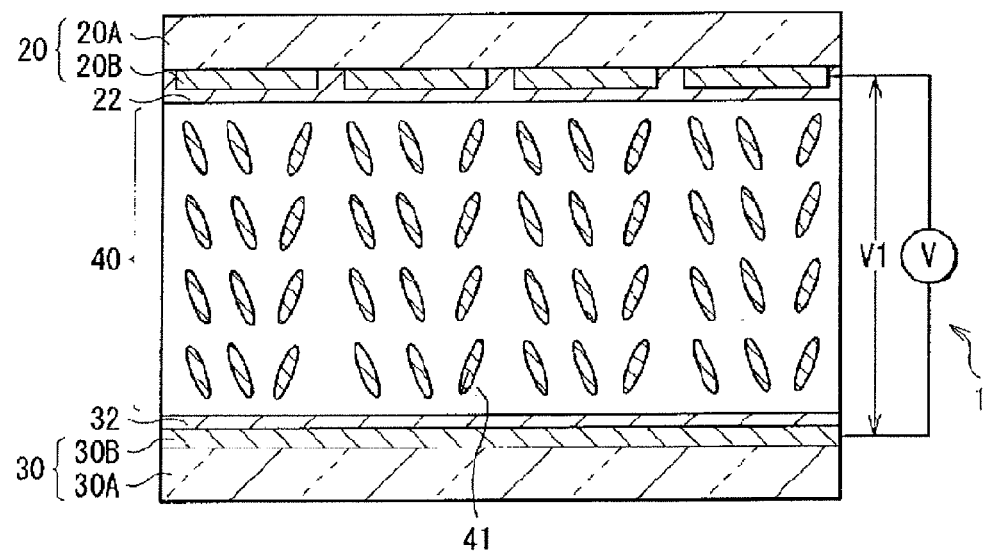
FIG. 6 is a schematic partial cross sectional view of the substrate or the like for explaining a step following FIG. 5
Figure 7A:
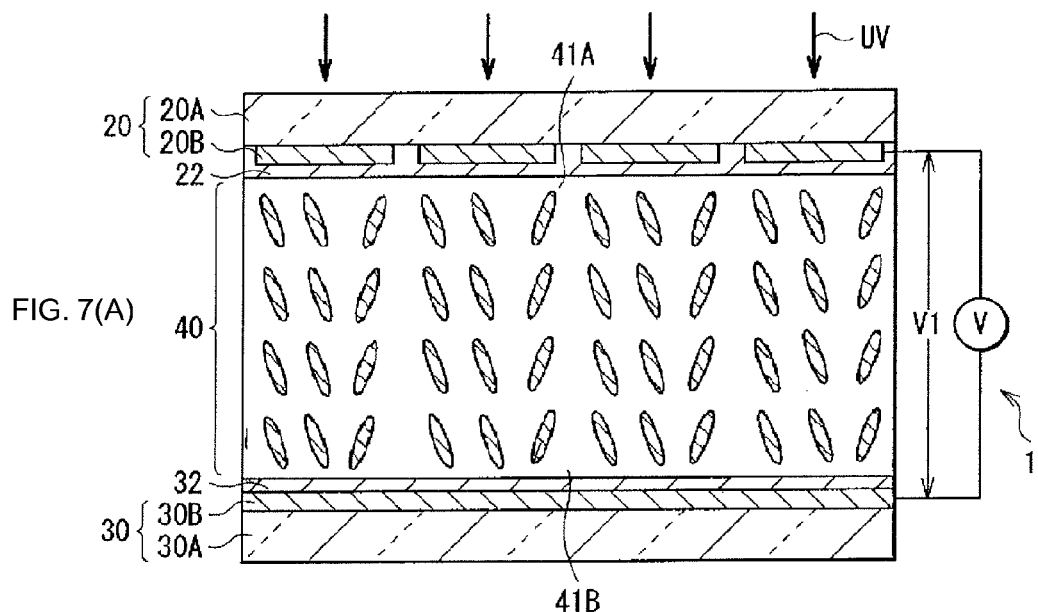
FIG. 7A is a schematic partial cross sectional view of the substrate or the like for explaining a step following FIG. 6.

Next, a description will be given of a method of manufacturing the foregoing liquid crystal display unit (liquid crystal display device) with reference to the flowchart shown in FIG. 3, the schematic view for explaining a state in the alignment films 22 and 32 illustrated in FIG. 4, and the schematic partial cross sectional view of the liquid crystal display unit or the like illustrated in FIG. 5, FIG. 6, and FIG. 7A. FIG. 5, FIG. 6, and FIG. 7A illustrate only a cross section for one pixel for simplicity.

First, the alignment film 22 is formed on the surface of the TFT substrate 20, and the alignment film 32 is formed on the surface of the CF substrate 30 (step S101).

Specifically, first, the TFT substrate 20 is formed by providing the pixel electrode 20B having a predetermined slit section 21 in a state of, for example, matrix on the surface of the glass substrate 20A. Further, the CF substrate 30 is formed by providing the opposed electrode 30B on the color filter of the glass substrate 30A on which the color filter is formed.

Meanwhile, for example, the compound before alignment process or a polymer compound precursor as the compound before alignment process, a solvent, and if necessary a vertical aligner are mixed, and thereby a liquid alignment film material is prepared.

Examples of the polymer compound precursor as the compound before alignment process include polyamic acid having a crosslinkable functional group in the case where the polymer compound having a crosslinkable functional group as a side chain contains the polyimide structure shown in Formula (3). The polyamic acid as the polymer compound precursor is synthesized, for example, by reacting a diamine compound with a tetracarboxylic acid dianhydride. At least one of the diamine compound and the tetracarboxylic acid dianhydride herein used has a crosslinkable functional group. Examples of the diamine compound include a compound having a crosslinkable functional group expressed by Formula (A-1) to Formula (A-15). Examples of the tetracarboxylic acid dianhydride include a compound having a crosslinkable functional group expressed by Formula (a-1) to Formula (a-10). The compound expressed by Formula (A-9) to Formula (A-15) is a compound structuring the cross-linked section and the end structure section of the cross-linked polymer compound in the 1C structure of the present invention. Otherwise, examples of the compound structuring the cross-linked section and the end structure section of the cross-linked polymer compound in the 1C structure of the present invention include a compound expressed by Formula (F-1) to Formula (F-18). In the compound expressed by Formula (F-1) to Formula (F-18), pretilt may be given to the liquid crystal molecule along the end structure section of the compound expressed by Formula (F-1) to Formula (F-3), Formula (F-7) to Formula (F-9), and Formula (F-13) to Formula (F-15), while pretilt may be given to the liquid crystal molecule sandwiched by the end structure sections of the compound expressed by Formula (F-4) to Formula (F-6), Formula (F-10) to Formula (F-12), and Formula (F-16) to Formula (F-18).

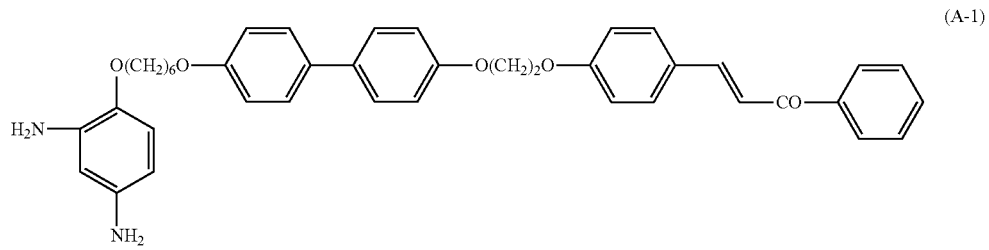

(A-1)

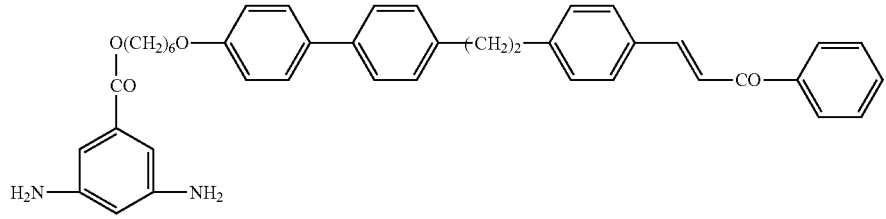
(A-2)
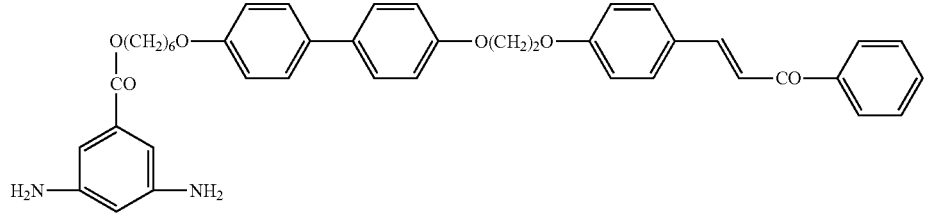
(A-3)
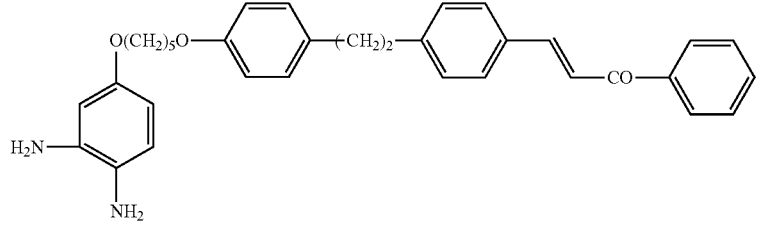
(A-4)
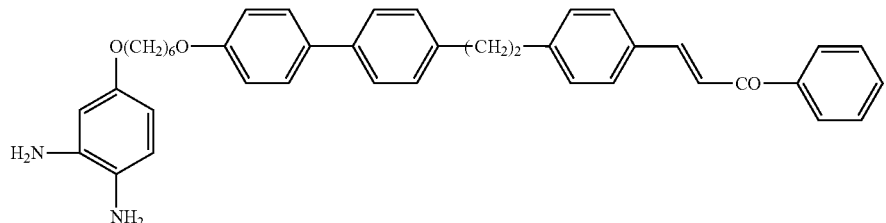
(A-5)
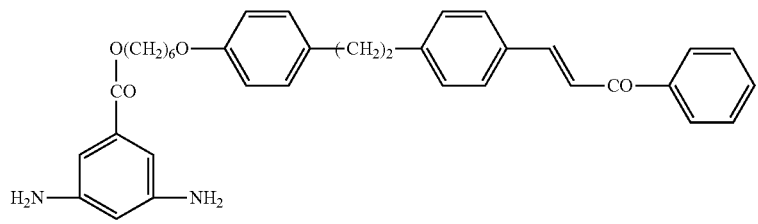
(A-6)
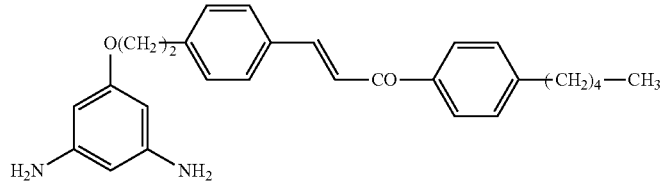
(A-7)
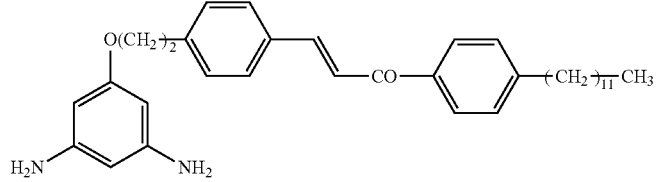
(A-8)

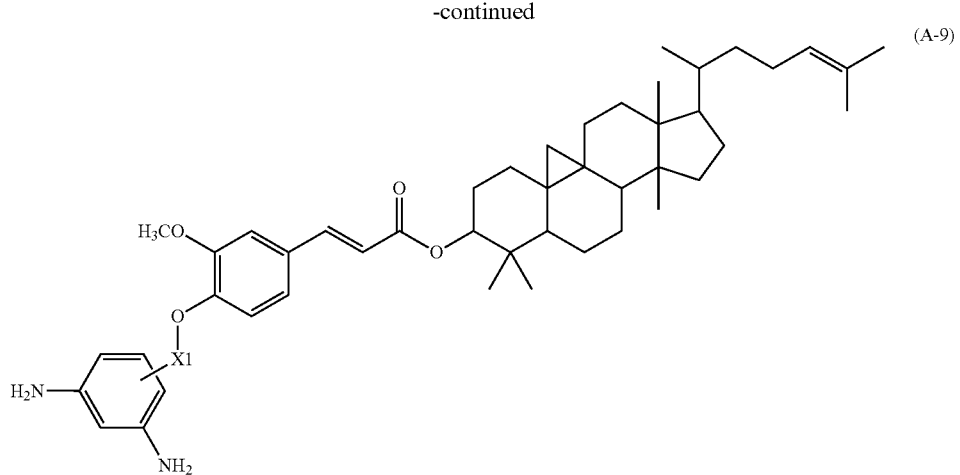
(A-9)
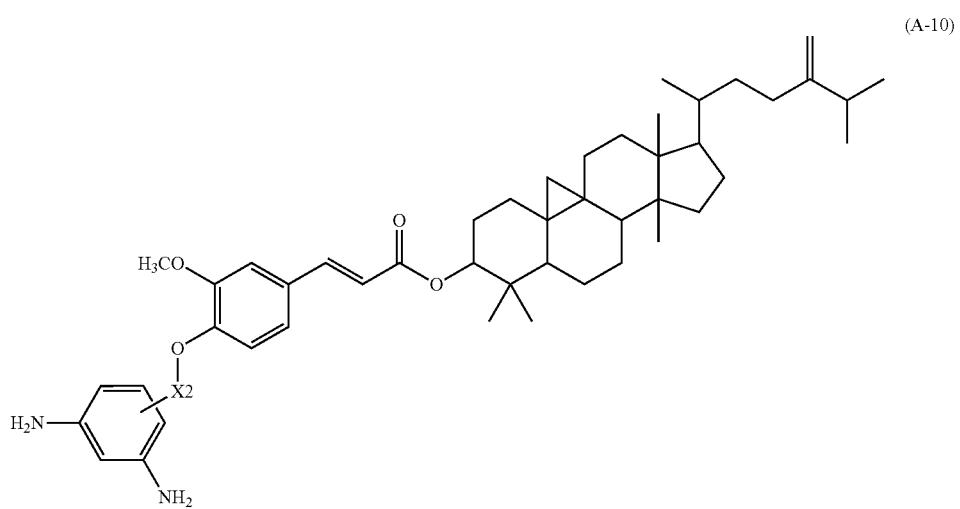
(A-10)
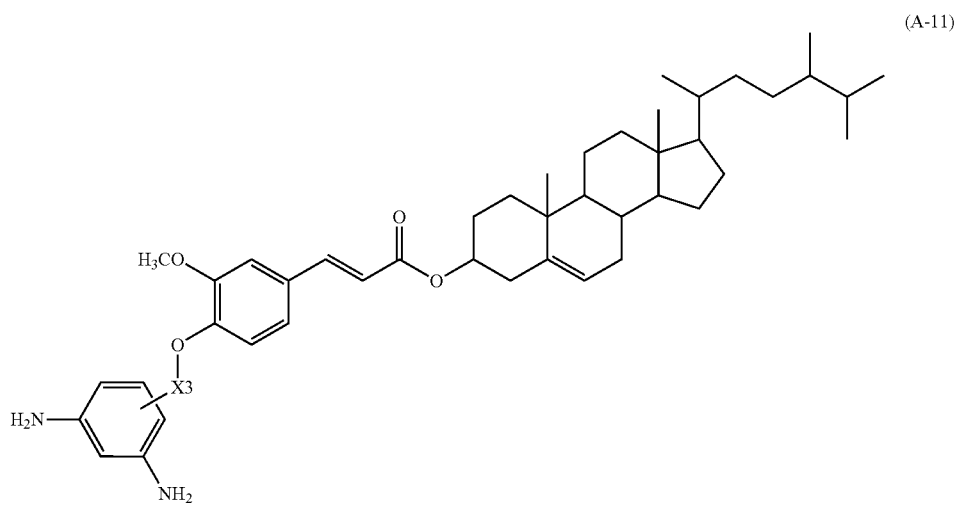
(A-11)

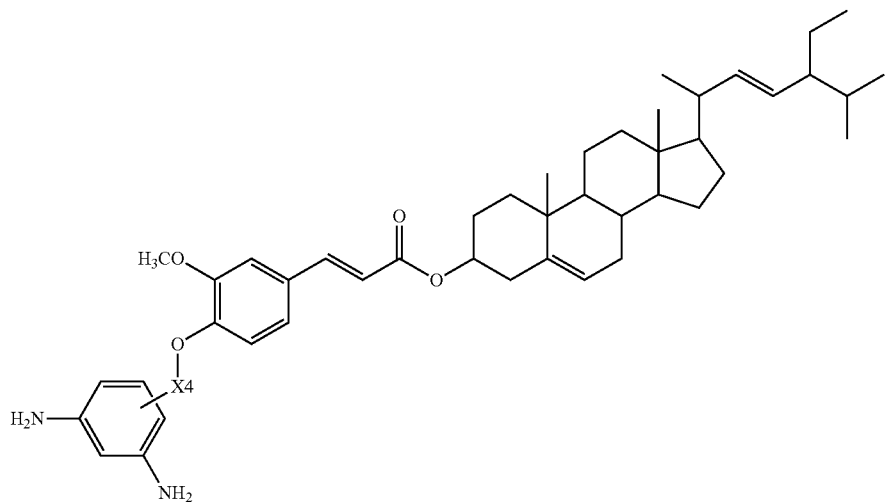
(A-12)
In the formula, X1 to X4 represent a single bond or a bivalent organic group.
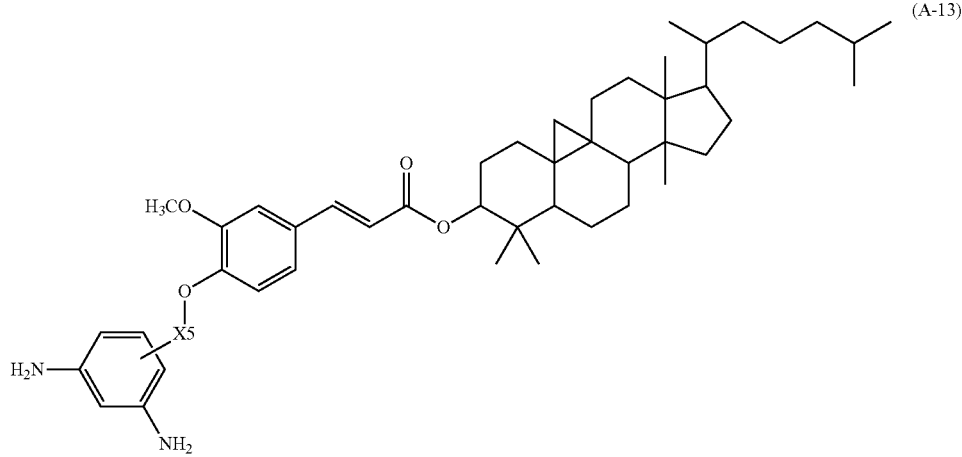
(A-13)
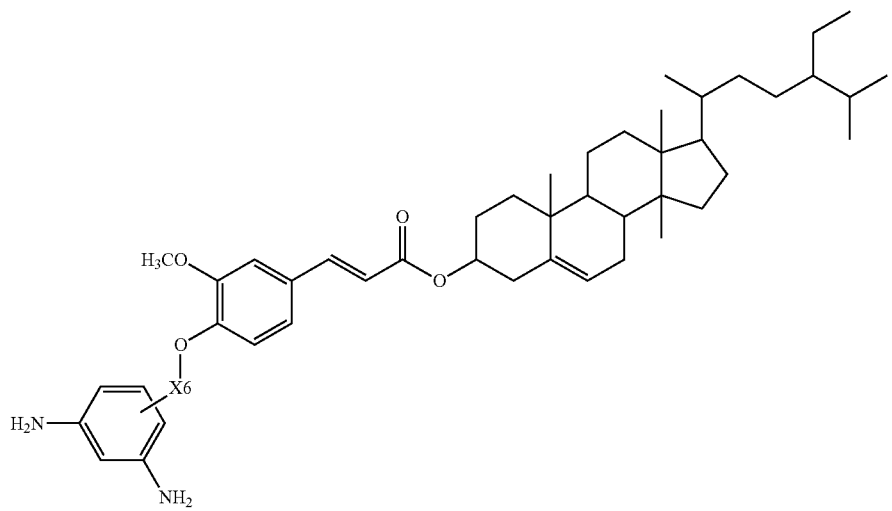
(A-14)

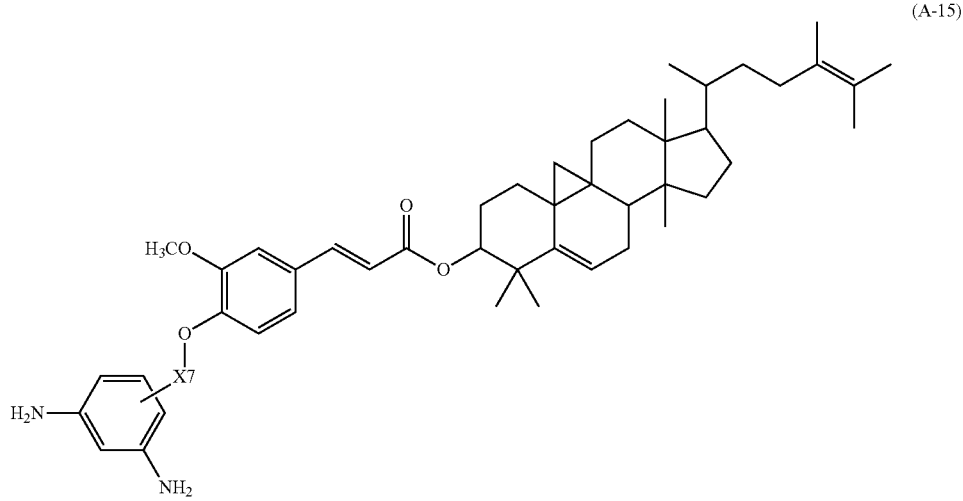
(A-15)
In the formula, X5 to X7 represent a single bond or a bivalent organic group.
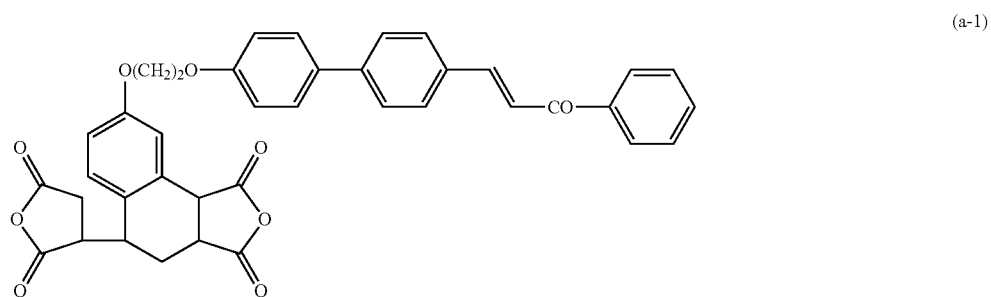
(a-1)
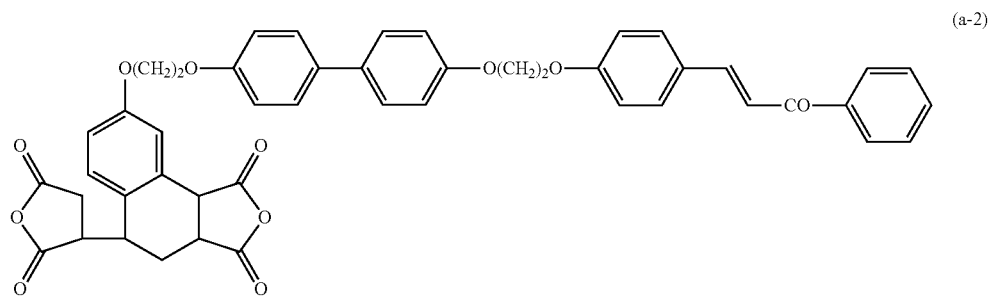
(a-2)
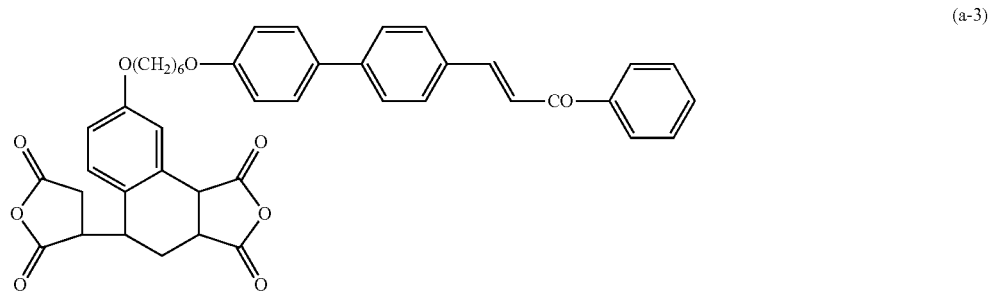
(a-3)

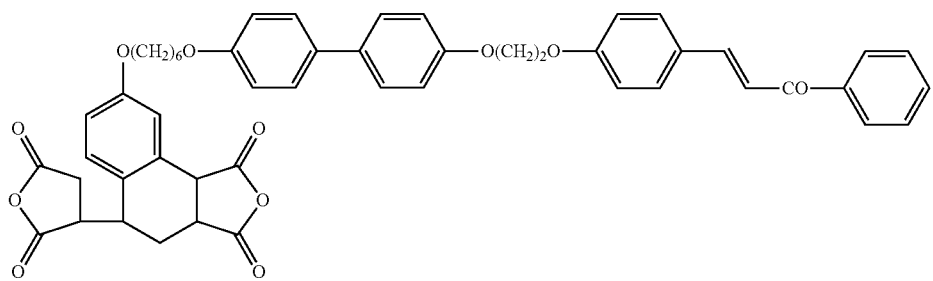
(a-4)
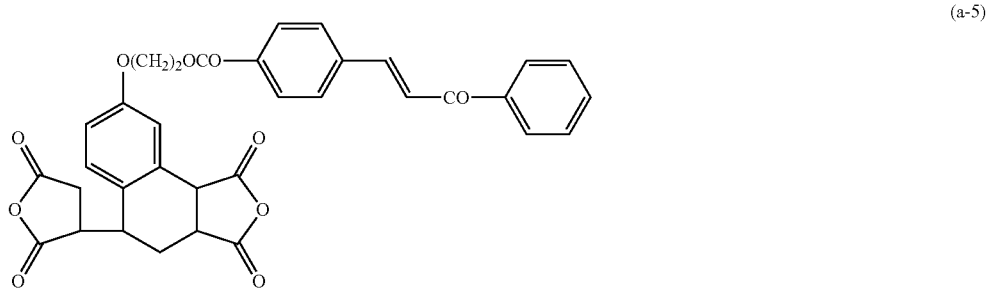
(a-5)
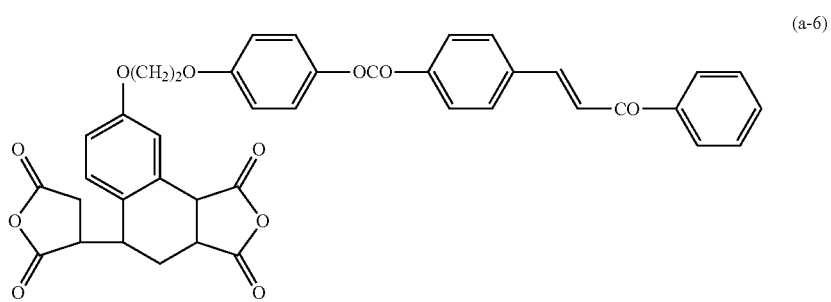
(a-6)
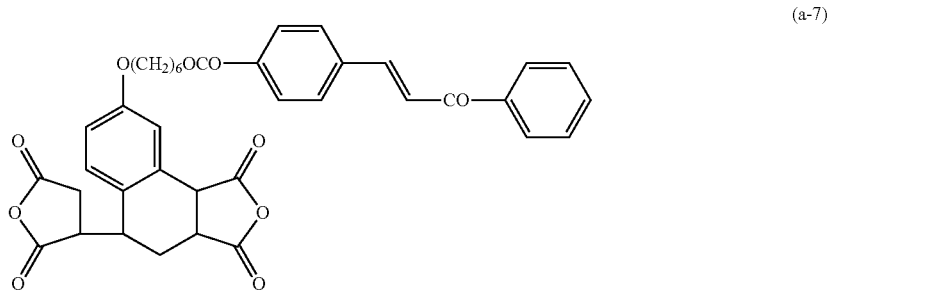
(a-7)
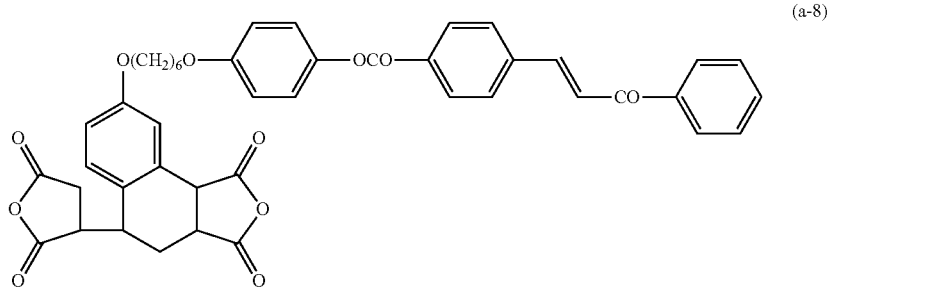
(a-8)

-continued
(a-9)
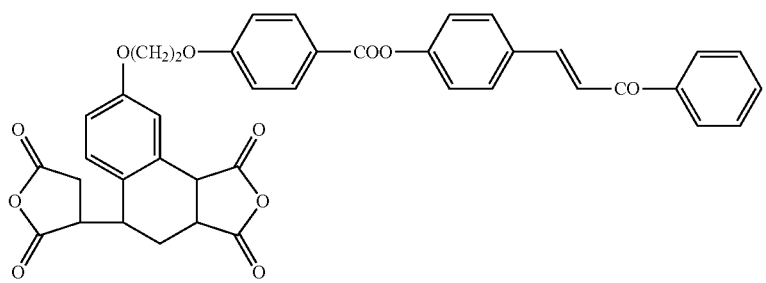
(a-10)
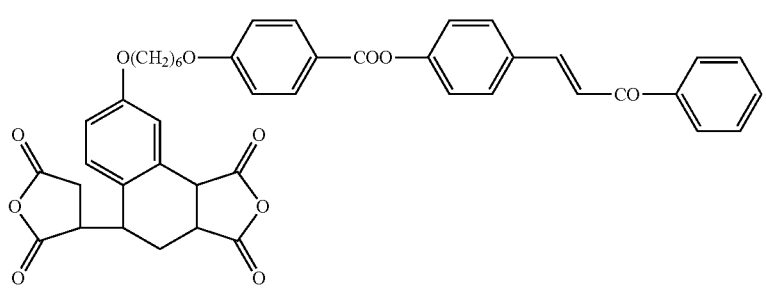
(F-1)
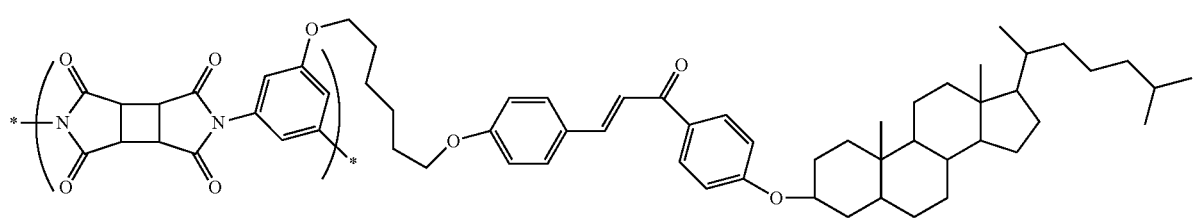
(F-2)
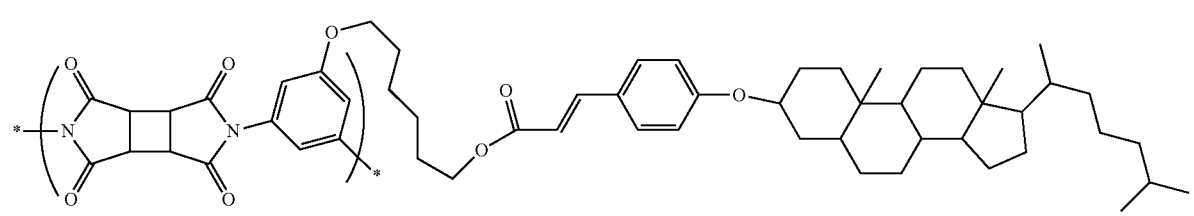
(F-3)
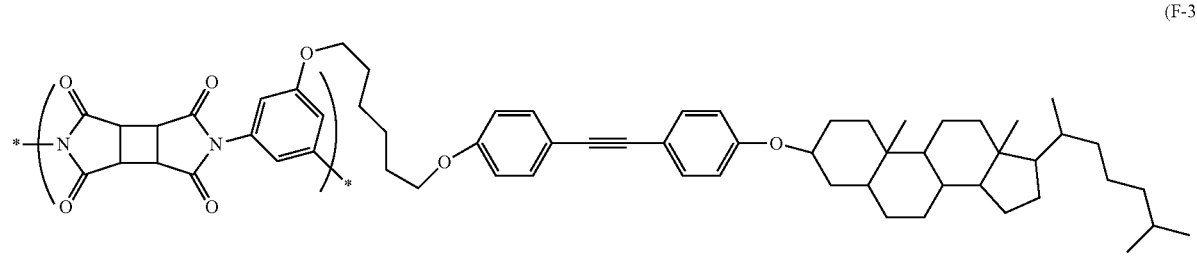
(F-4)
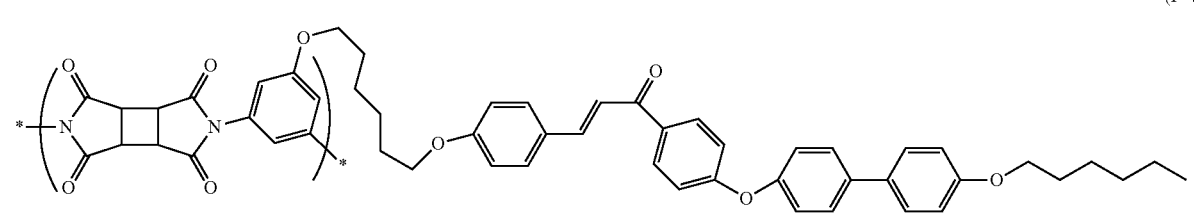

(F-5)
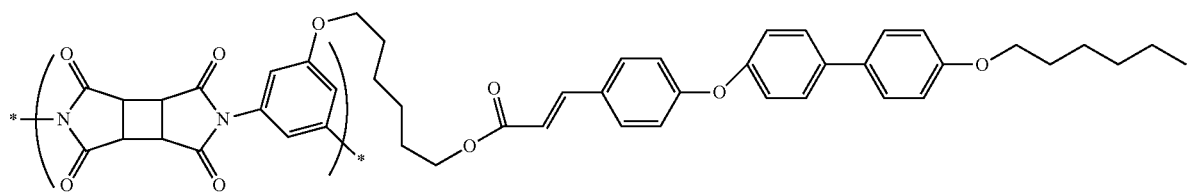
(F-6)
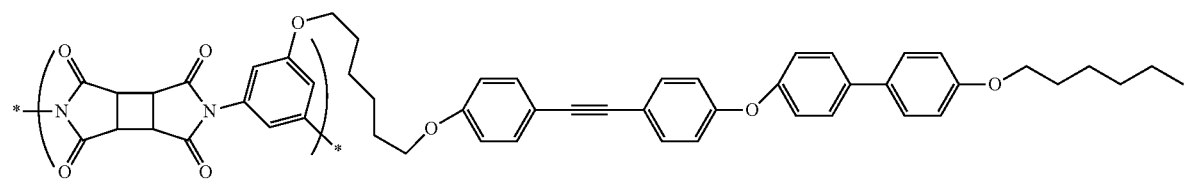
(F-7)
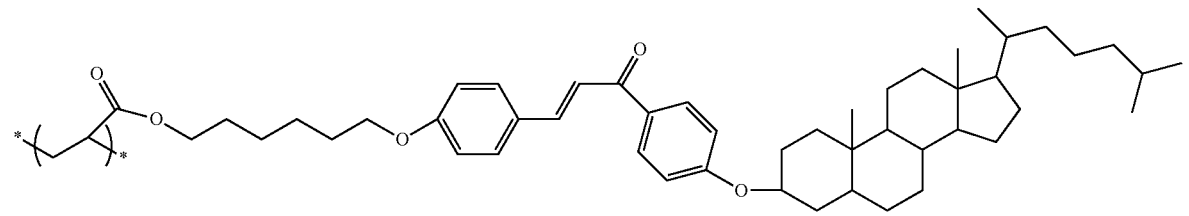
(F-8)
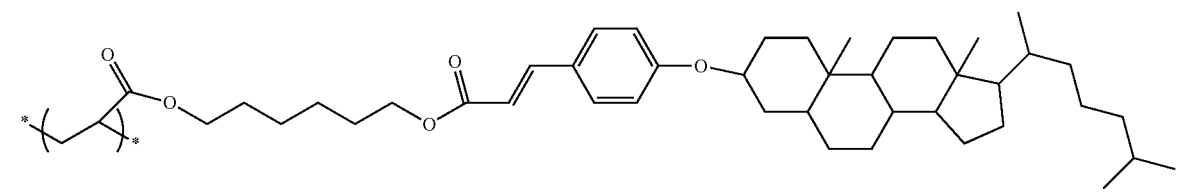
(F-9)
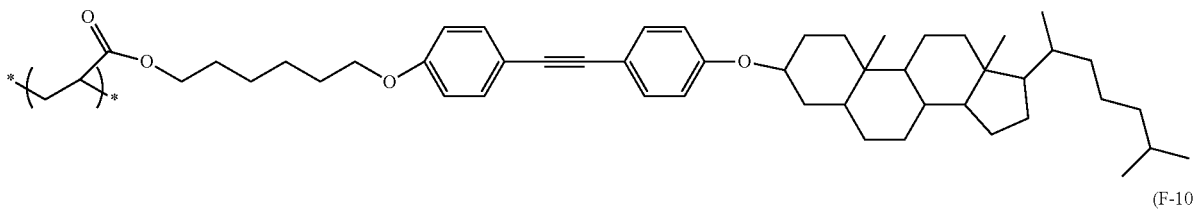
(F-10)
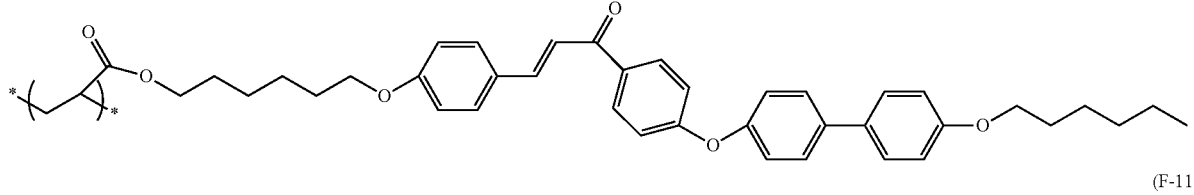
(F-11)
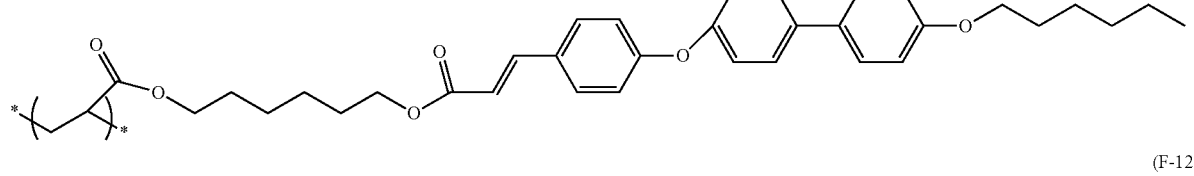
(F-12)
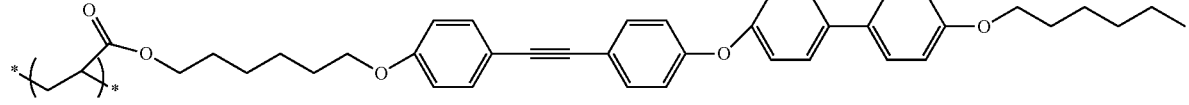

-continued

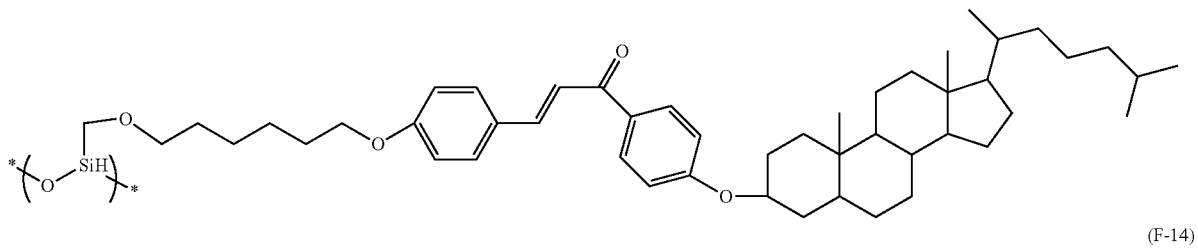
(F-13)

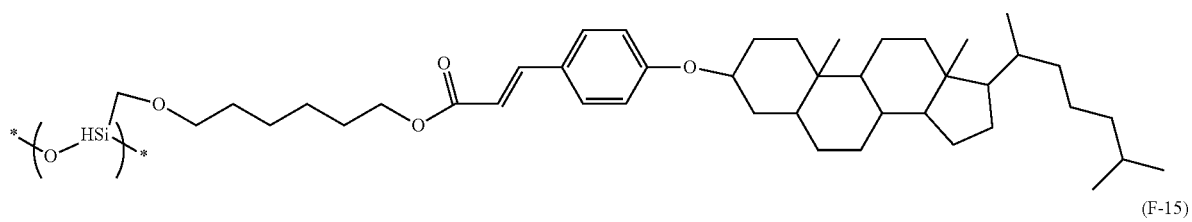
(F-14)

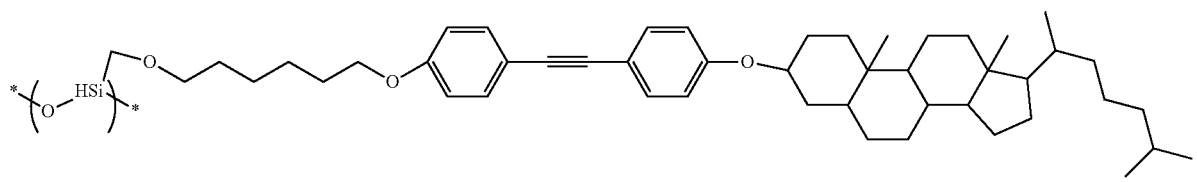
(F-15)

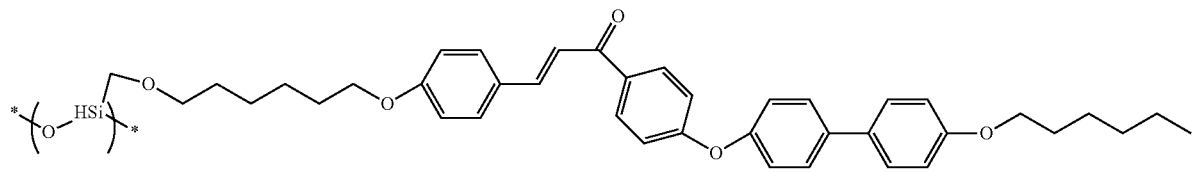
(F-16)

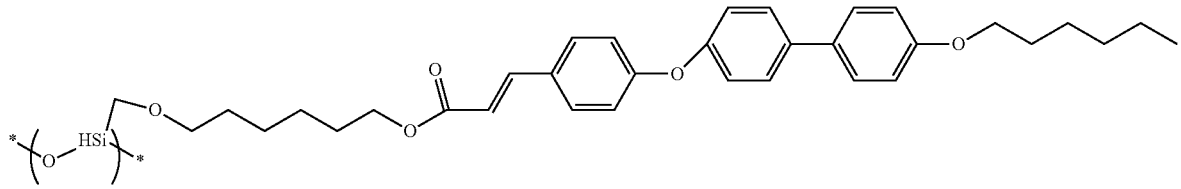
(F-17)

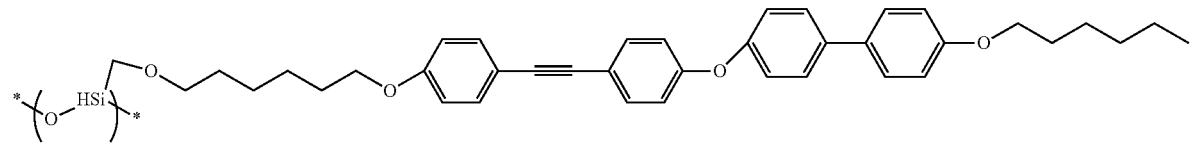
(F-18)

Further, in the case where the polyamic acid as the polymer compound precursor is synthesized so that the compound before alignment process contains a vertical alignment induction structure section, in addition to the foregoing compound having a crosslinkable functional group, compounds having a vertical alignment induction structure section expressed by Formula (B-1) to Formula (B-36) as a diamine compound or compounds having a vertical alignment induction structure section expressed by Formula (b-1) to Formula (b-3) as tetracarboxylic acid dianhydride may be used.

(B-1) 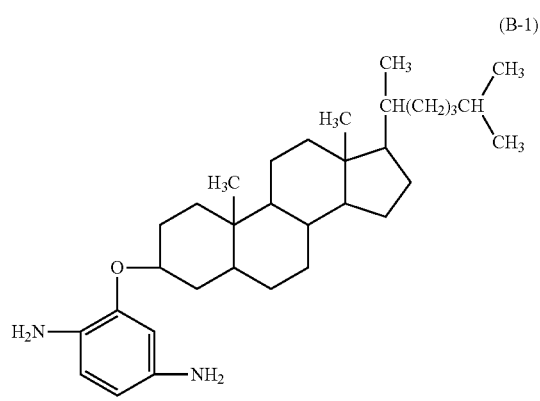
(B-2) 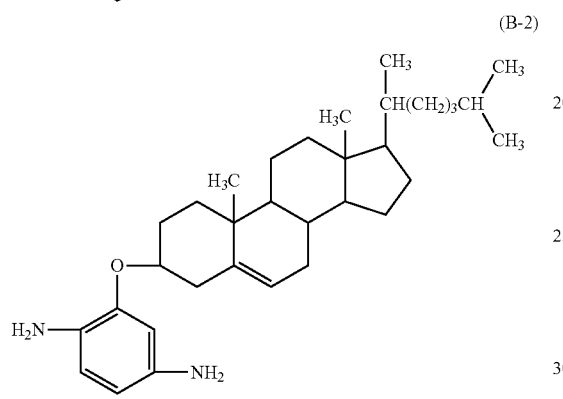
(B-3) 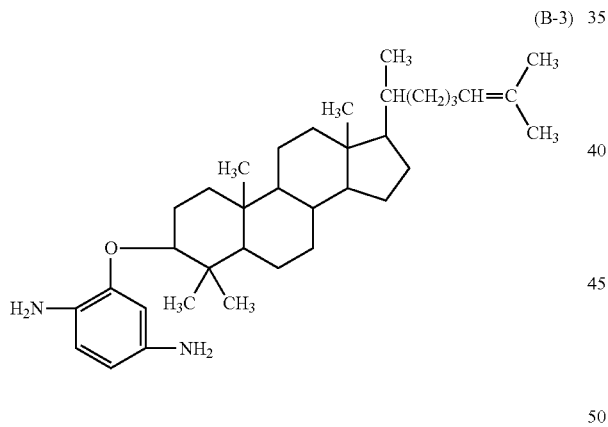
(B-4) 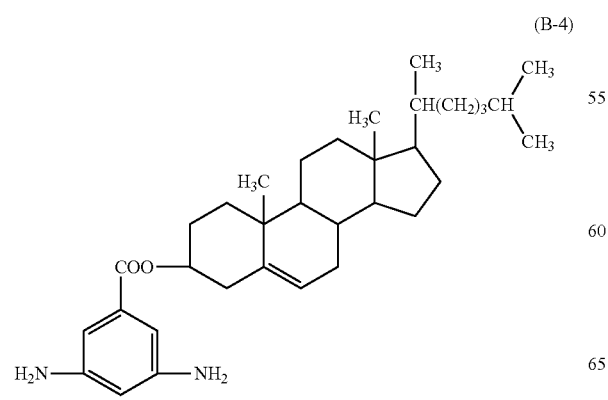
-continued
(B-5) 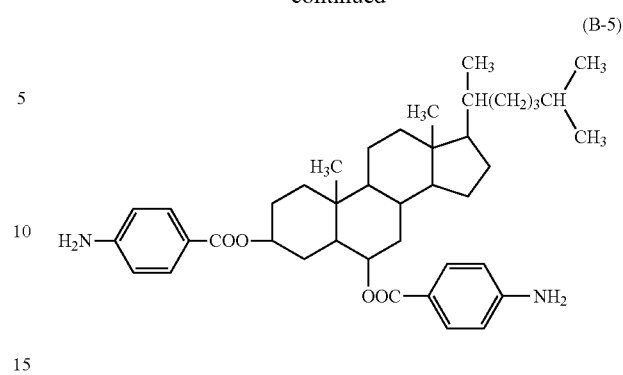
(B-6) 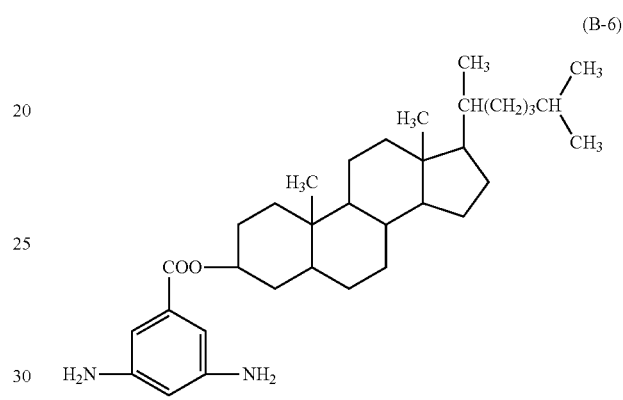
(B-7) 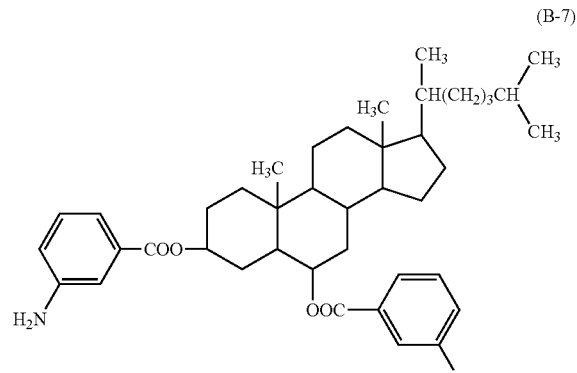
(B-8) 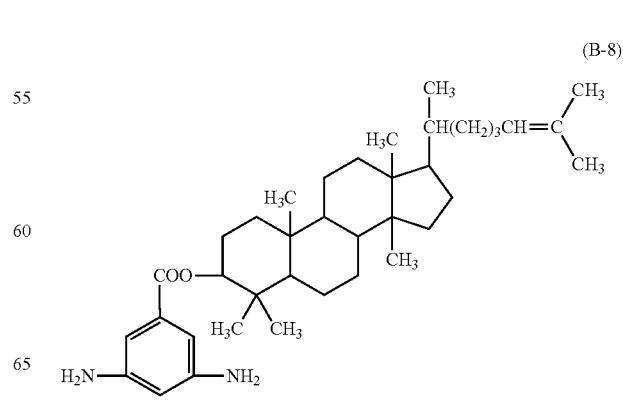

(B-9) 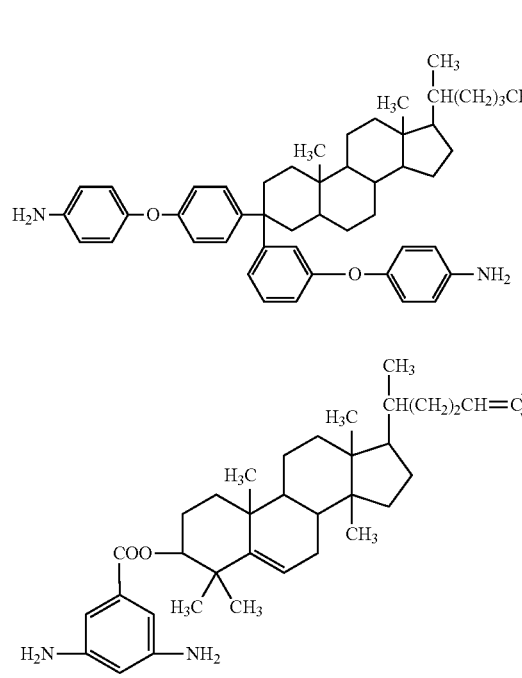
(B-10) 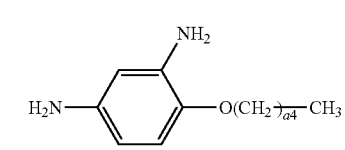
(B-11) 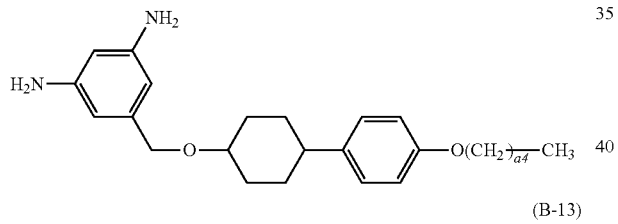
(B-12) 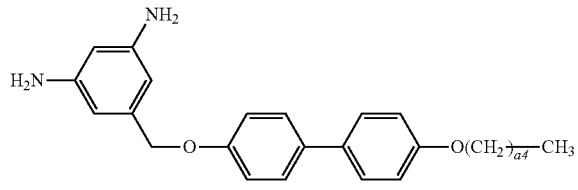
(B-13) 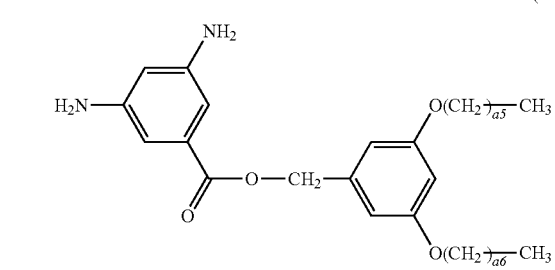
(B-14)
(B-15) 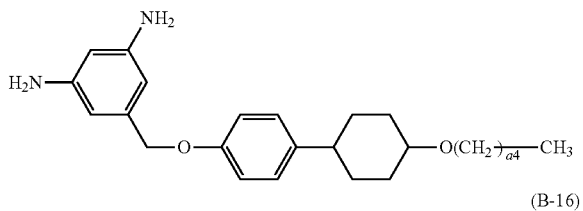
(B-16) 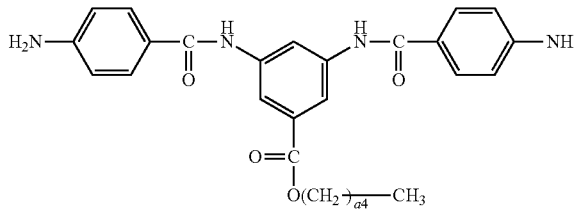
(B-17) 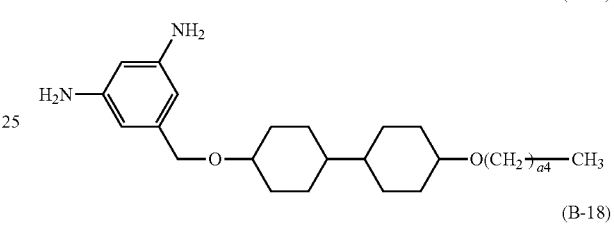
(B-18) 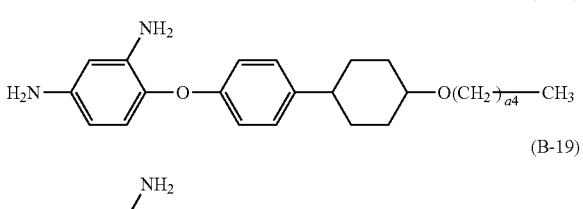
(B-19) 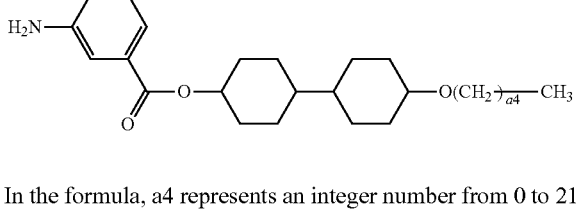
In the formula, a4 represents an integer number from 0 to 21 both inclusive.
(B-20) 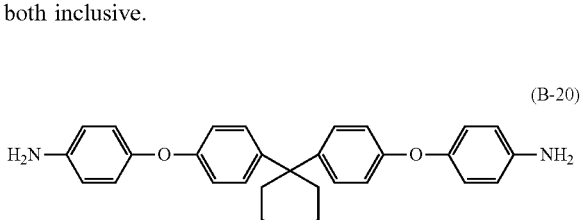
(B-21) 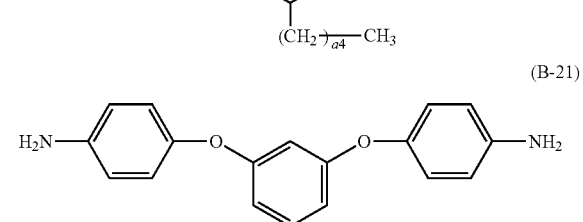
In the formula, a4 to a6 represent an integer number from 0 to 21 both inclusive.

(B-22) 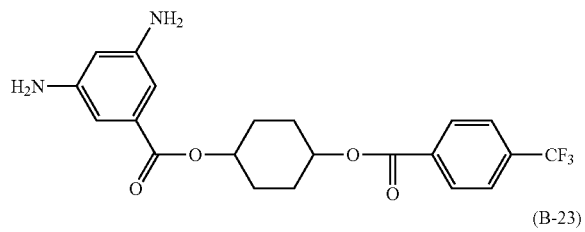
(B-23) 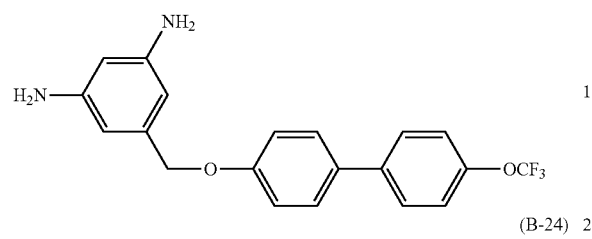
(B-24) 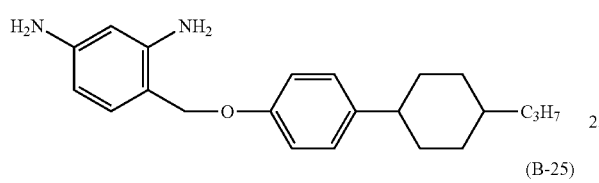
(B-25) 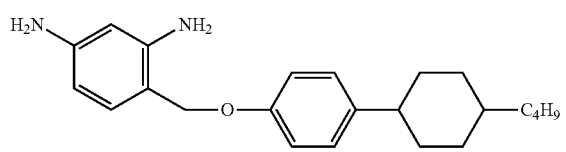
(B-26) 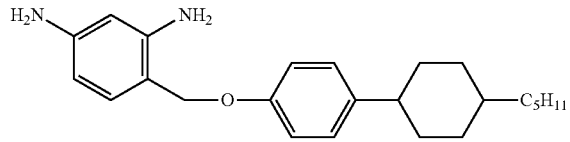
(B-27) 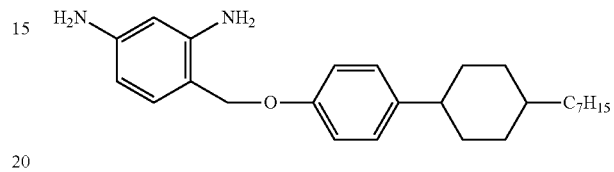
(B-28) 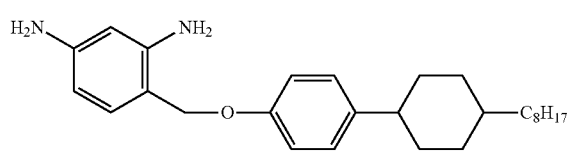
In the formula, a4 represents an integer number from 0 to 21 both inclusive.
(B-29) 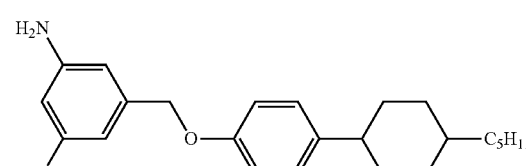
(B-30) 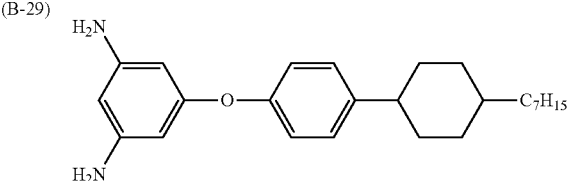
(B-31) 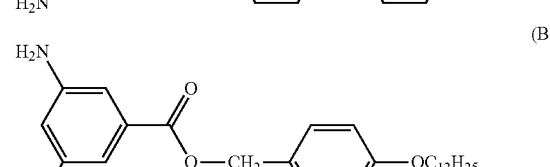
(B-32) 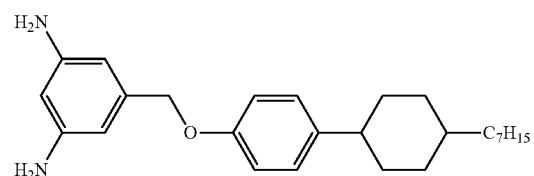
(B-33) 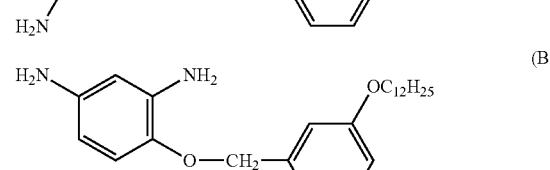
(B-34) 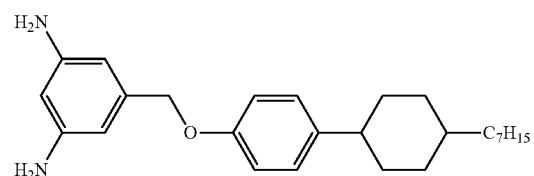
(B-35)
(B-36) 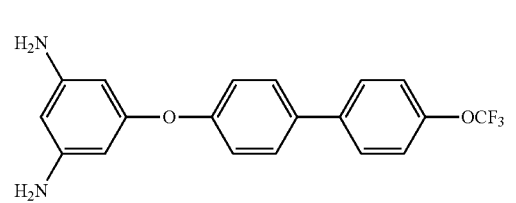

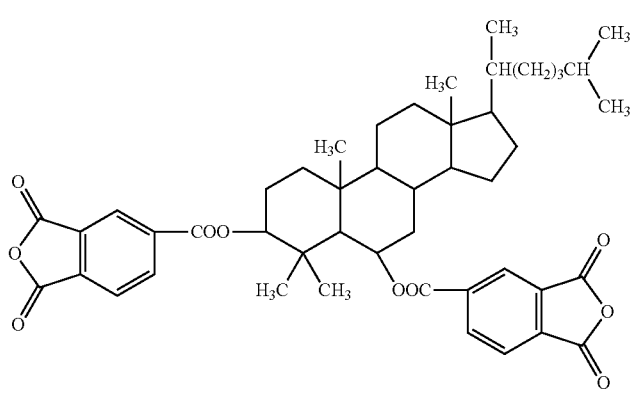

(b-1)

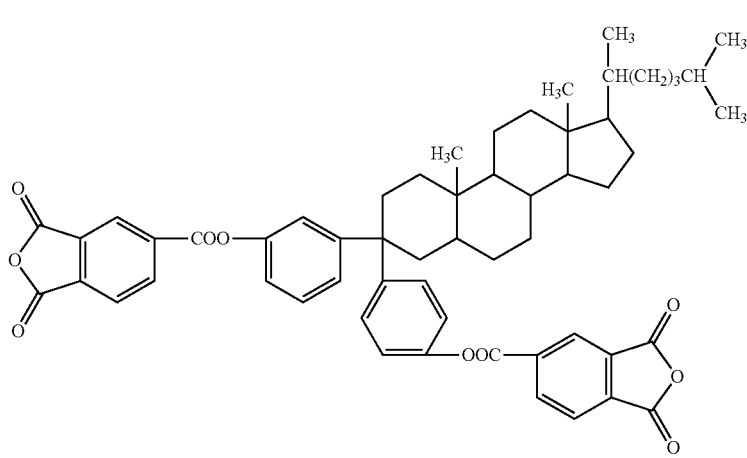

(b-2)

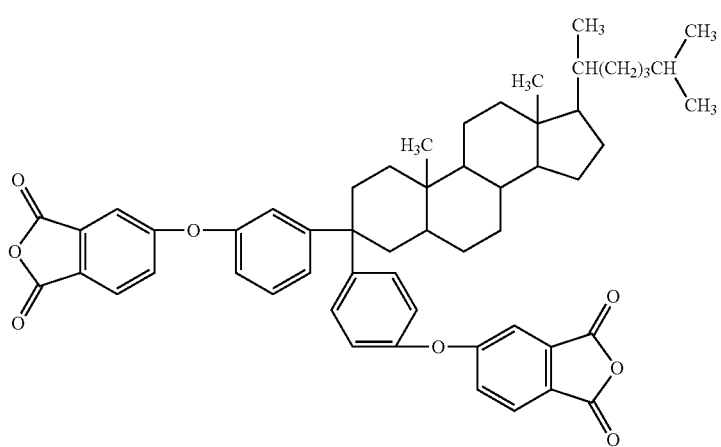

(b-3)

Further, in the case where the polyamic acid as the polymer compound precursor is synthesized so that the compound before alignment process contains the group shown in Formula (1) together with a crosslinkable functional group, in addition to the foregoing compound having a crosslinkable functional group, a compound having a group capable of being located along the liquid crystal molecule 41 expressed by Formula (C-1) to Formula (C-20) as a diamine compound may be used.

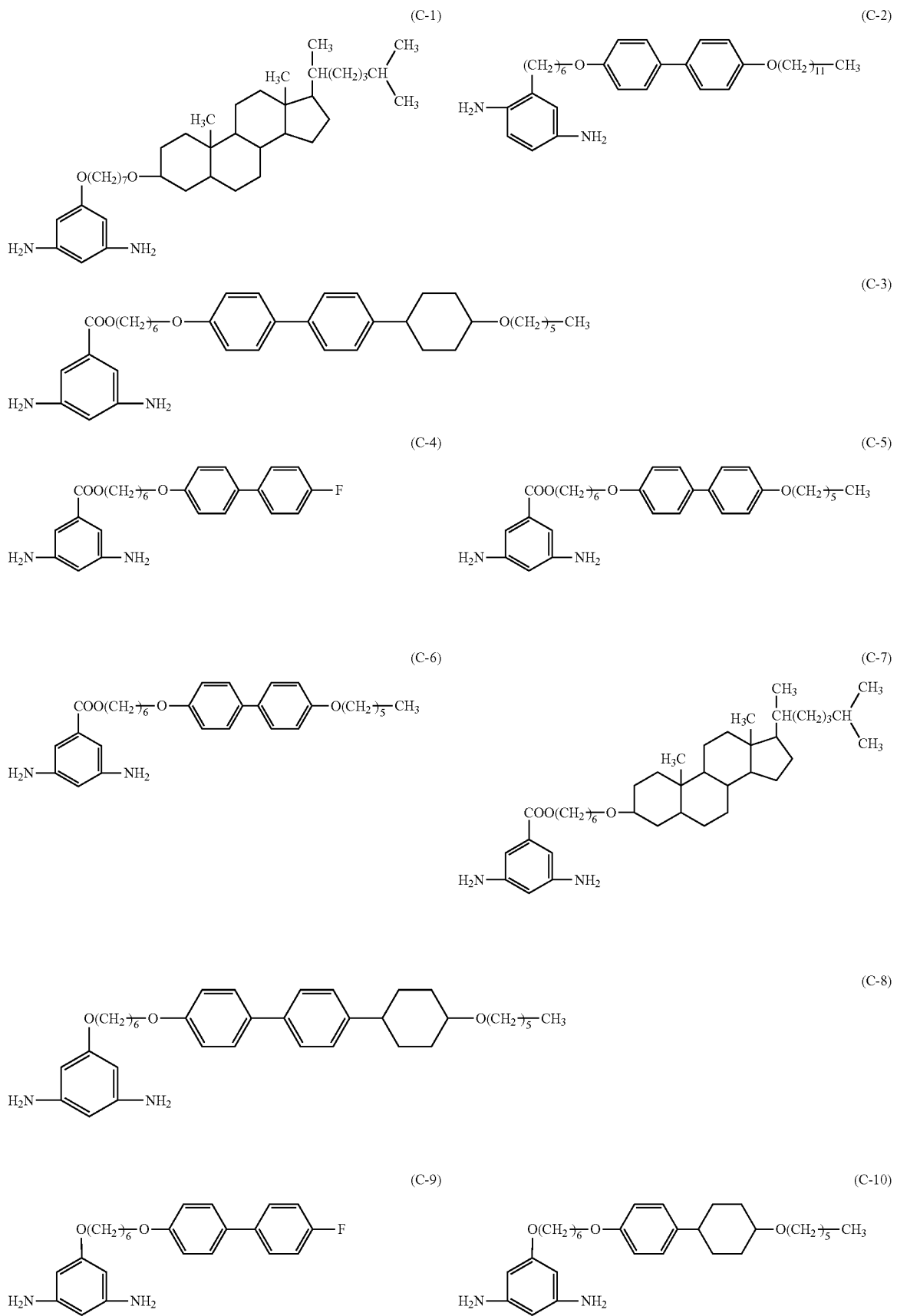

-continued
(C-11)
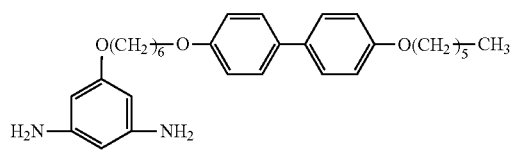
(C-12)
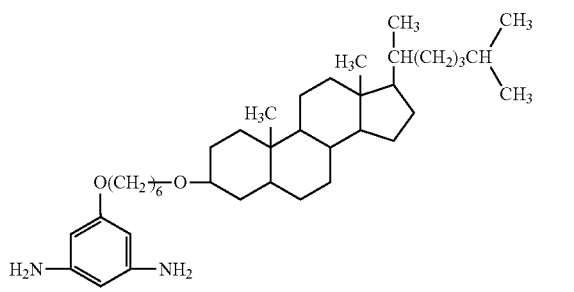
(C-13)
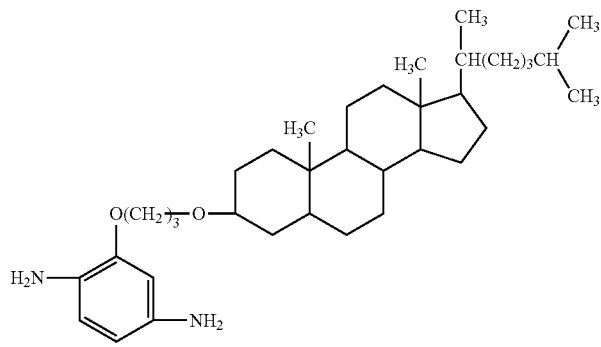
(C-14)
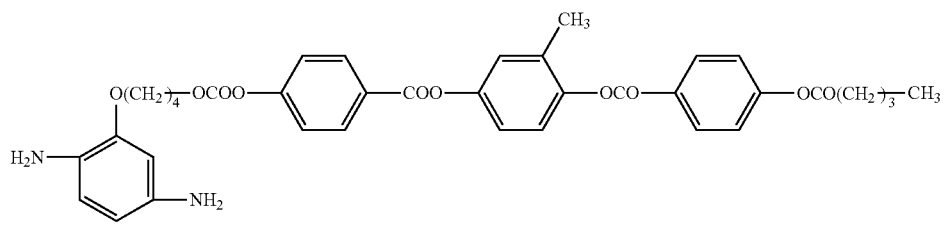
(C-15)
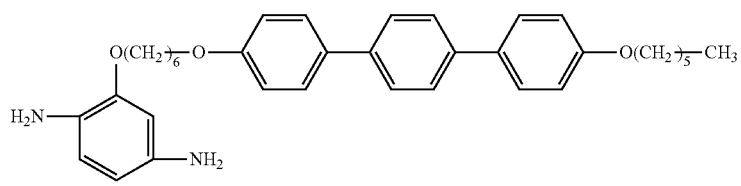
(C-16)
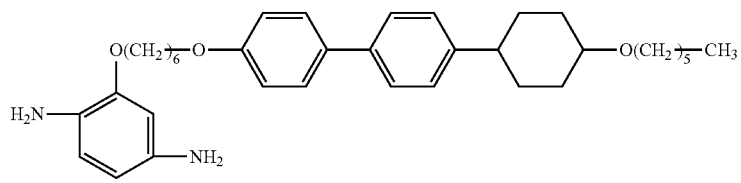
(C-17)
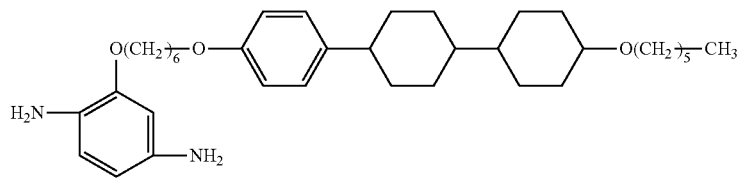
(C-18)
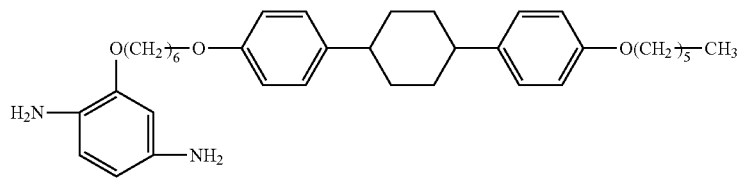

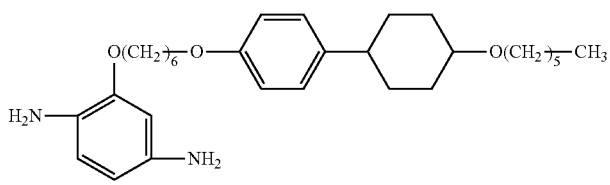

(C-19)

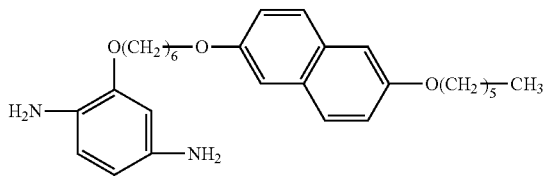

(C-20)

Further, in the case where the polyamic acid as the polymer compound precursor is synthesized so that the compound before alignment process has the group shown in Formula (2), in addition to the foregoing compound having a crosslinkable functional group, a compound having a group capable of being located along the liquid crystal molecule 41 expressed by Formula (D-1) to Formula (D-7) as a diamine compound may be used.

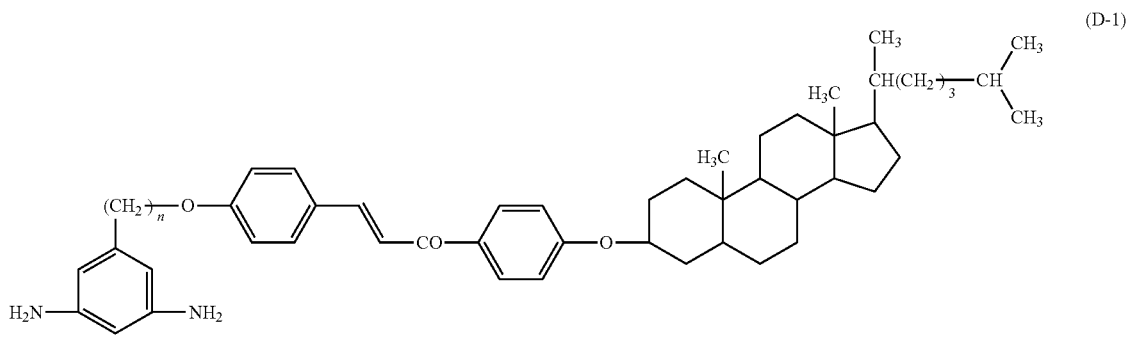

(D-1)

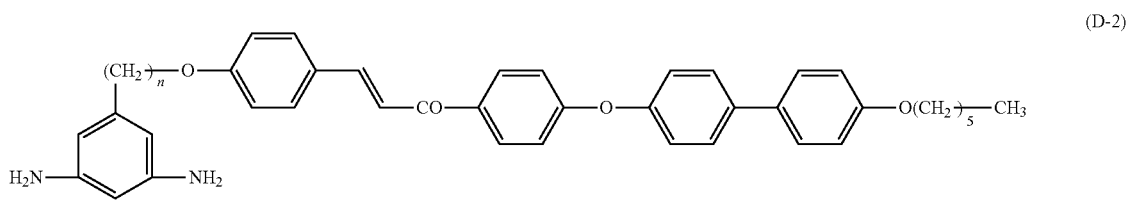

(D-2)

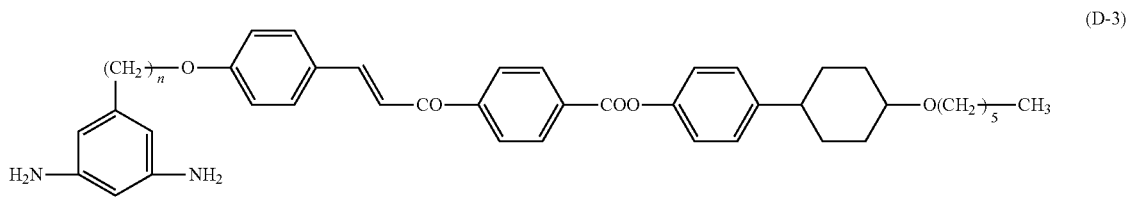

(D-3)

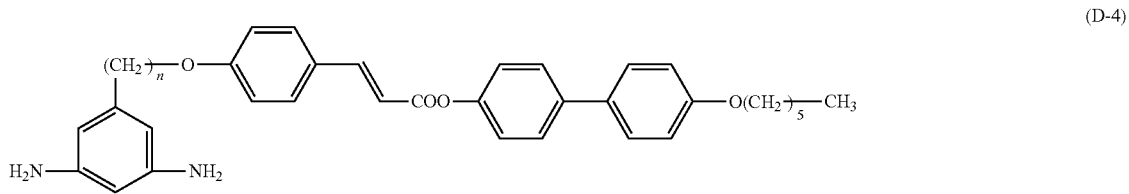

(D-4)

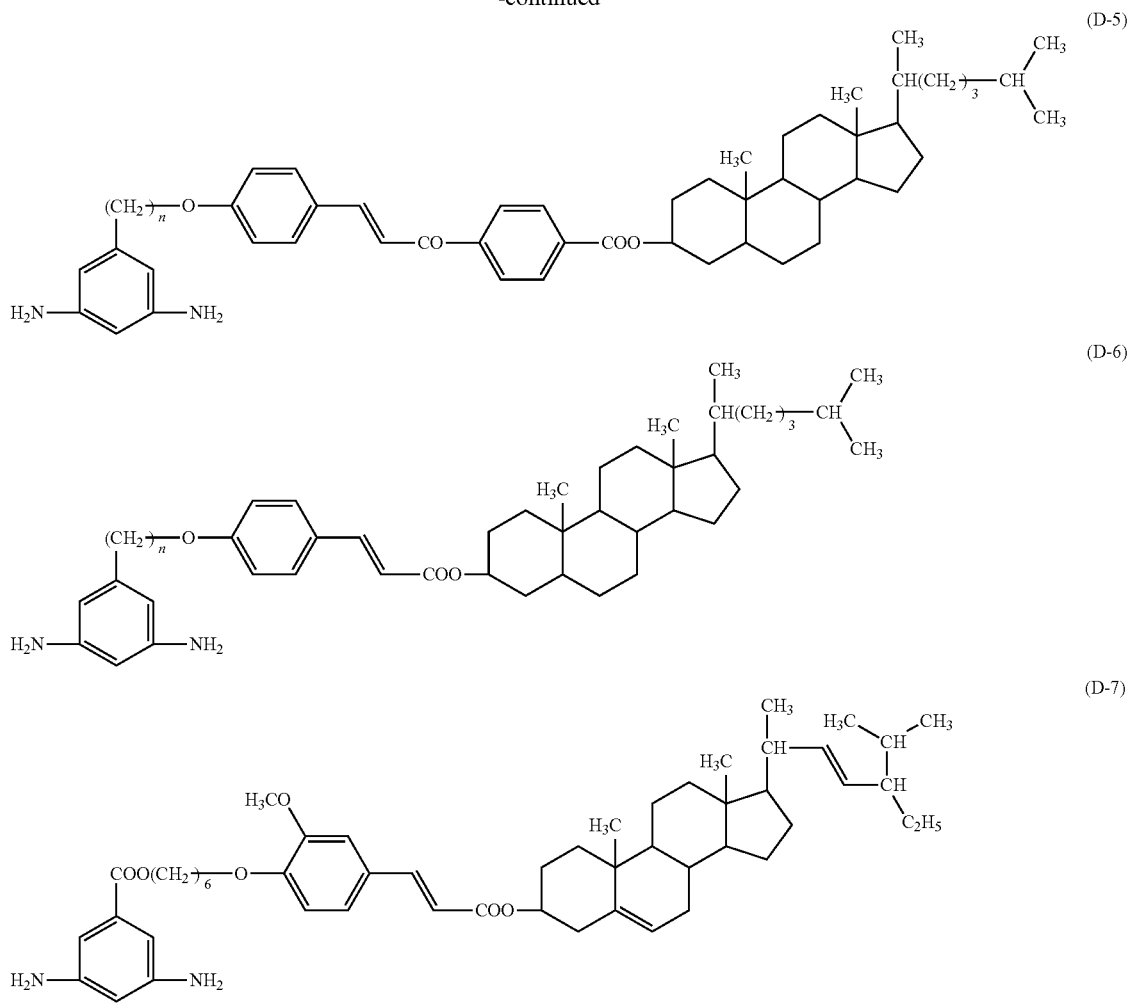

In the formula, n represents an integer number from 3 to 20 both inclusive.

Further, in the case where the polyamic acid as the polymer compound precursor is synthesized so that the compound before alignment process contains two types of structures that are a structure containing a vertical alignment induction structure section and a structure containing a crosslinkable functional group as R2 in formula (3), for example, a diamine compound and a tetracarboxylic acid dianhydride are selected as follows. That is, at least one of the compounds having a crosslinkable functional group expressed by Formula (A-1) to Formula (A-15), at least one of the compounds having a vertical alignment induction structure section expressed by Formula (B-1) to Formula (B-36) and Formula (b-1) to Formula (b-3), and at least one of the tetracarboxylic acid dianhydrides expressed by Formula (E-1) to Formula (E-28) are used. R1 and R2 in Formula (E-23) are the same or a different alkyl group, alkoxy group, or halogen atom. The halogen atom type is arbitrary.

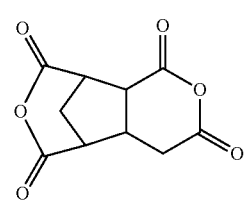

(E-1)

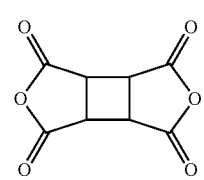

(E-2)

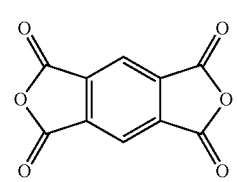

(E-3)

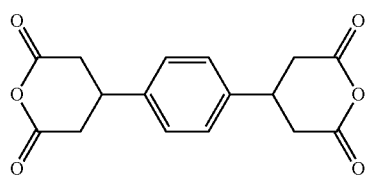
(E-4)
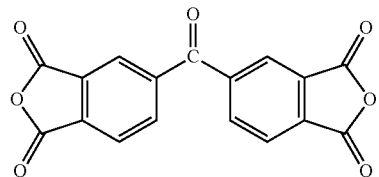
(E-5)
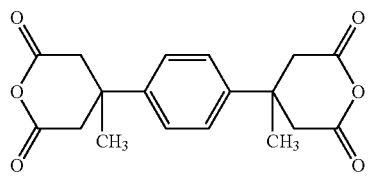
(E-6)
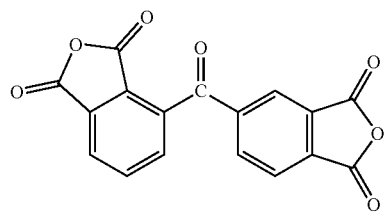
(E-7)
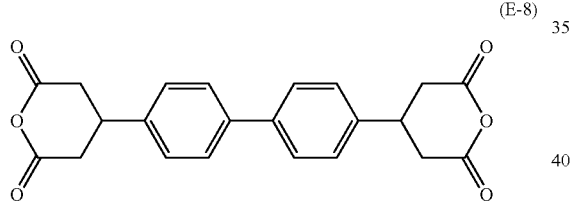
(E-8)
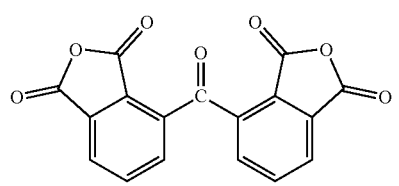
(E-9)
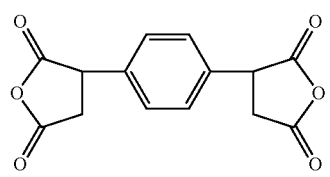
(E-10)
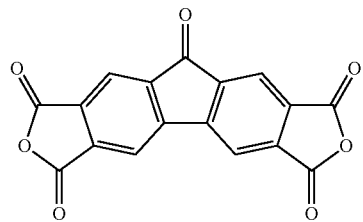
(E-11)
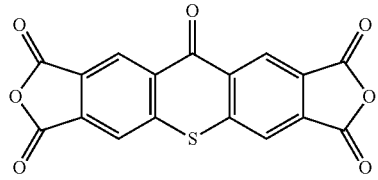
(E-12)
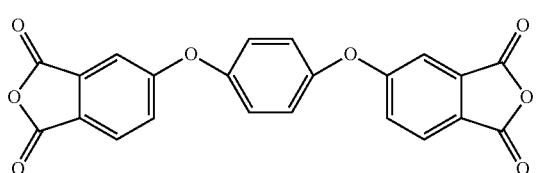
(E-13)
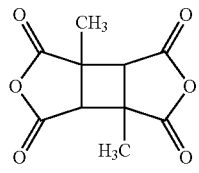
(E-14)
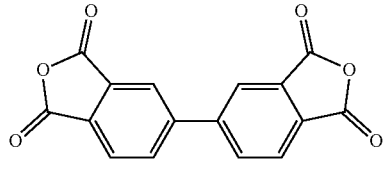
(E-15)
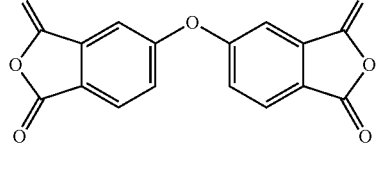
(E-16)
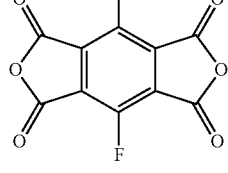
(E-17)
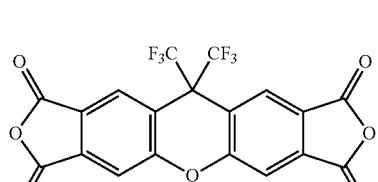
(E-18)
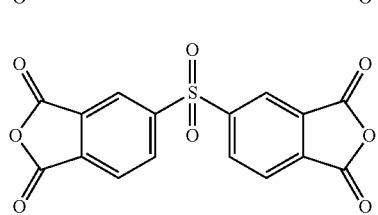
(E-19)

-continued (E-20) 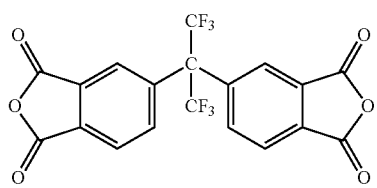

(E-21) 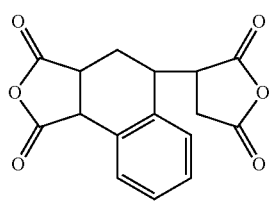

(E-22) 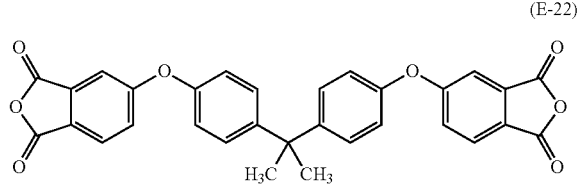

(E-23) 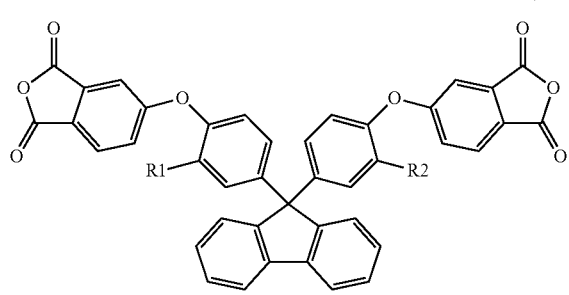

(E-24) 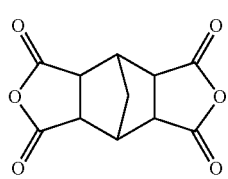

(E-25) 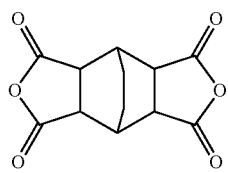

(E-26) 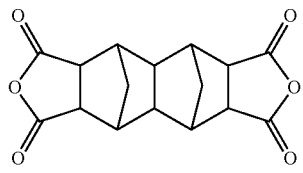

(E-27) 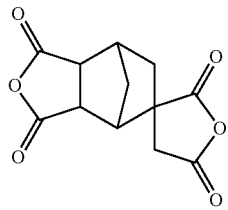

-continued (E-28) 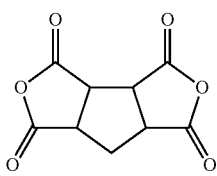

In the formula, R1 and R2 are an alkyl group, an alkoxy group, or a halogen atom.

Further, in the case where the polyamic acid as the polymer compound precursor is synthesized so that the compound before alignment process contains two types of structures that are a structure containing the group shown in Formula (1) and a structure containing a crosslinkable functional group as R2 in Formula (3), for example, a diamine compound and a tetracarboxylic acid dianhydride are selected as follows. That is, at least one of the compounds having a crosslinkable functional group shown in Formula (A-1) to Formula (A-15), at least one of the compounds shown in Formula (C-1) to Formula (C-20), and at least one of the tetracarboxylic acid dianhydride shown in Formula (E-1) to Formula (E-28) are used.

Further, in the case where the polyamic acid as the polymer compound precursor is synthesized so that the compound before alignment process contains two types of structures that are a structure containing the group shown in Formula (2) and a structure containing a crosslinkable functional group as R2 in formula (3), for example, a diamine compound and a tetracarboxylic acid dianhydride are selected as follows. That is, at least one of the compounds having a crosslinkable functional group shown in Formula (A-1) to Formula (A-15), at least one of the compounds shown in Formula (D-1) to Formula (D-7), and at least one of the tetracarboxylic acid dianhydride shown in Formula (E-1) to Formula (E-28) are used.

The content of the compound before alignment process or the polymer compound precursor as the compound before alignment process in the alignment film material is preferably from 1 wt % to 30 wt % both inclusive, and more preferably from 3 wt % to 10 wt % both inclusive. Further, the alignment film material may be mixed with a photopolymerization initiator or the like according to needs.

The TFT substrate 20 and the CF substrate 30 are respectively coated or printed with the prepared alignment film material so that the pixel electrode 20B, the slit section 21, and the opposed electrode 30B are covered therewith, and then heat treatment is provided. Heat treatment temperature is preferably 80 deg C. or more, and more preferably from 150 deg C. to 200 deg C. both inclusive. Further, in the heat treatment, heating temperature may be changed in stages. Thereby, the solvent contained in the coated or printed alignment film material is evaporated, and the alignment films 22 and 32 containing the polymer compound (compound before alignment process) having a crosslinkable functional group as a side chain are formed. After that, rubbing or the like may be provided according to needs.

Figure 4:
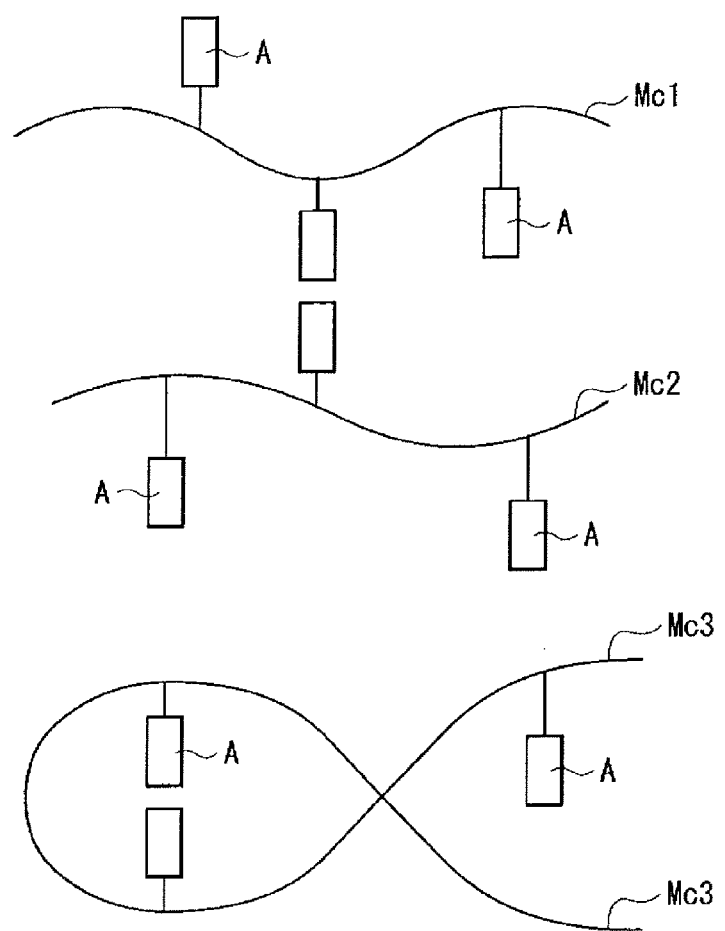
FIG. 4 is a schematic view illustrating a state of a polymer compound (compound before alignment process) in an alignment film for explaining the method of manufacturing the liquid crystal display unit illustrated in FIG. 1.

In this case, the compound before alignment process in the alignment films 22 and 32 may be in the state illustrated in FIG. 4. That is, the compound before alignment process contains main chains Mc (Mc1 to Mc3) and crosslinkable functional groups A introduced as a side chain into the main chains Mc. The main chains Mc1 to Mc3 are not linked. The crosslinkable functional groups A in this state are oriented randomly by thermal motion.

Next, the TFT substrate 20 and the CF substrate 30 are arranged so that the alignment film 22 and the alignment film 32 are opposed to each other, and the liquid crystal layer 40 containing the liquid crystal molecules 41 is sealed between the alignment film 22 and the alignment film 32 (step S102). Specifically, a spacer projection for securing a cell gap such as plastic beads is dispersed toward one of the faces on which the alignment films 22 and 32 are formed of the TFT substrate 20 and the CF substrate 30, and a seal section is printed by using an epoxy adhesive or the like by screen print process. After that, as illustrated in FIG. 5, the TFT substrate 20 and the CF substrate 30 are bonded to the spacer projection and the seal section in between so that the alignment films 22 and 32 are opposed to each other, and a liquid crystal material containing the liquid crystal molecules 41 is injected. After that, the seal section is cured by heating or the like, and thereby the liquid crystal material is sealed between the TFT substrate 20 and the CF substrate 30. FIG. 5 illustrates a cross sectional structure of the liquid crystal layer 40 sealed between the alignment films 22 and 32.

Next, as illustrated in FIG. 6, a voltage V1 is applied between the pixel electrode 20B and the opposed electrode 30B by using a voltage application means 1 (step S103). The voltage V1 is, for example, from 5 volt to 30 volt both inclusive. Thereby, electric field (electric voltage) is generated in a direction making a predetermined angle in relation to the surface of the glass substrates 20A and 30A, and the liquid crystal molecules 41 are aligned at a tilt in a predetermined direction from the direction vertical to the glass substrates 20A and 30A. That is, the orientation angle (deviation angle) of the liquid crystal molecules 41 is determined by the direction of the electric field, and the polar angle (zenith angle) is determined by electric field intensity. The tilt angle of the liquid crystal molecules 41 is approximately equal to the pretilt $\theta1$ that is given to the liquid crystal molecule 41A retained in the alignment film 22 in the vicinity of the interface with the alignment film 22 and the pretilt $\theta2$ that is given to the liquid crystal molecule 41B retained in the alignment film 32 in the vicinity of the interface with the alignment film 32 in the after-mentioned step. Thus, by adjusting the value of the voltage V1 as appropriate, the values of the pretilt $\theta1$ and the pretilt $\theta2$ of the liquid crystal molecules 41A and 41B are able to be controlled.

Further, as illustrated in FIG. 7(A), in a state that the voltage V1 is continuously applied, energy line (specifically, ultraviolet UV) is irradiated to the alignment films 22 and 32, for example, from the outside of the TFT substrate 20. That is, ultraviolet is irradiated to the liquid crystal layer while electric field or magnetic field is applied so that the liquid crystal molecules 41 are aligned in a direction diagonal to the surface of the pair of substrates 20 and 30. Thereby, the crosslinkable functional group contained in the compound before alignment process in the alignment films 22 and 32 is reacted, and the compound before alignment process is cross-linked (step S104). Accordingly, a legitimate response direction of the liquid crystal molecules 41 is stored by the compound after alignment process, and pretilt is given to the liquid crystal molecules 41 in the vicinity of the alignment films 22 and 32. In the result, the polymer after alignment process is formed in the alignment films 22 and 32. The pretilt $\theta1$ and the pretilt $\theta2$ are given to the liquid crystal molecules 41A and 41B located in the vicinity of the interface with the alignment films 22 and 32 in the liquid crystal layer 40 in a non-driving state. As ultraviolet UV, ultraviolet containing a large amount of optic element with a wavelength of about 365 nm is preferable. In the case where the ultraviolet containing a large amount of optic element in short wavelength range is used, there is a possibility that the liquid crystal molecules 41 are photodegraded and deteriorated. In this case, ultraviolet UV is irradiated from the outside of the TFT substrate 20. However, ultraviolet UV may be irradiated from the outside of the CF substrate 30, or ultraviolet UV may be irradiated from the outside of both the TFT substrate 20 and the CF substrate 30. In this case, ultraviolet UV is preferably irradiated from the substrate side with higher transmittance. Further, in the case where ultraviolet UV is irradiated from the outside of the CF substrate 30, there is a possibility that the ultraviolet UV is absorbed by the color filter and cross-linking reaction is hardly generated depending on the wavelength range of the ultraviolet UV. Thus, ultraviolet UV is preferably irradiated from outside of the TFT substrate 20 (substrate side having the pixel electrode).

Figure 7B:
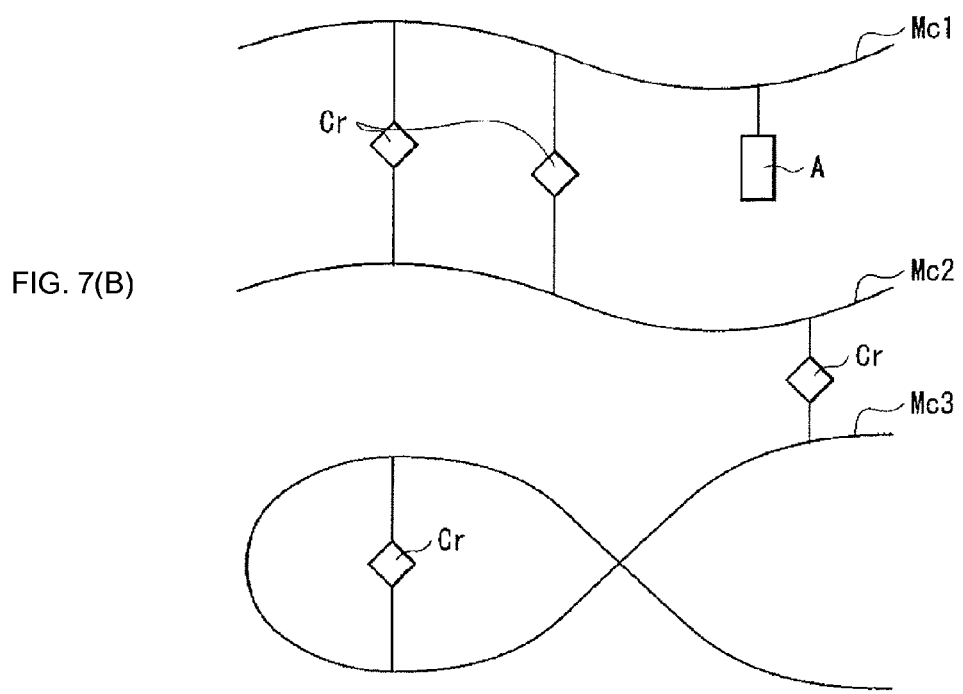
FIG. 7B is a schematic view illustrating a state of a polymer compound (compound after alignment process) in an alignment film.

In this case, the compound after alignment process in the alignment films 22 and 32 is in the state illustrated in FIG. 7(B). That is, the direction of the crosslinkable functional groups A introduced into the main chains Mc of the compound before alignment process is changed according to the alignment direction of the liquid crystal molecules 41, the crosslinkable functional groups A that are physically close to each other are reacted with each other, and accordingly a connection section Cr is formed. Due to the compound after alignment process generated as above, the alignment films 22 and 32 give the pretilt $\theta1$ and the pretilt $\theta2$ to the liquid crystal molecules 41A and 41B. The connection section Cr may be formed among the compound before alignment process, or may be formed in the compound before alignment process. That is, as illustrated in FIG. 7(B), the connection section Cr may be formed between the crosslinkable functional group A of the compound before alignment process having the main chain Mc1 and the crosslinkable functional group A of the compound before alignment process having the main chain Mc2. Further, the connection section Cr may be formed by reacting the crosslinkable functional groups A introduced into the same main chain Mc3 as in the polymer compound having the main chain Mc3.

By the foregoing steps, the liquid crystal display unit (liquid crystal display device) illustrated in FIG. 1 was able to be completed.

In operation of the liquid crystal display unit (liquid crystal display device), in the selected pixel 10, in the case where a drive voltage is applied, alignment state of the liquid crystal molecules 41 included in the liquid crystal layer 40 is changed according to the potential difference between the pixel electrode 20B and the opposed electrode 30B. Specifically, in the liquid crystal layer 40, in the case where a state is changed from the state before applying a drive voltage illustrated in FIG. 1 to a state that a drive voltage is applied, the liquid crystal molecules 41A and 41B located in the vicinity of the alignment films 22 and 32 fall over in its direction, and such operation is transmitted to the other liquid crystal molecules 41C. In the result, the liquid crystal molecules 41 respond to take a stance to be approximately horizontal (parallel) to the TFT substrate 20 and the CF substrate 30. Thereby, optical characteristics of the liquid crystal layer 40 are changed, incident light to the liquid crystal display device becomes modulated output light, gradation sequence is expressed based on the output light, and thereby an image is displayed.

In a liquid crystal display device not given with pretilt process and a liquid crystal display unit including the same, even if an alignment regulation section such as a slit section for regulating alignment of liquid crystal molecules is provided on a substrate, in the case where a drive voltage is applied, the liquid crystal molecules aligned in the direction vertical to the substrate falls so that the director thereof is oriented in a predetermined direction in the in-plane direction of the substrate. As described above, in the liquid crystal molecules responsive to the drive voltage, the orientation of the director of each liquid crystal molecule varies, and the entire alignment is disarrayed. Thereby, the response rate is decreased, and the response characteristics are deteriorated. In the result, there is a problem that the display characteristics are deteriorated. Further, in the case where an initial drive voltage is set to a higher value than a drive voltage in a display state to drive the device (overdriving), when the initial drive voltage is applied, responsive liquid crystal molecules and almost non-responsive liquid crystal molecules exist. The director slope of the responsive liquid crystal molecules is largely different from the director slope of the almost non-responsive liquid crystal molecules. If the drive voltage in a display state is subsequently applied, the director slope of the liquid crystal molecules that responded when the initial drive voltage is applied becomes a director slope corresponding to the drive voltage in a display state and such a slope is transmitted to other liquid crystal molecules, before such operation is transmitted to other liquid crystal molecules. In the result, luminance of the entire pixel reaches luminance in a display state when the initial drive voltage is applied. However, the luminance is subsequently decreased, and reaches the luminance in a state of display again. That is, there is a problem as follows. If overdriving is performed, apparent response rate becomes faster than that of a case in which overdriving is not performed, but sufficient display quality is hardly obtained. Such a problem is hardly generated in IPS mode or FFS mode liquid crystal display devices, and may be a problem unique to the VA mode liquid crystal display device.

Meanwhile, in the liquid crystal display unit (liquid crystal display device) and the method of manufacturing the same of the first embodiment, the foregoing alignment films 22 and 32 give the pretilt θ1 and the pretilt θ2 to the liquid crystal molecules 41A and 41B. Thereby, the problem initiated in the case where pretilt process is never provided is hardly generated, the response rate to a drive voltage is largely improved, and the display quality in overdriving is improved. In addition, since at least one of the TFT substrate 20 and the CF substrate 30 is provided with the slit section 21 or the like as an alignment regulation section for regulating alignment of the liquid crystal molecules 41, display characteristics such as view angle characteristics are secured. Accordingly, the response characteristics are improved in a state that favorable display characteristics are retained.

Further, in the existing method of manufacturing a liquid crystal display unit (light alignment film technology), an alignment film is formed by radiating linear polarized light or light in a direction diagonal to the substrate face (hereinafter referred to as "diagonal light") to a precursor film containing a predetermined polymer material provided on the substrate face, and thereby pretilt process is provided. Thus, there is a problem that a major light radiation equipment such as an equipment for radiating linear polarized light and an equipment for radiating diagonal light is necessitated in forming the alignment film. Further, there is a problem that for forming a pixel having a multidomain for realizing a wider view angle, a more major equipment is necessitated, and the manufacturing steps become complicated. In particular, in the case where the alignment film is formed by using diagonal light, if a structure such as a spacer or irregularity exist on the substrate, a region which is hidden behind the structure or the like and at which diagonal light does not arrive is generated, and desirable alignment regulation for the liquid crystal molecules is difficult in such a region. In this case, for example, in order to radiate diagonal light by using a photo mask for providing a multidomain in a pixel, it is necessary to design the pixel considering light diffraction. That is, in the case where the alignment film is formed by using diagonal light, there is a problem that a high definition pixel is hardly formed.

Further, out of the existing light alignment film technologies, in the case where a crosslinkable polymer compound is used as a polymer material, a crosslinkable functional group contained in the crosslinkable polymer compound in a precursor film is oriented (directed) randomly by thermal motion. Thus, possibility that physical distance between each crosslinkable functional group becomes low. In addition, in the case where random light (non-polarized light) is irradiated, physical distance between each crosslinkable functional group becomes small and thus reaction is initiated. However, for the crosslinkable functional group whose reaction is initiated by radiating straight polarized light, the polarized direction and the direction of the reaction region should be aligned in a predetermined direction. Further, since the radiation area of diagonal light is wider than that of vertical light, the radiation amount per unit area thereof is decreased. That is, the ratio of the crosslinkable functional group responsive to linear polarized light or diagonal light is lower than that in the case where random light (non-polarized light) is irradiated in the direction vertical to the substrate face. Thus, the crosslink density (cross-linking degree) in the formed alignment film is easily decreased.

Meanwhile, in the first embodiment, after the alignment films 22 and 32 containing the compound before alignment process are formed, the liquid crystal layer 40 is sealed between the alignment film 22 and the alignment film 32. Next, by applying a voltage to the liquid crystal layer 40, the alignment of the liquid crystal molecules 41 becomes predetermined alignment, direction of the crosslinkable functional group is arrayed by the liquid crystal molecules 41 (that is, direction of the end structure section of the side chain to the substrate or the electrode is determined by the liquid crystal molecules 41), and the compound before alignment process in the alignment films 22 and 32 is cross-linked. Thereby, the alignment films 22 and 32 that give pretilt θ to the liquid crystal molecules 41A and 41B are able to be formed. That is, according to the liquid crystal display unit (liquid crystal display device) and the method of manufacturing the same of the first embodiment, the response characteristics are able to be easily improved without using a major equipment. In addition, in bridging the compound before alignment process, pretilt θ is able to be given to the liquid crystal molecules 41 without depending on the ultraviolet radiation direction. Thus, a high definition pixel is able to be formed. Further, the compound after alignment process is formed in a state that the direction of the crosslinkable functional groups has been already arrayed in the compound before alignment process. Thus, the cross-linking degree of the compound after alignment process may be higher than that of the alignment film formed by the foregoing existing manufacturing method. Thus, even after long time driving, new cross-linking structures are hardly formed in driving. Therefore, the pretilt θ1 and the pretilt θ2 in the liquid crystal molecules 41A and 41B are able to be retained in a state of manufacturing, and reliability is able to be improved.

In this case, in the first embodiment, after the liquid crystal layer 40 is sealed between the alignment films 22 and 32, the compound before alignment process in the alignment films 22 and 32 is cross-linked. Thus, the transmittance in driving the liquid crystal display device is able to be continuously increased.

Figure 9A:
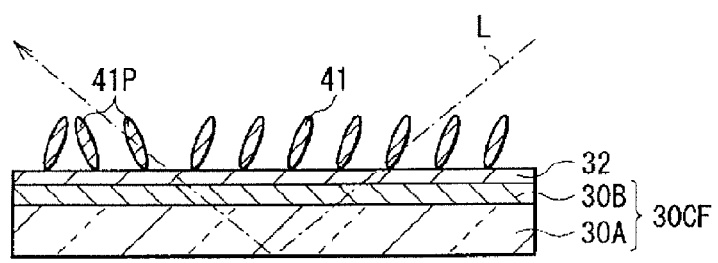
FIGS. 9(A) AND 9(B) are cross sectional schematic views for explaining order parameter.

More specifically, in the case where the existing light alignment film technology is used, as illustrated in FIG. 9(A), part of diagonal light L irradiated for providing pretilt process is reflected by the rear face of the glass substrate 30. Thus, in part of the liquid crystal molecules 41 (41P), pretilt direction is disarrayed. In this case, since the pretilt direction of the part of the liquid crystal molecules 41 is deviated from pretilt direction of the other liquid crystal molecules 41, order parameter as an index expressing alignment state of the liquid crystal molecules 41 (expressing how uniform the alignment state is) is decreased. Thereby, in the initial driving of the liquid crystal display device, the partial liquid crystal molecules 41P with the deviated pretilt direction show behavior different from that of the other liquid crystal molecules 41, the partial liquid crystal molecules 41P are aligned in a direction different from that of the other liquid crystal molecules 41, and the transmittance becomes increased. However, the partial liquid crystal molecules 41P are subsequently aligned in the same direction as that of the other liquid crystal molecules 41. Thus, after director direction of the temporarily tilted liquid crystal molecules 41P becomes vertical to the substrate face, the director direction of the liquid crystal molecules 41P is aligned with the director direction of the other liquid crystal molecules 41. Therefore, there is a possibility that the transmittance of the liquid crystal device is not continuously increased, but is locally decreased.

Figure 9B:
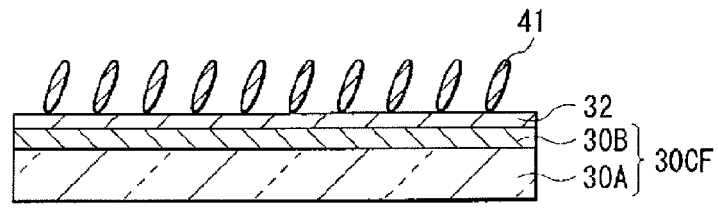

Meanwhile, in the first embodiment in which pretilt process is provided by cross-linking reaction of the compound before alignment process after the liquid crystal layer 40 is sealed, pretilt is given according to alignment direction of the liquid crystal molecules 41 by the alignment regulation section for regulating alignment of the liquid crystal molecules 41 such as the slit section 21. Thus, as illustrated in FIG. 9(B), the pretilt direction of the liquid crystal molecules 41 is easily aligned, and thus the order parameter is increased (becomes close to 1). Thereby, in driving the liquid crystal display device, the liquid crystal molecules 41 show uniform behavior. Thus, transmittance is continuously increased.

In this case, in particular, in the case where the compound before alignment process has the group shown in Formula (1) together with the crosslinkable functional group, or the compound before alignment process has the group shown in Formula (2) as the crosslinkable functional group, the alignment films 22 and 32 more easily give pretilt θ. Thus, the response rate is able to be more improved.

Further, in another existing method of manufacturing a liquid crystal display device, after a liquid crystal layer is formed by using a liquid crystal material containing a monomer or the like having photopolymerization characteristics, in a state that the monomer is contained, while predetermined alignment of the liquid crystal molecules in the liquid crystal layer is provided, light is irradiated to polymerize the monomer. A resultant polymer formed as above gives the liquid crystal molecules with pretilt. However, in the manufactured liquid crystal display device, there is a problem that an unreacted photopolymerizable monomer remains in the liquid crystal layer, and reliability is lowered. Further, to decrease the amount of the unreacted monomer, it is necessary to increase light radiation time, resulting in a problem that time (takt time) necessary for manufacture is increased.

Meanwhile, in the first embodiment, even if the liquid crystal layer is not formed by using the liquid crystal material added with the monomer as described above, the alignment films 22 and 32 give the pretilt θ1 and the pretilt θ2 to the liquid crystal molecules 41A and 41B in the liquid crystal layer 40. Thus, reliability is able to be improved. Further, takt time is able to be inhibited from being increased. Further, without using the existing technology for giving pretilt to liquid crystal molecules such as rubbing, the pretilt θ is able to be favorably given to the liquid crystal molecules 41A and 41B. Thus, contrast lowering caused by a flaw in the alignment film generated by rubbing, breaking of wire caused by static charge in rubbing, lowering of reliability or the like caused by foreign matters that are problematic factors in rubbing are not generated.

In the first embodiment, the description has been given of the case that the alignment films 22 and 32 containing the compound before alignment process having a main chain mainly containing a polyimide structure are used. However, the main chain contained in the compound before alignment process is not limited to the compound containing a polyimide structure. For example, the main chain may contain a polysiloxane structure, a polyacrylate structure, a polymethacrylate structure, a maleimide polymer structure, a styrene polymer structure, a styrene maleimide polymer structure, a polysaccharide structure, a polyvinyl alcohol structure or the like. Specially, a compound before alignment process having a main chain containing a polysiloxane structure is preferable. Further, glass transition temperature Tg of the compound structuring a main chain is desirably 200 deg C. or more, since thereby effect similar to that of the polymer compound containing the foregoing polyimide structure is able to be obtained. Examples of the compound before alignment process having a main chain mainly containing a polysiloxane structure include the polymer compound containing a polysilane structure shown in Formula (9). R10 and R11 in Formula (9) are arbitrary as long as R10 and R11 are a monovalent group containing carbon. One of R10 and R11 preferably contains a crosslinkable functional group as a side chain, since thereby sufficient alignment regulation ability is easily obtained in the compound after alignment process. Examples of the crosslinkable functional group in this case include the group shown in the foregoing Formula (41).

(9)

In the formula, R10 an R11 represent a monovalent organic group, and ml represents an integer number of 1 or more.

Further, in the first embodiment, the slit section 21 is provided in the pixel electrode 20B, and thereby alignment division is realized to improve view angle characteristics. However, the method of improving view angle characteristics is not limited to the slit section 21 provided in the pixel electrode 20B. For example, instead of the slit section 21, a projection as an alignment regulation section may be provided between the pixel electrode 20B and the alignment film 22. By providing such a projection, effect similar to that in the case of providing the slit section 21 is able to be obtained. Further, a projection as an alignment regulation section may be also provided between the opposed electrode 30B and the alignment film 32 of the CF substrate 30. In this case, the projection on the TFT substrate 20 and the projection on the CF substrate 30 are arranged not to be opposed to each other between the substrates. In this case, effect similar to that of the foregoing case is able to be obtained.

Next, a description will be given of the other embodiments. For the same elements as those of the first embodiment, the same referential symbols are affixed thereto and the description thereof will be omitted. Further, action and effect similar to those of the first embodiment will be omitted as appropriate. Further, the various technical contents described in the first embodiment will be applied to the other embodiments as appropriate.

Second Embodiment

A second embodiment is a modified embodiment of the first embodiment. In the first embodiment, the description has been given of the liquid crystal display unit (liquid crystal display device) in which the alignment films 22 and 32 are formed so that the pretilt θ1 and the pretilt θ2 of the liquid crystal molecules 41A and 41B located in the vicinity of the alignment films 22 and 32 are almost the same. In the second embodiment, the pretilt θ1 value is different from the pretilt θ2 value.

Specifically, in the second embodiment, first, the TFT substrate 20 having the alignment film 22 and the CF substrate 30 having the alignment film 32 are formed in the same manner as that of the foregoing step S101. Next, for example, an ultraviolet absorber is contained in the liquid crystal layer 40 and is sealed. Subsequently, a predetermined voltage is applied between the pixel electrode 20B and the opposed electrode 30B, ultraviolet is irradiated from the TFT substrate 20 side, and thereby the compound before alignment process in the alignment film 22 is cross-linked. At this time, since the ultraviolet absorber is contained in the liquid crystal layer 40, the ultraviolet entering from the TFT substrate 20 side is absorbed by the ultraviolet absorber in the liquid crystal layer 40, and hardly reaches the CF substrate 30 side. Thus, in the alignment film 22, the compound after alignment process is generated. Subsequently, a voltage different from the foregoing predetermined voltage is applied between the pixel electrode 20B and the opposed electrode 30B, ultraviolet is irradiated from the CF substrate 30 side, and thereby the compound before alignment process in the alignment film 32 is reacted to form the compound after alignment process. Thereby, according to the voltage applied in radiating ultraviolet from the TFT substrate 20 side and the voltage applied in radiating ultraviolet from the CF substrate 30 side, the pretilt θ1 and the pretilt θ2 of the liquid crystal molecules 41A and 41B located in the vicinity of the alignment films 22 and 32 are able to be set. Thus, the pretilt θ1 value is able to be different from the pretilt θ2 value. However, the TFT substrate 20 is provided with a TFT switching device and various bus lines, and various transverse electric fields are generated in driving. Accordingly, it is desirable that the alignment film 22 on the TFT substrate 20 side is formed so that the pretilt θ1 of the liquid crystal molecules 41A located in the vicinity of the alignment film 22 is larger than the pretilt θ2 of the liquid crystal molecules 41B located in the vicinity of the alignment film 32. Thereby, alignment disarray of the liquid crystal molecules 41A caused by the transverse electric fields is able to be effectively decreased.

Third Embodiment

Figure 10:
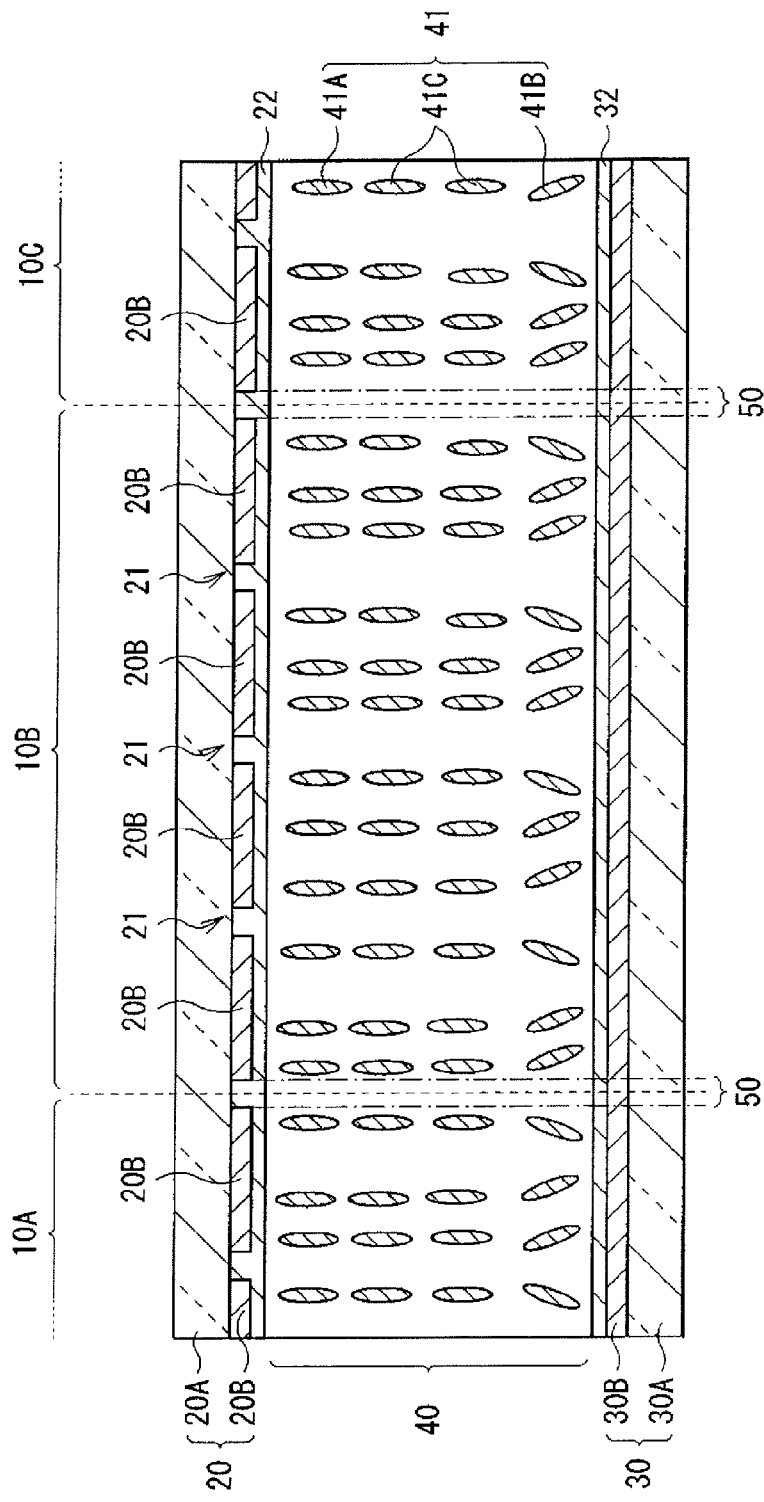
FIG. 10 is a schematic partial cross sectional view of a modified example of the liquid crystal display unit of the present invention.

A third embodiment is a modified embodiment of the first embodiment and the second embodiment. FIG. 10 illustrates a schematic partial cross sectional view of a liquid crystal display unit (liquid crystal display device) according to the third embodiment. Differently from the first embodiment, in the third embodiment, the alignment film 22 does not contain the compound after alignment process. That is, in the third embodiment, the pretilt θ2 of the liquid crystal molecules 41B located in the vicinity of the alignment film 32 has a higher value than 0 deg, while the pretilt θ1 of the liquid crystal molecules 41A located in the vicinity of the alignment film 22 is 0 deg.

In this case, the alignment film 22 includes, for example, the foregoing other vertical aligner.

Figure 3:
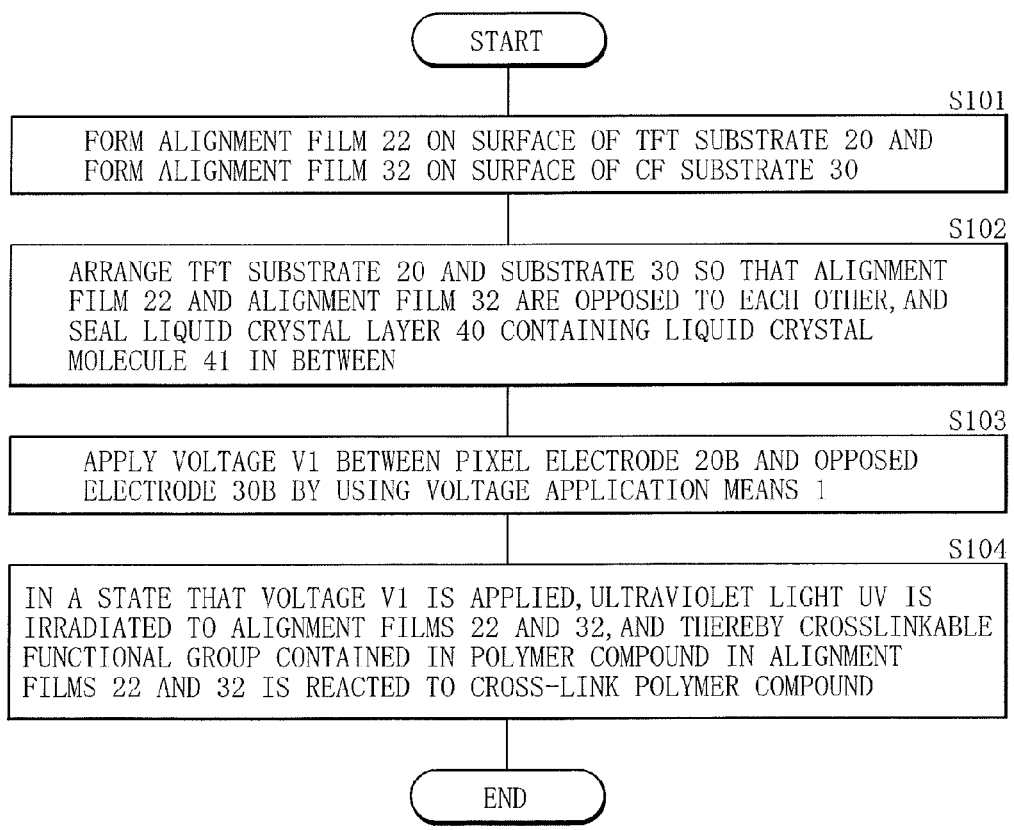
FIG. 3 is a flowchart for explaining a method of manufacturing the liquid crystal display unit illustrated in FIG. 1.

The liquid crystal display unit (liquid crystal display device) of the third embodiment is able to be manufactured by using the foregoing other vertical aligner instead of the compound before alignment process or the polymer compound precursor as the compound before alignment process in forming the alignment film 22 on the TFT substrate 20 (step S101 of FIG. 3).

In the liquid crystal display unit (liquid crystal display device) of the third embodiment, in the liquid crystal layer 40, the pretilt θ1 of the liquid crystal molecules 41A is 0 deg, and the pretilt θ2 of the liquid crystal molecules 41B is larger than 0 deg. Thereby, compared to a liquid crystal display unit not provided with pretilt process, response rate to a drive voltage is able to be largely improved. Further, since the liquid crystal molecules 41A are aligned in a direction close to the normal line of the glass substrates 20A and 30A, the light transmission amount in black display is able to be decreased and contrast is able to be improved compared to the liquid crystal display units (liquid crystal display devices) of the first embodiment and the second embodiment. That is, in this liquid crystal display unit (liquid crystal display device), for example, contrast is improved by setting the pretilt θ1 of the liquid crystal molecules 41A located on the TFT substrate 20 side to 0 deg while response rate is able to be improved by setting the pretilt θ2 of the liquid crystal molecules 41B located on the CF substrate 30 side to a larger value than 0 deg. Accordingly, the response rate to a drive voltage and the contrast are able to be improved with a proper balance.

Further, according to the liquid crystal display unit (liquid crystal display device) and the method of manufacturing the same of the third embodiment, the alignment film 22 not containing the compound before alignment process is formed on the TFT substrate 20, and the alignment film 32 containing the compound before alignment process is formed on the CF substrate 30. Next, after the liquid crystal layer 40 is sealed between the TFT substrate 20 and the CF substrate 30, the compound before alignment process in the alignment film 32 is reacted to synthesize the compound after alignment process. Thus, the alignment film 32 that gives the pretilt θ to the liquid crystal molecules 41B is able to be formed without using a major light radiation equipment, and thus response characteristics are able to be improved easily. Further, compared to a case that a photopolymerizable monomer is polymerized after the liquid crystal layer is sealed by using a liquid crystal material containing a photopolymerizable monomer, higher reliability is able to be secured.

Other effects of the third embodiment are similar to those of the first embodiment.

Figure 11:
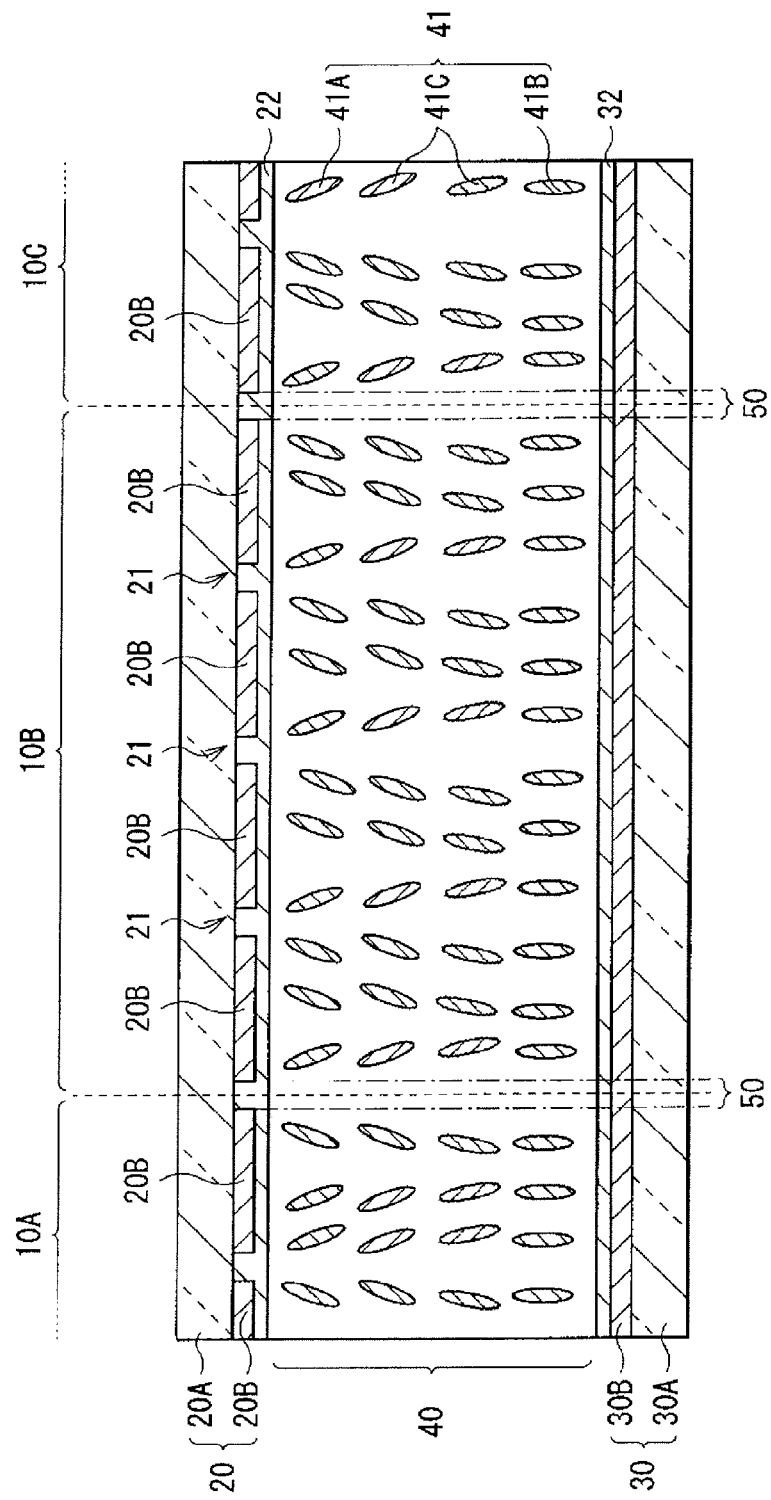
FIG. 11 is a schematic partial cross sectional view of a modified example of the liquid crystal display unit illustrated in FIG. 10.

Further, in the third embodiment, as illustrated in FIG. 10, the alignment film 32 covering the CF substrate 30 contains the compound after alignment process and gives the pretilt $\theta 2$ to the liquid crystal molecules 41B located on the CF substrate 30 side out of the liquid crystal layer 40, but structure is not limited thereto That is, as illustrated in FIG. 11, it is possible that the alignment film 32 does not contain the compound after alignment process, the alignment film 22 covering the TFT substrate 20 contains the compound after alignment process and gives the pretilt $\theta 1$ to the liquid crystal molecules 41A located on the TFT substrate 20 side out of the liquid crystal layer 40. In this case, action and effect similar to those of the third embodiment are able to be obtained. However, as described above, in the TFT substrate 20, various transverse electric fields are generated in driving. Accordingly, it is desirable that the alignment film 22 on the TFT substrate 20 side is formed to give the pretilt $\theta 1$ to the liquid crystal molecules 41A located in the vicinity thereof. Thereby, alignment disarray of the liquid crystal molecules 41 caused by the transverse electric fields is able to be effectively decreased.

Fourth Embodiment

Figure 12:
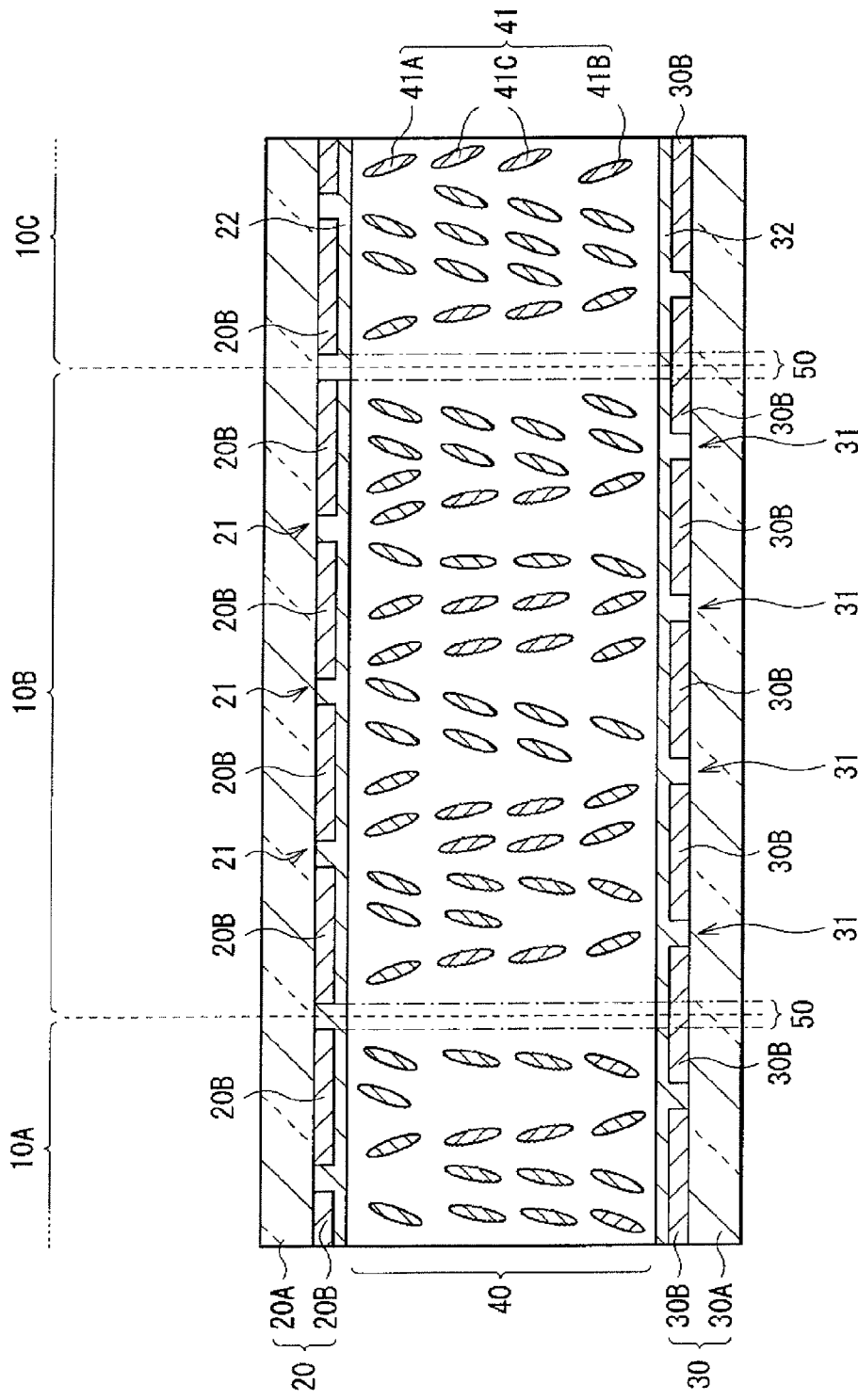
FIG. 12 is a schematic partial cross sectional view of another modified example of the liquid crystal display unit of the present invention.

A fourth embodiment is also a modified embodiment of the first embodiment and the second embodiment. FIG. 12 illustrates a schematic partial cross sectional view of a liquid crystal display unit (liquid crystal display device) according to the fourth embodiment. The fourth embodiment has a structure similar to that of the liquid crystal display units (liquid crystal display devices) of the first embodiment and the second embodiment, except that the structure of the opposed electrode 30B included in the CF substrate 30 is different.

Specifically, the opposed electrode 30B is provided with the slit section 31 having a pattern similar to that of the pixel electrode 20B in each pixel. The slit section 31 is arranged not to opposed to the slit section 21 between the substrates. Thereby, in the case where a drive voltage is applied, diagonal electric field is given to the director of the liquid crystal molecule 41. Thereby, response rate to the voltage is improved, a region where alignment direction is different is formed in each pixel (alignment division), and thus view angle characteristics are improved.

The liquid crystal display unit (liquid crystal display device) of the fourth embodiment is able to be manufactured by using a substrate provided with the opposed electrode 30B having a predetermined slit section 31 on the color filter of the glass substrate 30A as the CF substrate 30 in step S101 of FIG. 3.

According to the liquid crystal display unit (liquid crystal display device) and the method of manufacturing the same of the fourth embodiment, after the alignment films 22 and 32 containing the polymer compound before cross-link are formed, the liquid crystal layer 40 is sealed between the alignment film 22 and the alignment film 32. Next, the polymer compound before cross-link in the alignment films 22 and 32 is reacted to generate the cross-linked polymer compound. Thereby, predetermined pretilts $\theta 1$ and $\theta 2$ are given to the liquid crystal molecules 41A and 41B. Thus, compared to a liquid crystal display unit not provided with pretilt process, response rate to a drive voltage is able to be largely improved. Thus, the alignment films 22 and 32 that gives the pretilt $\theta$ to the liquid crystal molecules 41 are able to be formed without using a major equipment. Accordingly, the response characteristics are able to be easily improved. Further, compared to a case that, for example, pretilt process is provided by sealing the liquid crystal layer by using a liquid crystal material containing a photopolymerizable monomer and subsequently polymerizing the photopolymerizable monomer, higher reliability is able to be secured.

Action and effect of the liquid crystal display unit (liquid crystal display device) and the method of manufacturing the same of the fourth embodiment are similar to the foregoing action and the foregoing effect of the first embodiment and the second embodiment.

Further, in the fourth embodiment, the alignment films 22 and 32 are formed to give the pretilt $\theta 1$ and the pretilt $\theta 2$ to the liquid crystal molecules 41A and 41B located in the vicinity thereof. However, the pretilt $\theta$ may be given to the liquid crystal molecules 41 located in the vicinity of one of the alignment films 22 and 32 by using a method similar to the manufacturing method described in the third embodiment. In this case, action and effect similar to those of the third embodiment are able to be obtained as well.

Fifth Embodiment

In the first embodiment to the fourth embodiment, the compound before alignment process is reacted in at least one of the alignment films 22 and 32 in a state that the liquid crystal layer 40 is provided to generate the compound after alignment process, and thereby pretilt is given to the liquid crystal molecules 41 located in the vicinity thereof. Meanwhile, in the fifth embodiment, the polymer compound structure is deformed in at least one of the alignment films 22 and 32 in a state that the liquid crystal layer 40 is provided, and thereby pretilt is given to the liquid crystal molecules 41 located in the vicinity thereof. That is, the liquid crystal display unit (liquid crystal display device) of the fifth embodiment has a structure similar to that of the foregoing first embodiment to the foregoing fourth embodiment, except that the method of forming the alignment films 22 and 32 is different.

In the case where the liquid crystal molecules 41A and 41B have the predetermined pretilt $\theta 1$ and the pretilt $\theta 2$, the liquid crystal display unit (liquid crystal display device) of the fifth embodiment is manufactured, for example, as follows. First, the alignment films 22 and 32 containing the polymer compound such as the foregoing other vertical aligner are formed on the TFT substrate 20 and the CF substrate 30. Next, the TFT substrate 20 and the CF substrate 30 are arranged so that the alignment film 22 and the alignment film 32 are opposed to each other, and the liquid crystal layer 40 is sealed between the alignment film 22 and the alignment film 32. Next, a voltage is applied between the pixel electrode 20B and the opposed electrode 30B. In a state that the voltage is continuously applied, ultraviolet UV containing a larger amount of optic element in short wavelength range of about wavelength 250 nm than that of the foregoing ultraviolet UV is irradiated to the alignment films 22 and 32. At this time, due to the ultraviolet UV in the short wavelength range, the polymer compound in the alignment films 22 and 32 is, for example, deformed and thereby the structure is changed. Thereby, the predetermined pretilt $\theta 1$ and the predetermined pretilt $\theta 2$ are able to given to the liquid crystal molecules 41A located in the vicinity of the alignment film 22 and the liquid crystal molecules 41B located in the vicinity of the alignment films 32.

Examples of the polymer compound contained in the alignment films 22 and 32 before sealing the liquid crystal layer 40 include a polymer compound having a polyimide structure shown in Formula (10). As shown in the chemical reaction formula of Formula (I), in the case where the cyclobutane structure in Formula (10) is cleaved by radiating the ultraviolet UV, the polyimide structure shown in Formula (10) becomes a structure shown in Formula (11).

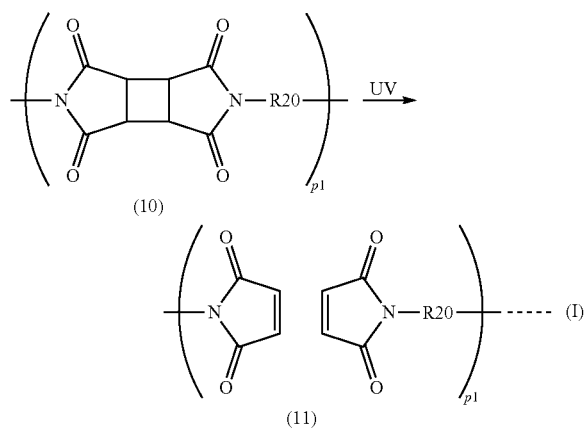

In the formula, R20 represents a bivalent organic group, and p1 represents an integer number of 1 or more.

In the fifth embodiment, since the liquid crystal molecules 41A located in the vicinity of the alignment film 22 and the liquid crystal molecules 41B located in the vicinity of the alignment films 32 have the predetermined pretilt θ1 and the predetermined pretilt θ2, compared to a liquid crystal display unit not provided with pretilt process, response rate is able to be largely improved. Further, at least one of the alignment films 22 and 32 capable of giving the pretilt θ to the liquid crystal molecules 41 is able to be formed without using a major equipment. Accordingly, the response characteristics are able to be easily improved. However, there is a possibility that the liquid crystal molecules 41 are, for example, deformed by ultraviolet irradiated to the alignment films 22 and 32. Thus, higher reliability is able to be secured in the first embodiment to the fourth embodiment.

Sixth Embodiment

A sixth embodiment relates to the liquid crystal display unit according to the second aspect of the present invention, and methods of manufacturing a liquid crystal display unit according to a second aspect and the third aspect of the present invention.

In the first embodiment to the fourth embodiment, the compound after alignment process is obtained by bridging a crosslinkable functional group in the compound before alignment process having the crosslinkable functional group as a side chain. Meanwhile, in the sixth embodiment, the compound after alignment process is obtained based on the compound before alignment process having a photosensitive functional group deformed by radiating energy line as a side chain.

In the sixth embodiment, the alignment films 22 and 32 contain one or more polymer compounds (compound after alignment process) having a cross-linked structure in a side chain as well. The liquid crystal molecules are given with pretilt by the deformed compound. In this case, the compound after alignment process is generated by forming the alignment films 22 and 32 containing one or more polymer compounds (compound before alignment process) having a main chain and a side chain, subsequently providing the liquid crystal layer 40, and then deforming the polymer compound or radiating energy line to the polymer compound, or more specifically, by deforming the photosensitive functional group contained in the side chain while applying electric field or magnetic field. Such a state is illustrated in the conceptual diagram of FIG. 16. In FIG. 16, the direction of the arrow affixed with "UV" and the direction of the arrow affixed with "voltage" do not indicate the direction of irradiated ultraviolet and the direction of the applied electric field. The compound after alignment process contains a structure in which the liquid crystal molecules are arranged in a predetermined direction (specifically diagonal direction) to the pair of substrates (specifically, the TFT substrate 20 and the CF substrate 30). As described above, the compound after alignment process is contained in the alignment films 22 and 32, by deforming the polymer compound, or by radiating energy line to the polymer compound, the liquid crystal molecule 41 in the vicinity of the alignment films 22 and 32 is able to be given with pretilt. Accordingly, the response rate becomes increased, and the display characteristics are improved.

As the photosensitive functional group, an azobenzene compound having an azo group, a compound having imine and aldimine as a skeleton (referred to as "aldimine benzene" as a matter of convenience), and a compound having a styrene skeleton (referred to as "stilbene" as a matter of convenience) are able to be exemplified. These compounds respond to energy line (for example, ultraviolet) and are deformed, that is, a state of these compounds is shifted from trans state to cis state. In the result, pretilt is able to be given to the liquid crystal molecules.

Aldimine Benzene

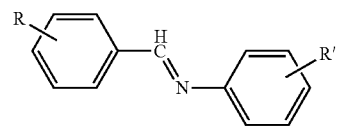

Stilbene

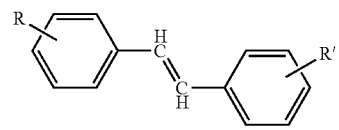

As "x" in an azobenzene compound shown in Formula (AZ-0), specifically, for example, the following Formulas (AZ-1) to (AZ-9) are able to be exemplified.

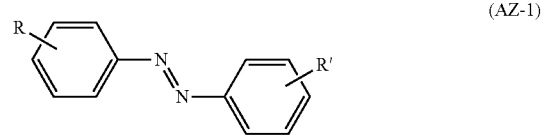

-continued (AZ-2)
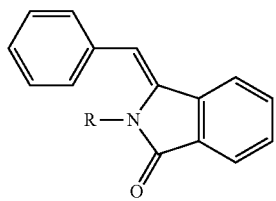

(AZ-3)
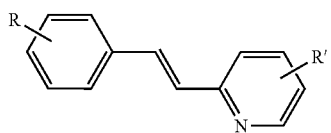

(AZ-4)
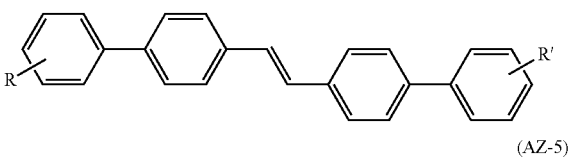

(AZ-5)
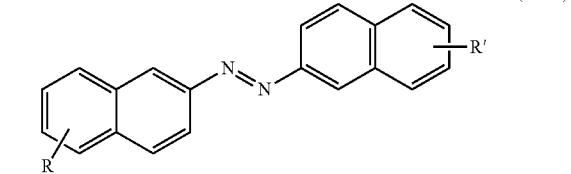

(AZ-6)

(AZ-7)
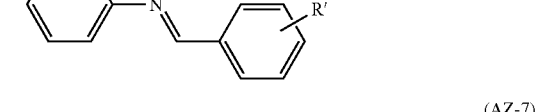

(AZ-8)
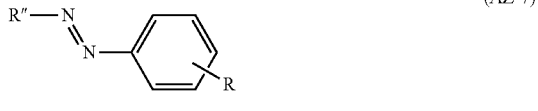

(AZ-9)
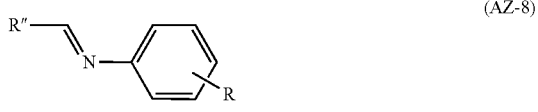

In the formula, one of R and R" is bonded to a benzene ring containing diamine, and the other becomes an end group. R, R', and R" represent a hydrogen atom, a halogen atom, an alkyl group, an alkoxy group, and a monovalent group having a carbonate group, or a derivative thereof. R" is directly bonded to a benzene ring containing diamine.

The liquid crystal display unit and the method of manufacturing the same of the sixth embodiment are similar to the liquid crystal display unit and the method of manufacturing the same described in the first embodiment to the fourth embodiment fundamentally and substantially, except that the compound before alignment process having a photosensitive functional group deformed by radiating energy line (specifically, ultraviolet) is used. Thus, detailed description thereof will be omitted.

Example 1

Example 1A

Example 1 relates to the liquid crystal display unit (liquid crystal display device) and the method of manufacturing the same according to the first aspect of the present invention, and the method of manufacturing a liquid crystal display unit (liquid crystal display device) according to the third aspect of the present invention. In Example 1A, the liquid crystal display unit (liquid crystal display device) illustrated in FIG. 11 was formed by the following procedure.

First, the TFT substrate 20 and the CF substrate 30 were prepared. As the TFT substrate 20, a substrate including the pixel electrode 20B including ITO having a slit pattern (slit section 21 with a line width of 60 μm and a line space of 10 μm) on one face side of the glass substrate 20A having a thickness of 0.7 mm was used. Further, as the CF substrate 30, a substrate including the opposed electrode 30B including ITO having a slit pattern (slit section 31 with a line width of 60 μm and a line space of 10 μm) on a color filter of the glass substrate 30A having a thickness of 0.7 mm in which the color filter was formed was used. Due to the slit pattern formed in the pixel electrode 20B and the opposed electrode 30B, diagonal electric field was added between the TFT substrate 20 and the CF substrate 30. Subsequently, a 3.5 μm spacer projection was formed on the TFT substrate 20.

Meanwhile, an alignment film material was prepared. In this case, first, 1 mol of a compound having the crosslinkable functional group shown in Formula (A-7) as a diamine compound, 1 mol of a compound having the vertical alignment induction structure section shown in Formula (B-6), and 2 mol of the tetracarboxylic acid dianhydride shown in Formula (E-2) were dissolved in N-methyl-2-pyrrolidone (NMP). Subsequently, the solution was reacted for 6 hours at 60 deg C. After that, a largely excessive pure water was poured into the reacted solution to precipitate a reaction product. Subsequently, after the precipitated solid was separated, the solid was washed with pure water and dried for 15 hours at 40 deg C. under reduced pressure. Thereby, polyamic acid as a polymer compound precursor as the compound before alignment process was synthesized. Finally, 3.0 gram of obtained polyamic acid was dissolved in NMP, and thereby a solution with a solid concentration of 3 wt % was obtained. After that, the resultant was filtrated with a 0.2 μm filter.

Subsequently, the TFT substrate 20 and the CF substrate 30 were respectively coated with the prepared alignment film material by using a spin coater. After that, the coated film was dried for 80 seconds with the use of a hot plate at 80 deg C. Subsequently, the TFT substrate 20 and the CF substrate 30 were heated for 1 hour in an oven at 200 deg C. under nitrogen gas atmosphere. Thereby, alignment films 22 and 32 having a thickness of 80 nm (800 Å) on the pixel electrode 20B and the opposed electrode 30B were formed.

Subsequently, a seal section was formed by coating peripheral edge of the pixel section on the CF substrate 30 with an ultraviolet cured resin containing silica particles having a particle diameter of 3.5 μm. A liquid crystal material including MLC-7029 (Merck make) as a negative liquid crystal was dropped into a section surrounded by the seal section. After that, the TFT substrate 20 and the CF substrate 30 were bonded to each other so that the center of the line section of the pixel electrode 20B and the slit section 31 of the opposed electrode 30B were opposed to each other to cure the seal section. Subsequently, the resultant was heated for 1 hour in an oven at 120 deg C. to totally cure the seal section. Thereby, the liquid crystal layer 40 was sealed to complete the liquid crystal cell.

Subsequently, in a state that a rectangular wave AC electric field (60 Hz) of an actual value voltage 10 volt was applied to the liquid crystal cell formed as above, uniform ultraviolet of 500 mJ (measurement at wavelength of 365 nm) was irradiated thereto to react the compound before alignment process in the alignment films 22 and 32. Thereby, the alignment films 22 and 32 containing the compound after alignment process were formed for both the TFT substrate 20 and the CF substrate 30. Accordingly, the liquid crystal display unit (liquid crystal display device) illustrated in FIG. 12 in which the liquid crystal molecule 41A and 41B on the TFT substrate 20 and the CF substrate 30 side are given with pretilt was able to be completed. Finally, a pair of polarization plates were attached to the outside of the liquid crystal display unit so that each absorption axis was perpendicular to each other.

Example 1B

In Example 1B, a procedure similar to that of Example 1A was taken, except that instead of polyamic acid, an imide polymer obtained by providing polyamic acid with dehydration ring closure was used as an alignment film material. At this time, the polyamic acid synthesized in Example 1A was dissolved in N-methyl-2-pyrrolidone, to which pyridine and acetic anhydride were subsequently added. The mixed solution was reacted for 3 hours at 110 deg C. to provide dehydration ring closure. Subsequently, a largely excessive pure water was poured into the reacted mixed solution to precipitate a reaction product. After the precipitated solid was separated, the solid was washed with pure water. After that, the resultant was dried for 15 hours at 40 deg C. under reduced pressure. Thereby, an imide polymer as the compound before alignment process was obtained.

Example 1C

In Example 1C, a procedure similar to that of Example 1A was taken, except that in synthesizing polyamic acid, a compound having a vertical alignment induction structure section shown in the following Formula (B-37) was used instead of a compound having the vertical alignment induction structure section shown in the following Formula (B-6).

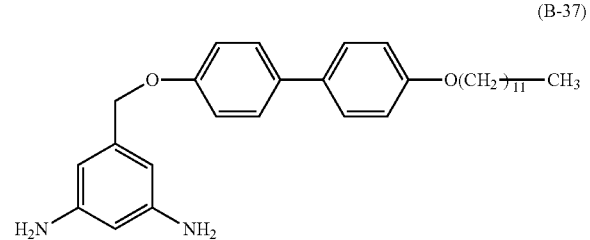

(B-37)

Example 1D

In Example 1D, a procedure similar to that of Example 1A was taken, except that in synthesizing polyamic acid, the tetracarboxylic acid dianhydride shown in Formula (E-3) was used instead of the tetracarboxylic acid dianhydride shown in Formula (E-2).

Example 1E

In Example 1E, a procedure similar to that of Example 1A was taken, except that in synthesizing polyamic acid, the tetracarboxylic acid dianhydride shown in Formula (E-1) was used instead of the tetracarboxylic acid dianhydride shown in Formula (E-2).

Example 1F

In Example 1F, a procedure similar to that of Example 1A was taken, except that in synthesizing polyamic acid, a compound having the crosslinkable functional group shown in Formula (A-7) was not used as a diamine compound and ultraviolet irradiated to the liquid crystal cell was changed. More specifically, in synthesizing polyamic acid, 2 mol of a compound having the vertical alignment induction structure section shown in Formula (B-6) was used as a diamine compound. Further, in a state that a rectangular wave AC electric field of an actual value voltage 10 volt was applied to the liquid crystal cell, uniform ultraviolet of 100 mJ (measurement at wavelength of 250 nm) was irradiated thereto.

Comparative Example 1A

In Comparative example 1A, a procedure similar to that of Example 1A was taken, except that ultraviolet was not irradiated to the liquid crystal cell.

Comparative Example 1B

In Comparative example 1B, a procedure similar to that of Example 1F was taken, except that ultraviolet was irradiated to the liquid crystal cell was changed to uniform ultraviolet of 500 mJ (measurement at wavelength of 365 nm).

For the liquid crystal display units (liquid crystal display devices) of Example 1A to Example 1F and Comparative example 1A and Comparative example 1B, response time was measured. Accordingly, the result illustrated in FIG. 13 was obtained. In measuring the response time, a drive voltage (from 2.5 volt to 7.5 volt both inclusive) was applied between the pixel electrode 20B and the opposed electrode 30B by using LCD5200 (Otsuka electronics Co. Ltd. make) as a measurement equipment, and time until when luminance 10% was changed to luminance 90% of gradient according to the drive voltage thereof was measured.

Figure 13:
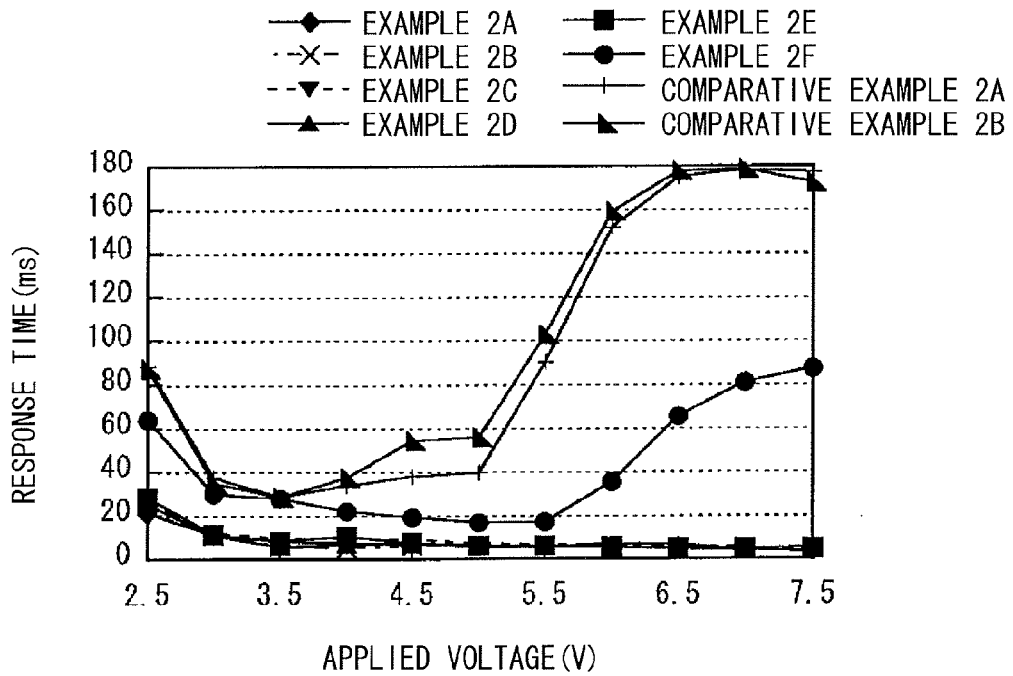
FIG. 13 is a characteristics diagram illustrating a relation between an applied voltage and response time in Example 1.

As illustrated in FIG. 13, in Example 1A to Example 1E in which the alignment films 22 and 32 contained the polymer compound (compound after alignment process) having a polyimide structure together with the cross-linking structure, response time was shortened compared to Comparative example 1A and Comparative example 1B in which the side chain did not contain cross-linked polyimide. Further, in Example 1F in which the alignment films 22 and 32 gave the pretilt θ1 and the pretilt θ2 to the liquid crystal molecules 41A and 41B by decomposing polyimide, response time was longer than that of Example 1A to Example 1E, but shortened than that of Comparative example 1A and Comparative example 1B having the alignment films 22 and 32 in which polyimide was not deformed.

That is, in Example 1A to Example 1F, the alignment films 22 and 32 were formed so that the pretilt θ1 and the pretilt θ2 were given to the liquid crystal molecules 41A and 41B, and liquid crystal alignment characteristics were favorable. Meanwhile, in Comparative example 1A and Comparative example 1B, the alignment films 22 and 32 similar to that of Example 1A to Example 1F were not formed.

Accordingly, in the VA mode liquid crystal display unit (or liquid crystal display device), in a state that the liquid crystal layer 40 was provided, the compound before alignment process in the alignment films 22 and 32 was cross-linked or the polymer compound structure was deformed so that the alignment films 22 and 32 gave pretilt θ to the liquid crystal molecules 41 in the vicinity thereof. Thereby, response rate was able to be largely improved. In this case, it was confirmed that the alignment films 22 and 32 capable of giving pretilt to the liquid crystal molecules 41A and 41B were able to be formed without using a major equipment. Thus, it was confirmed that response characteristics were able to be improved easily.

Reference Example 1A

Next, an alignment film was formed by the following procedure to examine a crosslink density. That is, the alignment film was formed by using the alignment film material of Example 1A. In this case, first, the surface on one face side of the glass substrate was coated with the alignment film material used in Example 1A (polyamic acid solution with a solid concentration of 3 wt %) by using a spin coater. After that, the coated film was dried for 80 seconds with the use of a hot plate at 80 deg C. After that, the glass substrate was heated for 1 hour in an oven at 200 deg C. under nitrogen gas atmosphere. Thereby, an alignment film (precursor film) having a thickness of 80 nm (800 Å) containing the compound before alignment process was formed. Subsequently, uniform ultraviolet (random light) of 500 mJ (measurement at wavelength of 365 nm) was irradiated from the alignment film side of the glass substrate to react the compound before alignment process in the precursor film. Thereby, the alignment film containing the compound after alignment process was formed.

Reference Example 1B

A procedure similar to that of Reference example 1A was taken, except that in radiating ultraviolet, polarized light of 500 mJ (measurement at wavelength of 365 nm) was irradiated instead of random light.

For the alignment films of Reference example 1A and Reference example 1B, crosslink density was measured. Accordingly, the result illustrated in Table 1 was obtained.

In measuring the crosslink density, infrared spectrum of the alignment film was measured by using a reflective FT-IR (Nicoletnexus 470FT-IR, Thermo Fisher Scientific Co. make). At this time, first, infrared spectrum (reflection) was measured for the alignment film (precursor film) before radiating ultraviolet. Based on the spectrum, an area of absorption peak in wave number of 1642 cm-1 (absorption peak area in the precursor film) was calculated. The absorption peak in the wave number of 1642 cm-1 was originated from stretching vibration of carbon double bond (C=C) subject to cross-linking reaction of the crosslinkable functional group (chalcone group) introduced into polyimide. Subsequently, infrared spectrum was measured for the alignment film after radiating ultraviolet in the same manner as the foregoing method. Based on the spectrum, an area of absorption peak in wave number of 1642 cm-1 (absorption peak area in the alignment film after radiating ultraviolet) was calculated. Based on these absorption peak areas before and after radiating ultraviolet, crosslink density (%)=[1− (absorption peak area in the alignment film after radiating ultraviolet/absorption peak area in the precursor film)]*100 was calculated.

TABLE 1

| | Ultraviolet (outside light) [Peak wavelength: 365 nm] | | Crosslink |
|---|---|---|---|
| | Type | Radiation amount (milli J) | density (%) |
| Reference example 1A | Random light | 500 | 71.2 |
| Reference example 1B | Polarized light | 500 | 47.7 |

As illustrated in Table 1, in Reference example 1A in which random light was irradiated, the crosslink density was 71.2% which was significantly higher than that of Reference example 1B in which polarized light was irradiated with a crosslink density of 47.7%. The result showed the following. In the precursor film, the crosslinkable functional group was oriented (directed) in a random direction by thermal motion. At this time, in the case where random light (non-polarized light) was irradiated, when physical distance between each crosslinkable functional group became small by thermal motion, reaction was initiated and a side chain was cross-linked. However, in the case where polarized light was irradiated, due to thermal motion, the polarized direction and the direction of the reaction region (C=C bond where cross-linking reaction was initiated in a chalcone group) were aligned in a predetermined direction. In addition, in the case where physical distance between each crosslinkable functional group became small, reaction was initiated and a side chain was cross-linked. Thus, in the case where random light was used as ultraviolet for bridging, the crosslink density in the alignment film was higher than that in the case of using polarized light.

Accordingly, it was confirmed that in the case where the alignment film containing a polymer compound having a cross-linking structure was formed by ultraviolet radiation, by using random light as ultraviolet, the crosslink density was able to be increased. Thus, it was suggested that in the liquid crystal display unit (liquid crystal display device) including the alignment film having a higher crosslink density formed as above, reliability was improved.

Example 2

Example 2A

Example 2 also relates to the liquid crystal display unit (liquid crystal display device) and the method of manufacturing the same according to the first aspect of the present invention, and the method of manufacturing a liquid crystal display unit (liquid crystal display device) according to the third aspect of the present invention. Differently from in Example 1A, in Example 2A, the liquid crystal display unit (liquid crystal display device) illustrated in FIG. 1 was formed and response characteristics were examined.

Specifically, first, the TFT substrate 20 and the CF substrate 30 were prepared. As the TFT substrate 20, a substrate in which the pixel electrode 20B including ITO having a slit pattern (slit section 21 with a line width of 4 μm and a line space of 4 μm) on one face side of the glass substrate 20A having a thickness of 0.7 mm was used. Further, as the CF substrate 30, a substrate in which the opposed electrode 30B including ITO was formed over the whole area of a color filter of the glass substrate 30A having a thickness of 0.7 mm in which the color filter was formed was used. Due to the slit pattern formed in the pixel electrode 20B, diagonal electric field was added between the TFT substrate 20 and the CF substrate 30. Subsequently, a 3.5 μm spacer projection was formed on the TFT substrate 20 by using photosensitive acrylic resin PC-335 (JSR Co. make).

Meanwhile, an alignment film material was prepared. In this case, first, a compound having the crosslinkable functional group shown in Formula (A-8) as a diamine compound, a compound having the vertical alignment induction structure section shown in Formula (B-6), the compound shown in Formula (C-1), and the tetracarboxylic acid dianhydride shown in Formula (E-2) were dissolved in NMP at a ratio illustrated in Table 2. Subsequently, the solution was reacted for 4 hours at 60 deg C. After that, a largely excessive methanol was poured into the reacted solution to precipitate a reaction product. Subsequently, after the precipitated solid was separated, the solid was washed with methanol and dried for 15 hours at 40 deg C. under reduced pressure. Thereby, polyamic acid as a polymer compound precursor as the compound before alignment process was synthesized. Finally, 3.0 gram of obtained polyamic acid was dissolved in NMP, and thereby a solution with a solid concentration of 3 wt % was obtained. After that, the resultant was filtrated with a 0.2 μm filter.

Subsequently, the TFT substrate 20 and the CF substrate 30 were respectively coated with the prepared alignment film material by using a spin coater. After that, the coated film was dried for 80 seconds with the use of a hot plate at 80 deg C. Subsequently, the TFT substrate 20 and the CF substrate 30 were heated for 1 hour in an oven at 200 deg C. under nitrogen gas atmosphere. Thereby, the alignment films 22 and 32 having a thickness of 90 nm on the pixel electrode 20B and the opposed electrode 30B were formed.

Subsequently, as in Example 1A, a seal section was formed by coating peripheral edge of the pixel section on the CF substrate 30 with an ultraviolet cured resin. A liquid crystal material including a negative liquid crystal was dropped into a section surrounded by the seal section. After that, the TFT substrate 20 and the CF substrate 30 were bonded to each other to cure the seal section. Subsequently, the resultant was heated for 1 hour in an oven at 120 deg C. to totally cure the seal section. Thereby, the liquid crystal layer 40 was sealed to complete the liquid crystal cell.

Subsequently, in a state that a rectangular wave AC electric field (60 Hz) of an actual value voltage 10 volt was applied to the liquid crystal cell formed as above, uniform ultraviolet of 500 mJ (measurement at wavelength of 365 nm) was irradiated to react the compound before alignment process in the alignment films 22 and 32. Thereby, the alignment films 22 and 32 containing the compound after alignment process were formed in both the TFT substrate 20 and the CF substrate 30. Accordingly, the liquid crystal display unit (liquid crystal display device) illustrated in FIG. 1 in which the liquid crystal molecule 41A and 41B on the TFT substrate 20 and the CF substrate 30 side were given with pretilt was able to be completed. Finally, a pair of polarization plates was attached to the outside of the liquid crystal display unit so that each absorption axis was perpendicular to each other.

Example 2B

In Example 2B, a procedure similar to that of Example 2A was taken, except that in synthesizing polyamic acid, a compound having the vertical alignment induction structure section shown in Formula (B-6) was not used.

Example 2C

In Example 2C, a procedure similar to that of Example 2A was taken, except that in synthesizing polyamic acid, the compound shown in Formula (C-2) was used instead of the compound shown in Formula (C-1).

Example 2D and Example 2E

In Example 2D and Example 2E, a procedure similar to that of Example 2A was taken, except that in synthesizing polyamic acid, a compound having the group shown in Formula (D-7) and a compound shown in Formula (G-1) were used at a ratio illustrated in Table 2 were used instead of a compound having the crosslinkable functional group shown in Formula (A-8), a compound having the vertical alignment induction structure section shown in Formula (B-6), and the compound shown in Formula (C-1).

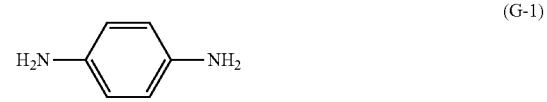

(G-1)

Comparative Example 2

In Comparative example 2, a procedure similar to that of Example 2A was taken, except that in synthesizing polyamic acid, a compound having the vertical alignment induction structure section shown in Formula (B-6) was used instead of a compound having the group shown in Formula (D-7).

For the liquid crystal display units (liquid crystal display devices) of Example 2A to Example 2E and Comparative example 2, the pretilt θ and response time were measured. Accordingly, the result illustrated in Table 2 was obtained.

In examining the pretilt θ of the liquid crystal molecules 41, measurement was performed by crystal rotation method using He—Ne laser light based on a known method (the method described in J. Appl. Phys., vol. 19, p. 2013, 1980, T. J. Scheffer et al.). In the after-mentioned various examples and comparative examples, the method of measuring the pretilt θ was the same as such a method. As described above and illustrated in FIG. 2, the pretilt θ was a tilt angle of the director D of the liquid crystal molecules 41 (41A and 41B) to Z direction in a state that a drive voltage is off where a direction perpendicular to the surface of the glass substrates 20A and 30A (normal line direction) is Z.

In measuring the response time, a drive voltage (7.5 volt) was applied between the pixel electrode 20B and the opposed electrode 30B by using LCD5200 (Otsuka electronics Co. Ltd. make) as a measurement equipment, and time until when luminance 10% was changed to luminance 90% of gradient according to the drive voltage thereof was measured. In the after-mentioned various examples and comparative examples, the method of measuring the response time was the same as such a method.

TABLE 2

| | Material of alignment film (mol ratio: %) | Pretilt θ deg | Response rate millisecond |
|---|---|---|---|
| Example 2A | Formula (A-8):Formula (B-6):Formula (C-1):Formula (E-2) = 12.5:2.5:35:50 | 0.2 | 50.5 |
| Example 2B | Formula (A-8):Formula (C-1):Formula (E-2) = 32.5:17.5:50 | 0.4 | 19.2 |
| Example 2C | Formula (A-8):Formula (B-6):Formula (C-2):Formula (E-2) = 32.5:2.5:15:50 | 0.5 | 18.3 |
| Example 2D | Formula (D-7):Formula (F-1):Formula (E-2) = 25:25:50 | 0.4 | 17.2 |
| Example 2E | Formula (D-7):Formula (F-1):Formula (E-2) = 12.5:37.5:50 | 0.5 | 17.1 |
| Comparative example 2 | Formula (B-6):Formula (F-1):Formula (E-2) = 2.5:47.5:50 | 0.0 | 115.0 |

As illustrated in Table 2, in Example 2A to Example 2E in which the compound after alignment process in the alignment films 22 and 32 contained a compound having the group shown in Formula (1) or Formula (2), the pretilt θ was given and response time was shortened, compared to Comparative example 2 not containing such a compound.

That is, in Example 2A to Example 2E, the alignment films 22 and 32 were formed to give the pretilt θ1 and the pretilt θ2 to the liquid crystal molecules 41A and 41B, and liquid crystal alignment characteristics were favorable. Meanwhile, in Comparative example 2, the alignment films 22 and 32 similar to that of Example 2A to Example 2E were not formed.

Accordingly, in the VA mode liquid crystal display unit (or liquid crystal display device), it was confirmed that the compound after alignment process in the alignment films 22 and 32 contained a polymer having the group shown in Formula (1) or Formula (2), the pretilt θ was able to be given and response rate was able to be largely improved.

Next, the liquid crystal display unit (liquid crystal display device) illustrated in FIG. 1 was fabricated and transmittance in driving was examined.

Reference Example 2A

In Reference example 2A, a procedure similar to that of Example 2A was taken, except that the pretilt was given as follows. That is, a light alignment film (RN1338, Nissan Chemical Industries make) was formed by using a spin coater on each opposed face side of the TFT substrate 20 and the CF substrate 30. After that, the light alignment film was dried for 80 seconds with the use of a hot plate at 80 deg C. Subsequently, the TFT substrate 20 and the CF substrate 30 were heated for 1 hour in an oven at 200 deg C. under nitrogen gas atmosphere. After that, polarized ultraviolet light is diagonally irradiated to the light alignment film, and thereby pretilt was given.

Reference Example 2B

In Reference example 2B, a procedure similar to that of Example 2A was taken, except that the pretilt was given as follows. That is, a vertical alignment film (JALS2131-R6, JSR Co. make) was formed on each opposed face side of the TFT substrate 20 and the CF substrate 30 by using a spin coater. After that, the vertical alignment film was dried for 80 seconds with the use of a hot plate at 80 deg C. Subsequently, the TFT substrate 20 and the CF substrate 30 were heated for 1 hour in an oven at 200 deg C. under nitrogen gas atmosphere. Subsequently, a seal section was formed by coating peripheral edge of the pixel section on the CF substrate 30 with an ultraviolet cured resin containing silica particles having a particle diameter of 3.5 μm. A liquid crystal material obtained by mixing 0.3 wt % of an acryl monomer (A-BP-2E, Shin-Nakamura Chemical Co., Ltd. make) in MLC-7029 (Merck make) as a negative liquid crystal was dropped into a section surrounded by the seal section. Subsequently, in a state that a rectangular wave AC electric field (60 Hz) of an actual value voltage 10 V was applied, uniform ultraviolet of 500 mJ (measurement at wavelength of 365 nm) was irradiated, and thereby pretilt was given.

For the liquid crystal display units (liquid crystal display devices) of Example 2E, Reference example 2A, and Reference example 2B, transmittance in driving was measured. Accordingly, the result illustrated in FIG. 14 was obtained. In measuring the transmittance, a drive voltage (7.5 volt) was applied between the pixel electrode 20B and the opposed electrode 30B, and light transmittance that was transmitted from the TFT substrate 20 side to the CF substrate 30 side was examined.

Figure 14:
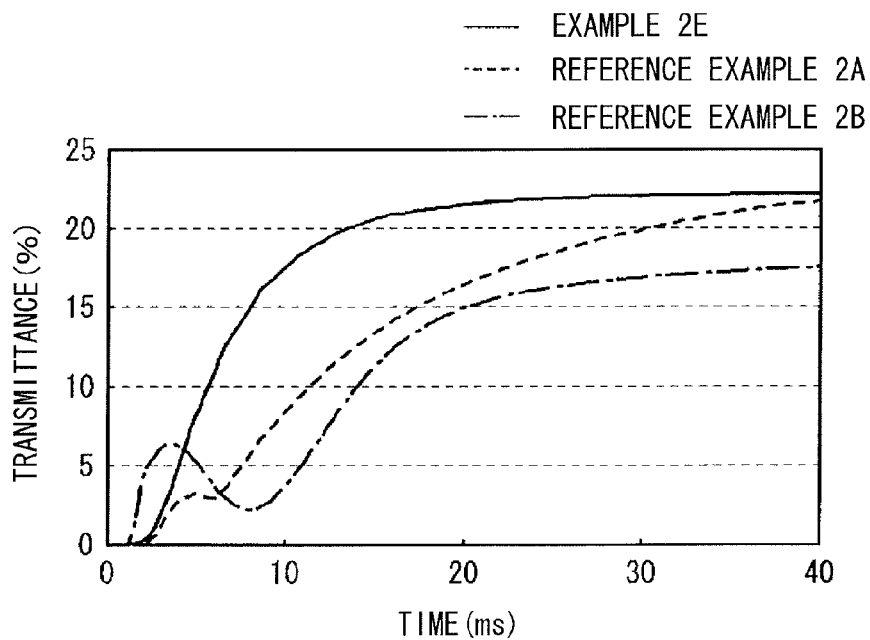
FIG. 14 is a characteristics diagram illustrating a relation between time and transmittance in Example 2.

As illustrated in FIG. 14, in Example 2E in which the alignment films 22 and 32 containing the polymer compound (compound after alignment process) having a cross-linking structure was used, the transmittance was continuously increased. Meanwhile, in Reference example 2A and Reference example 2B in which the foregoing alignment films 22 and 32 were not used, the transmittance was not continuously increased, but the transmittance was increased, once decreased, and again increased.

That is, in Example 2E, since each pretilt direction of the liquid crystal molecules 41 was aligned and order parameter was increased, the transmittance was continuously increased as time advanced. Meanwhile, in Reference example 2A and Reference example 2B, each pretilt direction of the liquid crystal molecules 41 was disarrayed and order parameter was decreased. Thus, the transmittance was decreased along the way as time advanced.

Accordingly, in the VA mode liquid crystal display unit (liquid crystal display device), in a state that the liquid crystal layer 40 was provided, the compound before alignment process in the alignment films 22 and 32 was cross-linked or the polymer compound structure was deformed so that the alignment films 22 and 32 gave the pretilt θ to the liquid crystal molecules 41. Thereby, transmittance was able to be continuously increased. Thus, it was confirmed that response characteristics were able to be improved easily and stably.

Example 3

Example 3A to Example 3R

Example 3 also relates to the liquid crystal display unit (liquid crystal display device) and the method of manufacturing the same according to the first aspect of the present invention, and the method of manufacturing a liquid crystal display unit (liquid crystal display device) according to the third aspect of the present invention. In Example 3A to Example 3R, a polymer compound not having a structure that the liquid crystal molecules were located along the end structure section was set as Comparative example 3, and whether or not response rate was improved in comparison with Comparative example 3 was examined.

Specifically, a diamine compound and a tetracarboxylic acid dianhydride were reacted to obtain polyamic acid. Next, a substance provided with imide reaction and dehydration ring closure was dissolved in NMP. Six types of polyimide shown in Formula (F-1) to Formula (F-6) obtained as above were referred to as Example 3A to Example 3F. Further, the acrylate monomers shown in Formula (F-7) to Formula (F-12) were reacted together with a polymer initiator in MEK. Next, the dried resultant was dissolved in NMP. Six types of polyacrylate obtained as above were referred to as Example 3G to Example 3L. Further, the silanes shown in Formula (F-13) to Formula (F-18) were provided with hydrolytic cleavage, generated silanols were dehydrated and condensed, and the resultant was dissolved in NMP. Six types of polysiloxane obtained as above are referred to as Example 3M to Example 3R.

After the alignment films 22 and 32 were obtained in the same manner as in Example 2A by using Example 3A to Example 3R, a liquid crystal cell was completed based on a method fundamentally similar to that described in Example 2A. However, the height of the spacer projection was 3.5 µm, silica particles having a particle diameter of 3.5 µm was used, and the seal section was formed. Further, the thickness of the alignment films 22 and 32 on the pixel electrode 20B and the opposed electrode 30B was 90 nm.

Next, in a state that a rectangular wave AC electric field (60 Hz) of an actual value voltage 20 volt was applied to the liquid crystal cell formed as above, uniform ultraviolet of 500 mJ (measurement at wavelength of 365 nm) was irradiated to react the compound before alignment process in the alignment films 22 and 32. Thereby, the alignment films 22 and 32 containing the compound after alignment process were formed on both the TFT substrate 20 and the CF substrate 30. Accordingly, the liquid crystal display unit (liquid crystal display device) illustrated in FIG. 1 in which the liquid crystal molecule 41A and 41B on the TFT substrate 20 and the CF substrate 30 side were given with pretilt was able to be completed. Finally, a pair of polarization plates was attached to the outside of the liquid crystal display unit so that each absorption axis was perpendicular to each other.

For the liquid crystal display units (liquid crystal display devices) [Example 3A to Example 3R] fabricated as above, pretilt of the liquid crystal molecules and response rate were measured. The result is illustrated in the following Table 3. The response rate was measured in the same manner as that of Example 2A to Example 2E.

Comparative Example 3

In Comparative example 3, a liquid crystal display unit (liquid crystal display device) was fabricated in the same manner as that of Example 3A, except that a material shown in Formula (G-2) was used, and a material made of the tetracarboxylic acid dianhydride shown in Formula (E-2) was used together with the compound shown in Formula (B-1) having an equivalent molar in relation to the compound shown in Formula (G-2) was used. Pretilt of the liquid crystal molecules and response rate were measured. The result is illustrated in the following Table 3. The material shown in Formula (G-2) does not have a group capable of being located along the liquid crystal molecules 41, and does not have a mesogenic group.

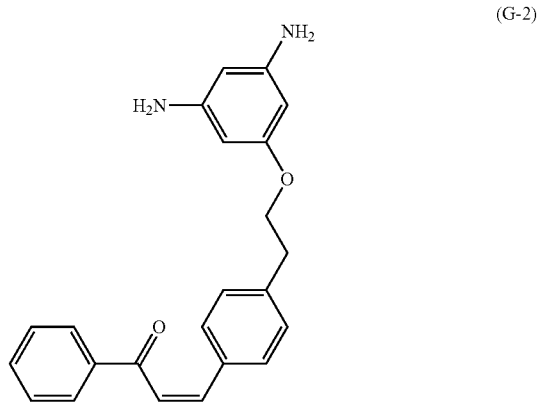 [SMILES: Nc1cc(N)cc(OCCc2ccc(/C=C\C(=O)c3ccccc3)cc2)c1]

(G-2)

TABLE 3

|  | Pretilt θ deg | Response rate millisecond |
|---|---|---|
| Example 3A | 0.9 | 8.73 |
| Example 3B | 1.3 | 9.24 |
| Example 3C | 1.5 | 8.34 |
| Example 3D | 1.1 | 8.55 |
| Example 3E | 1.0 | 8.74 |
| Example 3F | 1.0 | 9.32 |
| Example 3G | 1.1 | 7.24 |
| Example 3H | 1.1 | 7.34 |
| Example 3I | 0.9 | 8.23 |
| Example 3J | 1.2 | 8.99 |
| Example 3K | 1.2 | 9.84 |
| Example 3L | 0.9 | 8.33 |
| Example 3M | 1.0 | 9.43 |
| Example 3N | 1.1 | 8.48 |
| Example 3O | 1.2 | 10.24 |
| Example 3P | 1.3 | 9.29 |
| Example 3Q | 0.9 | 8.74 |
| Example 3R | 0.9 | 7.43 |
| Comparative example 3 | 0.1 | 50.99 |

From Table 3, it was found that in Example 3A to Example 3R, the response rate was significantly higher than that of Comparative example 3.

Example 4

Example 4A to Example 4H

Example 4 also relates to the liquid crystal display unit (liquid crystal display device) and the method of manufacturing the same according to the first aspect of the present invention, and the method of manufacturing a liquid crystal display unit (liquid crystal display device) according to the third aspect of the present invention. In Example 4A to Example 4H, relation between the surface roughness Ra of the alignment film and response rate/contrast was examined.

Specifically, the tetracarboxylic acid dianhydride shown in Formula (E-2) having an equivalent molar in relation to the total number of mols of a diamine compound (ratio between a diamine compound shown in Formula (G-3) and the diamine compound shown in Formula (G-1) was as illustrated in Table 4) was dissolved in NMP. Subsequently, the solution was reacted for 4 hours at 60 deg C., and thereby polyimide was obtained. As a tetracarboxylic acid dianhydride, other tetracarboxylic acid dianhydride shown in Formula (E-1) and Formula (E-3) to Formula (E-28) was able to be used. Next, a largely excessive methanol was poured into the reaction mixture to precipitate a reaction product. After that, the reaction product was washed with methanol and dried for 15 hours at 40 deg C. under reduced pressure. Thereby, polyamic acid was synthesized. The polyamic acid synthesized as above is referred to as an alignment film material a and an alignment film material b illustrated in Table 4 the CF substrate. Accordingly, the liquid crystal display unit (liquid crystal display device) illustrated in FIG. 1 in which the liquid crystal molecule on the TFT substrate and the CF substrate side were given with pretilt was able to be completed. Finally, a pair of polarization plates was attached to the outside of the liquid crystal display unit so that each absorption axis was perpendicular to each other.

Meanwhile, in Comparative example 4A to Comparative example 4L, in the same manner as that of Example 4A to Example 4H, the spacer projection was formed on a TFT substrate having a pixel electrode, while an opposed electrode not being patterned was formed on a CF substrate. Subsequently, each opposed face of the TFT substrate and the CF substrate was respectively spin-coated with a vertical alignment film (AL1H659, JSR Co. Ltd. make), and the resultant was dried for 80 seconds with a hot plate at 80 deg C. Subsequently, the TFT substrate and the CF substrate were heated for 1 hour in an oven at 200 deg C. under

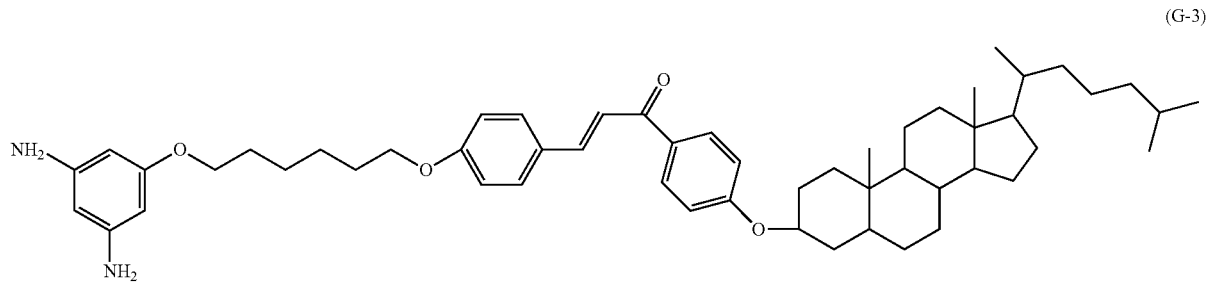 [SMILES: CC(C)CCCC(C)C1CCC2C3CCC4CC(Oc5ccc(C(=O)/C=C/c6ccc(OCCCCCCOc7cc(N)cc(N)c7)cc6)cc5)CCC4(C)C3CCC12C]

(G-3)

TABLE 4

| | Diamine | |
|---|---|---|
| | Formula (G-3) | Formula (G-1) |
| Alignment film material a | 25 | 75 |
| Alignment film material b | 40 | 60 |

In Example 4A to Example 4H, after the alignment films 22 and 32 were obtained in the same manner as in Example 2A, a liquid crystal cell was completed based on a method fundamentally similar to that described in Example 2A. At this time, the height of the spacer projection was 3.5 µm, silica particles having a particle diameter of 3.5 µm was used, and the seal section was formed. Further, the thickness of the alignment films 22 and 32 on the pixel electrode 20B and the opposed electrode 30B was 90 nm. Further, the pixel electrode was patterned so that diagonal electric field was added to the pixel electrode side in which the spacer projection was formed. At this time, the width of the patterned pixel electrode was 4 µm, and a space between the patterned pixel electrode and the pixel electrode was 4 µm. That is, the pixel electrode was patterned in a state of line and space. That is, a line width of the slit pattern was 4 µm and a line space was 4 µm.

Subsequently, in a state that a rectangular wave AC electric field (60 Hz) of an actual value voltage of 2.5 volt to 50 volt both inclusive was applied to the liquid crystal cell formed as above, uniform ultraviolet of 500 mJ (measurement at wavelength of 365 nm) was irradiated to react the compound before alignment process in the alignment film and give pretilt to the liquid crystal molecules 41A and 41B. Thereby, the alignment film containing the compound after alignment process was formed in both the TFT substrate and nitrogen gas atmosphere. Subsequently, a seal section was formed by coating peripheral edge of the pixel section on the CF substrate with an ultraviolet cured resin containing silica particles having a particle diameter of 3.5 µm. A liquid crystal material obtained by mixing acryl monomer (A-BP-2E, Shin-Nakamura Chemical Co., Ltd. make) in MLC-7029 (Merck make) as a negative liquid crystal was dropped into a section surrounded by the seal section. After that, the TFT substrate and the CF substrate were bonded to each other, and the seal section was cured. Subsequently, the resultant was heated for 1 hour in an oven at 200 deg C. to totally cure the seal section. Thereby, the liquid crystal layer was able to be sealed to complete the liquid crystal cell. Next, ultraviolet was irradiated while a voltage was applied to the liquid crystal layer, and thereby the acryl monomer was polymerized Thereby, the polymer projection was formed on the uppermost surface of the alignment film, and the polymer projection gave pretilt to the liquid crystal molecules.

For the liquid crystal display units (liquid crystal display devices) of Example 4A to Example 4H and Comparative example 4A to Comparative example 4L, the surface roughness Ra, the pretilt θ, the response time, and the contrast were measured. Accordingly, the result illustrated in the Table 5 was obtained. In Example 4A to Example 4D, the alignment film material a was used, and the actual value voltage value applied when the compound before alignment process in the alignment film was reacted by radiating ultraviolet was changed. In Example 4E to Example 4H, the alignment film material b was used, and the actual value voltage value applied when the compound before alignment process in the alignment film was reacted by radiating ultraviolet was changed. The relation among the applied actual value voltages was as follows. Meanwhile, the addition amount of acryl monomer was 0.3 wt % in Comparative example 4A to Comparative example 4D, the addition amount of acryl monomer was 0.1 wt % in Comparative example 4E to Comparative example 4H, and the addition amount of acryl monomer was 0.03 wt % in Comparative example 4I to Comparative example 4L. Further, relation among the applied actual value voltages applied when the compound before alignment process in the alignment film was reacted by radiating ultraviolet was as follows.

[Actual Value Voltage]
Example 4A>Example 4B>Example 4C>Example 4D
Example 4E>Example 4F>Example 4G>Example 4H
Comparative example 4A>Comparative example 4B>Comparative example 4C>Comparative example 4D
Comparative example 4H>Comparative example 4G>Comparative example 4F>Comparative example 4E
Comparative example 4I>Comparative example 4J>Comparative example 4K>Comparative example 4L In measuring the surface roughness Ra, the liquid crystal cell was deformed, and measurement was performed by using AFM VN-8000, Keyence Corporation make. At this time, the liquid crystal cell was opened (deformed) so that the alignment film was not damaged, and liquid crystal was carefully washed away from the alignment film surface by using IPA. After that, the resultant was dried in an oven under nitrogen gas atmosphere at 85 deg C. for 10 minutes, and the surface roughness Ra was measured. The contrast was measured in a dark room by using CS-2000, Konica Minolta make.

Figure 17A:
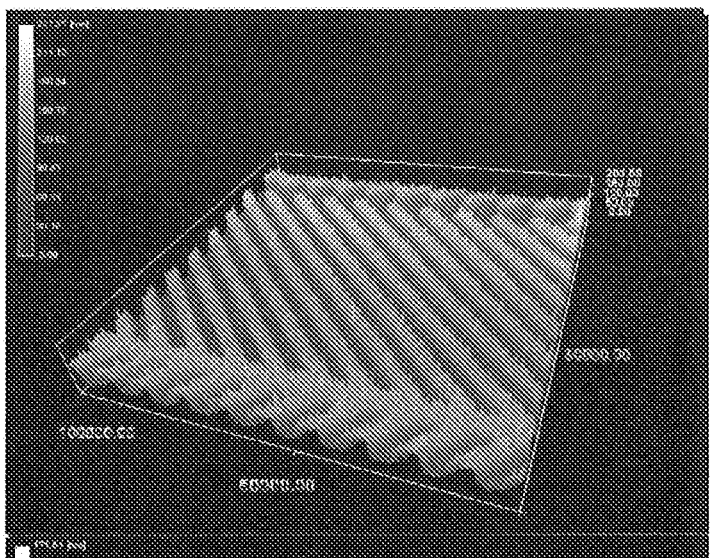
FIG. 17(A), FIG. 17(B), and FIG. 17(C) are AFM images of the surface of alignment films in Example 4A, Comparative example 4A, and Comparative example 4E.
Figure 17B:
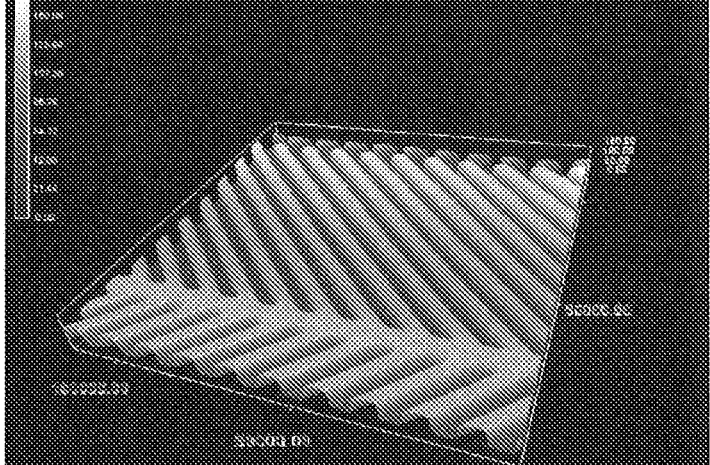
Figure 17C:
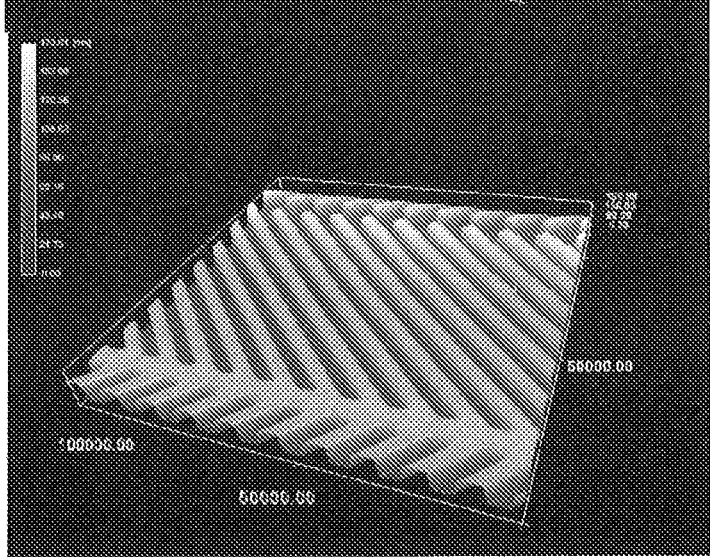
Figure 18:
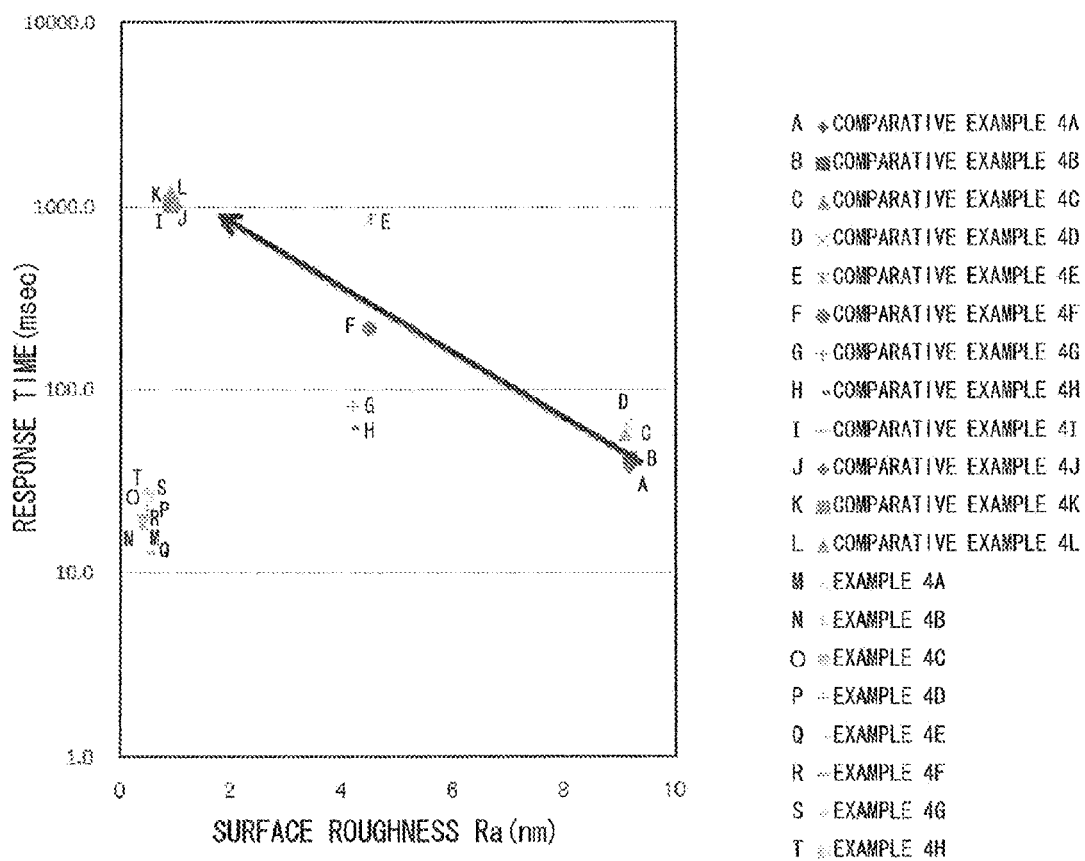
FIG. 18 is a graph plotting a relation between a surface roughness Ra and response time in Example 4A to Example 4H and Comparative example 4A to Comparative example 4L.
Figure 19:
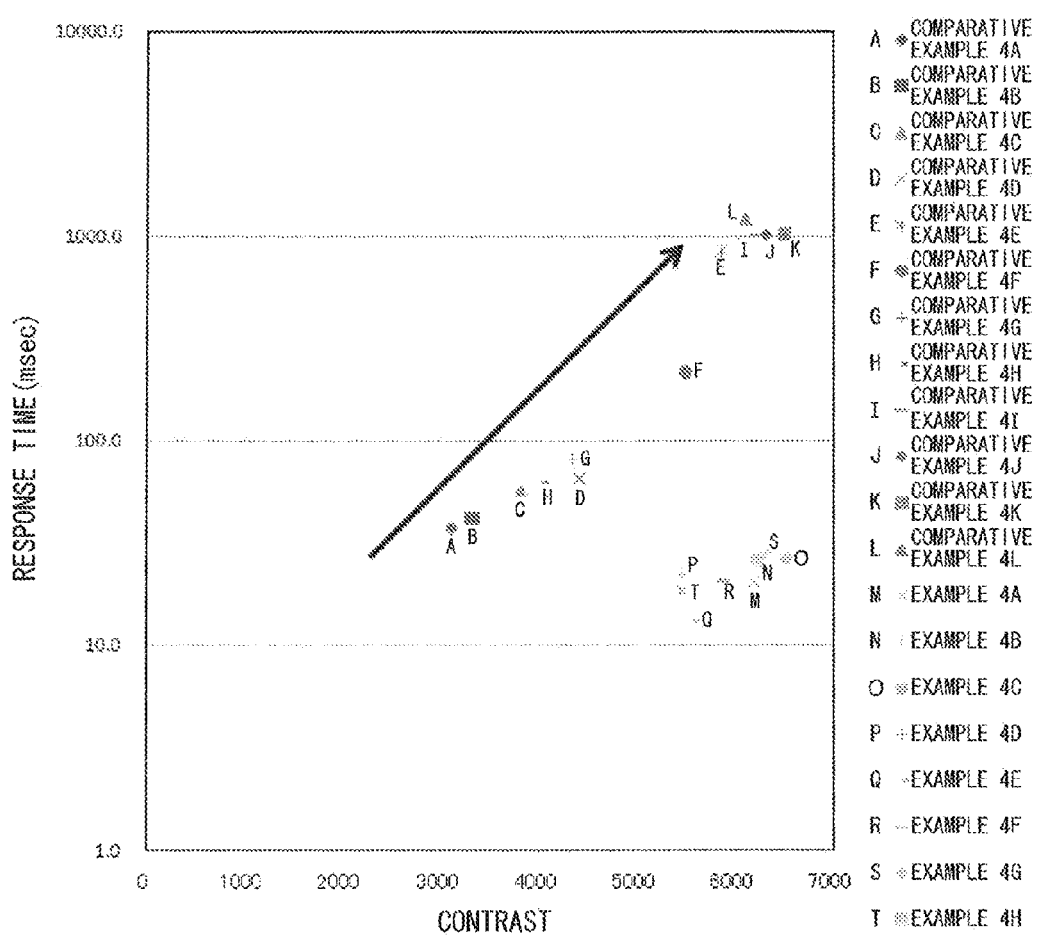
FIG. 19 is a graph plotting a relation between contrast and response time in Example 4A to Example 4H and Comparative example 4A to Comparative example 4L.

FIGS. 17(A), 17(B), and 17(C) illustrate AFM images of the alignment film surface in Example 4A, Comparative example 4A, and Comparative example 4E. FIG. 18 illustrates a graph plotting relation between the surface roughness Ra and response time. FIG. 19 illustrates a graph plotting relation between contrast and response time.

TABLE 5

| Example | Alignment film material | Pre-tilt (deg) | Response rate (millisecond) | Surface roughness Ra (nm) | Contrast |
|---|---|---|---|---|---|
| 4A | a | 1.3 | 20.3 | 0.4 | 6200 |
| 4B | a | 0.9 | 18.6 | 0.4 | 5457 |
| 4C | a | 0.4 | 26.6 | 0.5 | 6521 |
| 4D | a | 0.5 | 22.5 | 0.5 | 5468 |
| 4E | b | 1.6 | 13.2 | 0.5 | 5577 |
| 4F | b | 0.7 | 20.8 | 0.4 | 5890 |
| 4G | b | 0.6 | 28.1 | 0.5 | 6321 |
| 4H | b | 0.5 | 26.2 | 0.5 | 6235 |
| Comparative example | Monomer | | | | |
| 4A | 0.3 wt % | 1.2 | 37.7 | 9.2 | 3114 |
| 4B | 0.3 wt % | 0.9 | 42.1 | 9.2 | 3324 |
| 4C | 0.3 wt % | 0.4 | 57.3 | 9.1 | 3820 |
| 4D | 0.3 wt % | 0.2 | 65.5 | 9.1 | 4423 |
| 4E | 0.1 wt % | 0.2 | 856.9 | 4.5 | 5868 |
| 4F | 0.1 wt % | 0.3 | 216.7 | 4.5 | 5499 |
| 4G | 0.1 wt % | 1.2 | 81.7 | 4.2 | 4343 |
| 4H | 0.1 wt % | 1.8 | 62.8 | 4.2 | 4041 |
| 4I | 0.03 wt % | 0.1 | 1011.6 | 1.0 | 6221 |
| 4J | 0.03 wt % | 0.2 | 1012.4 | 1.0 | 6324 |
| 4K | 0.03 wt % | 0.1 | 1025.8 | 0.9 | 6512 |
| 4L | 0.03 wt % | 0.0 | 1223.1 | 0.9 | 6111 |

After the acryl monomer was polymerized, the polymer projection was formed on the uppermost surface of the alignment film. However, from Comparative example 4A to Comparative example 4L, as the additive amount of the acryl monomer was decreased, the surface roughness value of the alignment film was decreased and the polymer projection formed on the uppermost surface of the alignment film was decreased. In addition, as the surface roughness value of the alignment film was decreased, the contrast value was increased. In Comparative example 4I to Comparative example 4L, the surface roughness Ra was 1 nm or less, and a contrast value of 6000 or more was able to be obtained. However, as the additive amount of the acryl monomer was decreased, the pretilt value was decreased, the response rate was decreased, and thus high speed response was not able to be realized. The reason thereof was as follows. In the case where the surface roughness was 1 nm or less, formation of the polymer projection was not insufficient, a vertical alignment element existed, and domain in which the liquid crystal falling direction was not controlled existed. Meanwhile, in the case where the surface roughness of the alignment film was rough, order parameter of liquid crystal was disturbed, and contrast was lowered. In Comparative example 4A to Comparative example 4L, interrelate well between the surface roughness Ra and response time and between contrast and response time.

Meanwhile, in Example 4A to Example 4H, interrelation did not exist between the surface roughness Ra and response time and between contrast and response time. It was confirmed that in Example 4A to Example 4H, the surface roughness Ra of 1 nm or less and the response rate of 100 millisecond or less that had not been able to be realized in the existing process were able to be realized. In addition, it was confirmed that in Example 4A to Example 4H, response characteristics were able to be easily and stably improved. In Example 4A to Example 4H, the liquid crystal molecules were sandwiched by cross-linking reaction of the polymer compound, and pretilt was given according to the alignment direction of the liquid crystal molecules in driving. Thus, even if the polymer projection was not formed on the surface of the alignment film, pretilt was able to be given to the liquid crystal. Thus, in the liquid crystal device having a surface roughness of the alignment film of 1 nm or less, high contrast and high speed response rate were able to be realized, the response rate to a drive voltage was able to be largely improved, and the response characteristics were able to be improved in a state that favorable display characteristics were retained.

As described above, based on the 1E structure of the present invention, in the present invention, the surface roughness Ra of the first alignment film (or alignment film including the compound after alignment process) was 1 nm or less. In addition, the liquid crystal display unit (liquid crystal display device) having such an alignment film was able to retain superior response rate and high contrast.

Example 5

Example 5

Example 5 relates to the liquid crystal display unit (liquid crystal display device) and the method of manufacturing the same according to the second aspect of the present invention, and the method of manufacturing a liquid crystal display unit (liquid crystal display device) according to the third aspect of the present invention. In Example 5, a compound before alignment process/a compound after alignment process having a photosensitive functional group was used. Specifically, the liquid crystal display unit having a composition and a structure similar to those illustrated in FIG. 12 was fabricated by using an azobenzene compound shown in Formula (AZ-11) to Formula (AZ-17) described below as the compound before alignment process having a photosensitive functional group and response characteristics were examined.

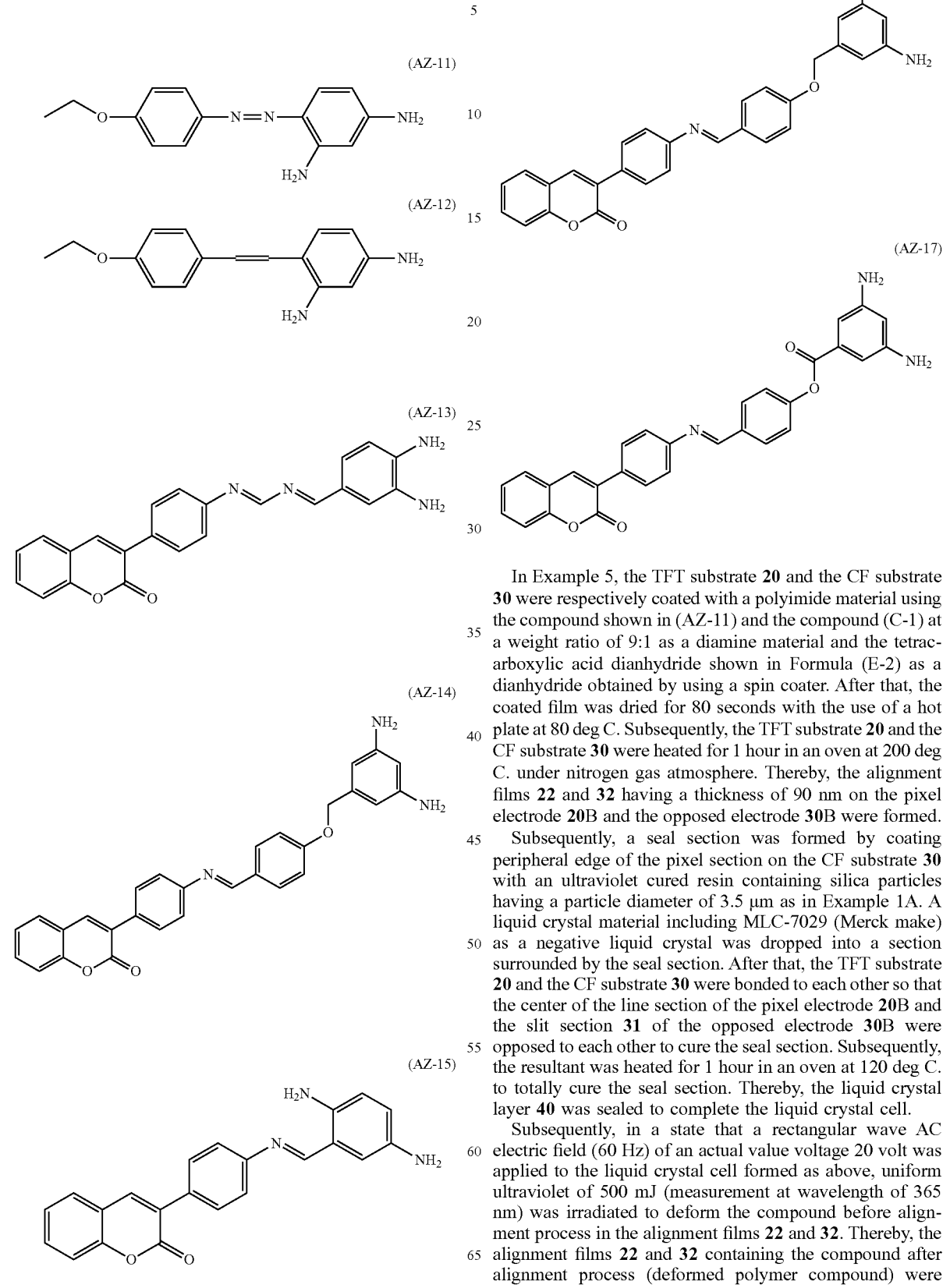

In Example 5, the TFT substrate 20 and the CF substrate 30 were respectively coated with a polyimide material using the compound shown in (AZ-11) and the compound (C-1) at a weight ratio of 9:1 as a diamine material and the tetracarboxylic acid dianhydride shown in Formula (E-2) as a dianhydride obtained by using a spin coater. After that, the coated film was dried for 80 seconds with the use of a hot plate at 80 deg C. Subsequently, the TFT substrate 20 and the CF substrate 30 were heated for 1 hour in an oven at 200 deg C. under nitrogen gas atmosphere. Thereby, the alignment films 22 and 32 having a thickness of 90 nm on the pixel electrode 20B and the opposed electrode 30B were formed.

Subsequently, a seal section was formed by coating peripheral edge of the pixel section on the CF substrate 30 with an ultraviolet cured resin containing silica particles having a particle diameter of 3.5 μm as in Example 1A. A liquid crystal material including MLC-7029 (Merck make) as a negative liquid crystal was dropped into a section surrounded by the seal section. After that, the TFT substrate 20 and the CF substrate 30 were bonded to each other so that the center of the line section of the pixel electrode 20B and the slit section 31 of the opposed electrode 30B were opposed to each other to cure the seal section. Subsequently, the resultant was heated for 1 hour in an oven at 120 deg C. to totally cure the seal section. Thereby, the liquid crystal layer 40 was sealed to complete the liquid crystal cell.

Subsequently, in a state that a rectangular wave AC electric field (60 Hz) of an actual value voltage 20 volt was applied to the liquid crystal cell formed as above, uniform ultraviolet of 500 mJ (measurement at wavelength of 365 nm) was irradiated to deform the compound before alignment process in the alignment films 22 and 32. Thereby, the alignment films 22 and 32 containing the compound after alignment process (deformed polymer compound) were formed on both the TFT substrate 20 and the CF substrate 30. Accordingly, the liquid crystal display unit (liquid crystal display device) in which the liquid crystal molecule 41A and 41B on the TFT substrate 20 and the CF substrate 30 side were given with pretilt was able to be completed. Finally, a pair of polarization plates was attached to the outside of the liquid crystal display unit so that each absorption axis was perpendicular to each other.

A liquid crystal display unit (liquid crystal display device) was completed in the same manner as that of the foregoing procedure by using the compounds shown in Formula (AZ-12) to Formula (AZ-17) instead of the compound shown in Formula (AZ-11).

For comparison, a liquid crystal display unit (liquid crystal display device) was completed in the same manner as that of the foregoing procedure by using the compound shown in the following formula instead of the compound shown in Formula (AZ-11). The liquid crystal display unit (liquid crystal display device) is referred to as Comparative example 5.

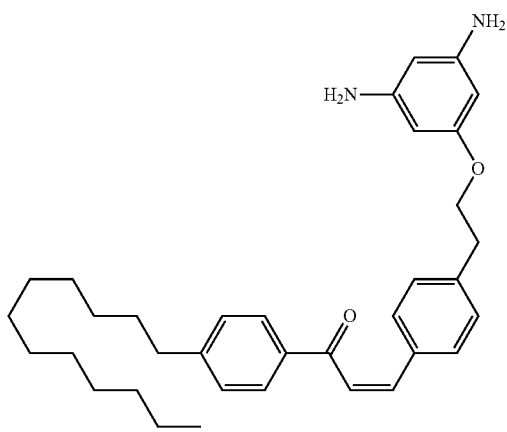 [SMILES: CCCCCCCCCCCCc1ccc(C(=O)/C=C\c2ccc(CCOc3cc(N)cc(N)c3)cc2)cc1]

For the liquid crystal display units (liquid crystal display devices) fabricated as above, the pretilt θ and the response time were measured. Accordingly, the result illustrated in Table 6 was obtained.

TABLE 6

| Used compound | Pretilt (deg) | Response rate (millisecond) |
| --- | --- | --- |
| Formula (AZ-11) | 0.5 | 18.2 |
| Formula (AZ-12) | 0.4 | 19.3 |
| Formula (AZ-13) | 1.2 | 12.0 |
| Formula (AZ-14) | 1.4 | 11.7 |
| Formula (AZ-15) | 0.9 | 15.2 |
| Formula (AZ-16) | 1.5 | 10.3 |
| Formula (AZ-17) | 1.4 | 11.4 |
| Comparative example 5 | 0.1 | 51.0 |

From Table 6, it was found that the response rate in Example 5 was significantly higher than that of Comparative example 5. Further, in Comparative example 5, the pretilt θ was hardly given.

The present invention has been described with reference to the embodiments and the examples. However, the present invention is not limited to the embodiments and the like, and various modifications may be made. For example, in the embodiments and the examples, the description has been given of the VA mode liquid crystal display unit (liquid crystal display device). However, the present invention is not limited thereto, but the present invention is able to apply to other display mode such as TN mode, IPS (In Plane Switching) mode, FFS (Fringe Field Switching) mode, and OCB (Optically Compensated Bend) mode. In these modes, similar effect is able to be obtained. However, in the present invention, compared to a case not provided with pretilt process, particularly higher improvement effect of response characteristics is able to be demonstrated in VA mode than in IPS mode and FFS mode.

Further, in the embodiments and the examples, the description has been exclusively given of the transmissive liquid crystal display unit (liquid crystal display device). However, the present invention is not limited to the transmissive liquid crystal display unit (liquid crystal display device), but the present invention may be applied to a reflective liquid crystal display unit (liquid crystal display device). In the case of the reflective liquid crystal display unit (liquid crystal display device), the pixel electrode is made of an electrode material having light reflectivity such as aluminum.

The invention claimed is:

1. A method of manufacturing a liquid crystal display unit comprising the steps of:
   forming a first alignment film including a polymer compound comprising a main chain and a side chain having a crosslinkable functional group bonded to the main chain;
   forming a second alignment film on a second substrate;
   arranging the first and second substrates so that the first alignment film and the second alignment film are opposed to each other, and sealing a liquid crystal layer containing a liquid crystal molecule having positive dielectric constant anisotropy between the first alignment film and the second alignment film; and
   bridging the polymer compound through the crosslinkable functional group of the polymer compound to give pretilt to the liquid crystal molecule after sealing the liquid crystal layer,
   wherein,
   bridging of the polymer compound occurs through the crosslinkable functional group of the side chain from a different main chain or the same main chain of the polymer.

2. The method of manufacturing a liquid crystal display unit according to claim 1, wherein while the liquid crystal molecule is aligned by applying predetermined electric field to the liquid crystal layer, the side chain of the polymer compound is cross-linked by radiating ultraviolet.

3. A method of manufacturing a liquid crystal display unit comprising the steps of:
   forming a first alignment film including a polymer compound having a photosensitive functional group as a side chain on a first substrate;
   forming a second alignment film on a second substrate;
   arranging the first and second substrates so that the first alignment film and the second alignment film are opposed to each other, and sealing a liquid crystal layer containing a liquid crystal molecule having positive dielectric constant anisotropy between the first alignment film and the second alignment film; and
   deforming a portion of the polymer compound through the photosensitive functional group polymer compound to give pretilt to the liquid crystal molecule after sealing the liquid crystal layer,
   wherein,
   the deforming of the polymer compound through the photosensitive functional group polymer compound occurs between a side chain to a main chain or a side chain to a side chain of the polymer.

4. The method of manufacturing a liquid crystal display unit according to claim 3, wherein while the liquid crystal molecule is aligned by applying predetermined electric field to the liquid crystal layer, the side chain of the polymer compound is deformed by radiating ultraviolet.

5. A method of manufacturing a liquid crystal display unit comprising the steps of:
forming a first alignment film including a polymer compound having a crosslinkable functional group or a photosensitive functional group as a side chain on a first substrate;
forming a second alignment film on a second t substrate;
arranging the first and second substrates so that the first alignment film and the second alignment film are opposed to each other, and sealing a liquid crystal layer containing a liquid crystal molecule having positive dielectric constant anisotropy between the first alignment film and the second alignment film; and
bridging or deforming the polymer compound by radiating energy to the polymer compound to give pretilt to the liquid crystal molecule after sealing the liquid crystal layer.

6. The method of manufacturing a liquid crystal display unit according to claim 5, wherein while the liquid crystal molecule is aligned by applying predetermined electric field to the liquid crystal layer, ultraviolet as the energy line is irradiated to the polymer compound.

7. The method of manufacturing a liquid crystal display unit according to claim 1, wherein:
the polymer compound includes a side chain compound represented by Formula (1): -R1-R2-R3, and
(a) R1 represents a straight chain or branched chain bivalent organic group with the carbon number of 3 or more, and is bonded to a main chain of the polymer compound, (b) R2 represents a bivalent organic group containing a plurality of ring structures, and one of atoms composing the ring structures is bonded to R1, and (c) R3 represents a hydrogen atom, a halogen atom, an alkyl group, an alkoxy group, and a monovalent group having a carbonate group, or a derivative thereof.

8. The method of manufacturing a liquid crystal display unit according to claim 1, wherein:
the polymer compound includes a side chain compound represented by Formula (2) -R11-R12-R13-R14, and
(a) R11 represents a straight chain or branched chain bivalent organic group with the carbon number from 1 to 20 both inclusive, that may contain an ether group or an ester group, and is bonded to a main chain of the polymer compound or R11 represents an ether group or an ester group, and is bonded to the main chain of the polymer compound, (b) R12 represents a bivalent group containing one structure of chalcone, cinnamate, cinnamoyl, coumarin, maleimide, benzophenone, norbornene, orizanol, and chitosan, or an ethynylene group, (c) R13 represents a bivalent organic group containing a plurality of ring structures, and (d) R14 represents a hydrogen atom, a halogen atom, an alkyl group, an alkoxy group, and a monovalent group having a carbonate group or a derivative thereof.

9. The method of manufacturing a liquid crystal display unit according to claim 1, wherein:
a compound obtained by bridging the polymer compound includes a side chain bonded to a main chain,
the side chain includes a cross-linked section,
an end structure section is bonded to the cross-linked section, and
the liquid crystal molecule is located along the end structure section or is sandwiched between the end structure sections.

10. The method of manufacturing a liquid crystal display unit according to claim 3, wherein:
a compound obtained by deforming the polymer compound includes a side chain bonded to a main chain,
the side chain includes a deformed section,
an end structure section bonded to the deformed section, and
the liquid crystal molecule is located along the end structure section or is sandwiched between the end structure sections.

11. The method of manufacturing a liquid crystal display unit according to claim 5, wherein:
a compound obtained by radiating energy line to the polymer compound includes a side chain bonded to a main chain,
the side chain includes a cross-linked section, a deformed section or both,
an end structure section is bonded to the cross-linked section, the deformed section, or both, and
the liquid crystal molecule is located along the end structure section or is sandwiched between the end structure sections.

12. The method of manufacturing a liquid crystal display unit according to claim 1, wherein:
a compound obtained by bridging the polymer compound includes a side chain bonded to a main chain,
the side chain includes a cross-linked section and
a mesogenic group bonded to the cross-linked section.

13. The method of manufacturing a liquid crystal display unit according to claim 3, wherein:
a compound obtained by deforming the polymer compound includes a side chain bonded to a main chain,
the side chain includes a deformed section, and
a mesogenic group bonded to the deformed section.

14. The method of manufacturing a liquid crystal display unit according to claim 5, wherein:
a compound obtained by radiating energy line to the polymer compound includes a side chain bonded to a main chain,
the side chain includes a cross-linked section, a deformed section, or both,
a mesogenic group is bonded to a part of the cross-linked section, the deformed section or both.

15. The method of manufacturing a liquid crystal display unit according to claim 1, wherein a surface roughness Ra of the first alignment film is 1 nm or less.

16. The method of manufacturing a liquid crystal display unit according to claim 1, wherein the second alignment film includes the polymer compound composing the first alignment film.

17. The method of manufacturing a liquid crystal display unit according to claim 1, comprising an alignment regulation section including a slit formed in an electrode or a projection provided in the substrate is provided.

18. The method of claim 8, where R11 represents a straight chain or branched chain bivalent organic group with the carbon number from 3 to 12 both inclusive, that may contain an ether group or an ester group, and is bonded to a main chain of the polymer compound.

* * * * *